US007202356B2

(12) United States Patent
Pollak et al.

(10) Patent No.: US 7,202,356 B2
(45) Date of Patent: Apr. 10, 2007

(54) FRUCTOSE-BISPHOSPHATE ALDOLASE REGULATORY SEQUENCES FOR GENE EXPRESSION IN OLEAGINOUS YEAST

(75) Inventors: Dana M. Walters Pollak, Media, PA (US); Quinn Qun Zhu, West Chester, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 132 days.

(21) Appl. No.: 10/987,548

(22) Filed: Nov. 12, 2004

(65) Prior Publication Data
US 2005/0130280 A1    Jun. 16, 2005

Related U.S. Application Data

(60) Provisional application No. 60/519,971, filed on Nov. 14, 2003.

(51) Int. Cl.
*C07H 21/04* (2006.01)
*C12Q 1/68* (2006.01)
*G01N 33/53* (2006.01)
*C12N 15/00* (2006.01)
*C12N 15/63* (2006.01)
*C12P 21/04* (2006.01)
*C12N 1/19* (2006.01)

(52) U.S. Cl. ............... 536/24.1; 435/6; 435/7.31; 435/69.1; 435/69.9; 435/320.1

(58) Field of Classification Search ............... None
See application file for complete search history.

(56) References Cited

U.S. PATENT DOCUMENTS

| 4,937,189 A | 6/1990 | Davidow et al. |
| 6,265,185 B1 | 7/2001 | Muller et al. |
| 2005/0014270 A1 | 1/2005 | Picataggio et al. |

FOREIGN PATENT DOCUMENTS

| EP | 0 005 277 B1 | 1/1982 |
| EP | 0 220 864 B1 | 3/1993 |
| EP | 0 832 258 B1 | 4/2002 |

OTHER PUBLICATIONS

Espeso et al. Three Binding Sites for the *Aspergillus nidulans* PacC Zinc-finger Transcription Factor Are Necessary and Sufficient for Regulation by Ambient pH of the Isopenicillin N Synthase Gene Promoter. J. Biol. Chem. 271 (46): 28825-28830. 1996.*
Sylvie Blanchin-Roland et al., Two Upstream Activation Sequences Control the Expression of the XPR2 Gene in the Yeast *Yarrowia lipolytica*, Molecular and Cellular Biology, vol. 14(1):327-338, 1994.
Rosaura Rodicio et al., Transcriptional control of yeast phosphoglycerate mutase-encoding gene, Gene, vol. 125:125-133, 1993.
Grant A. Bitter et al., Expression of heterologous genes in *Saccharomyces cerevisiae* from vectors utilizing the glyceraldehyde-3-phosphate dehydrogenase gene promoter, Gene, vol. 32:263-274, 1984.
Colin Ratledge, Microbial Oils and Fats: An Assessment of Their Commercial Potential, C. Prog. Ind. Microbiol., vol. 16:119-206, 1992.
Thomas Juretzek et al., Comparison of Promoters Suitable for Regulated Overexpression of beta-Galactosidase in the Alkane-Utilizing Yeast *Yarrowia lipolytica*, Biotechnol. Bioprocess Eng., vol. 5:320-326, 2000.
Concetta Compagno et. al., The Promoter of *Saccharomyces cerevisiae* FBA1 Gene Contains a Single Positive Upstream Regulatory Element, FEBS Letter, 1991, pp. 97-100, vol. 293.
Catherine Madzak et. al., Functional Analysis of Upstream Regulating Regions From the *Yarrowia Lipolytica* XPR2 Promoter, Microbiology, 1999, pp. 75-87, vol. 145.
Thomas Juretzek et. al., Vectors for Gene Expression and Amplification in the Yeast *Yarrowia lipolytica*, Yeast, 2001, pp. 97-113, vol. 18.

* cited by examiner

*Primary Examiner*—David Guzo
*Assistant Examiner*—Michele K. Joike

(57) ABSTRACT

The regulatory sequences (i.e., promoter regions, introns and enhancers) associated with the *Yarrowia lipolytica* gene encoding fructose bis-phospate aldolase (FBA1) have been found to be particularly effective for the expression of heterologus genes in oleaginous yeast. The promoter regions of the invention have been shown to drive high-level expression of genes involved in the production of ω-3 and ω-6 fatty acids.

8 Claims, 18 Drawing Sheets

Figure 1B:
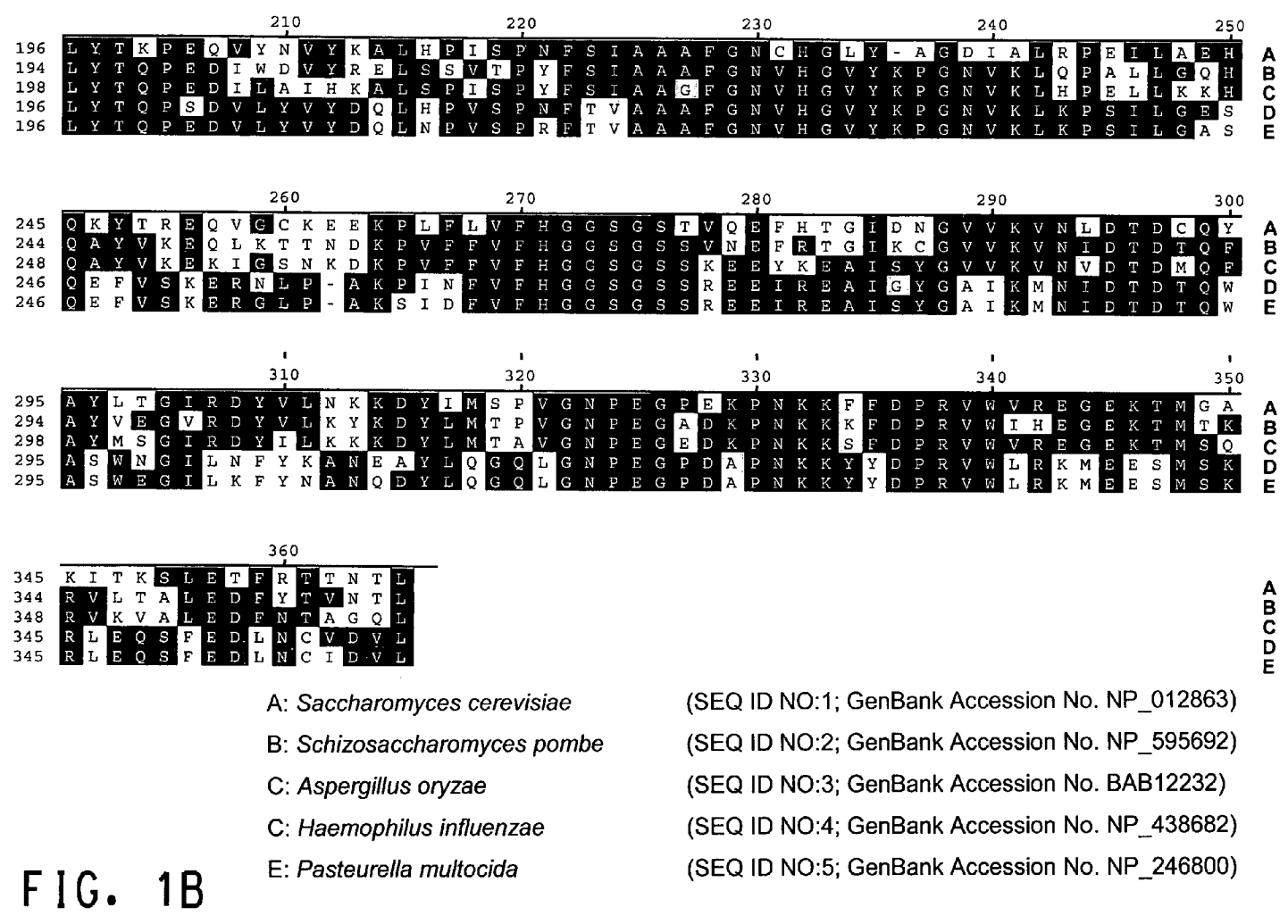

A: Saccharomyces cerevisiae (SEQ ID NO:1; GenBank Accession No. NP_012863)
B: Schizosaccharomyces pombe (SEQ ID NO:2; GenBank Accession No. NP_595692)
C: Aspergillus oryzae (SEQ ID NO:3; GenBank Accession No. BAB12232)
C: Haemophilus influenzae (SEQ ID NO:4; GenBank Accession No. NP_438682)
E: Pasteurella multocida (SEQ ID NO:5; GenBank Accession No. NP_246800)

$$\overset{-4}{C}AAA\mathbf{ATG}\overset{+6}{N}CG \text{ [SEQ ID NO:56]}$$
$$\phantom{CAAAA}A\phantom{TGN}CC$$
$$\phantom{CAAAATG}TC$$
$$\phantom{CAAAATGN}A$$

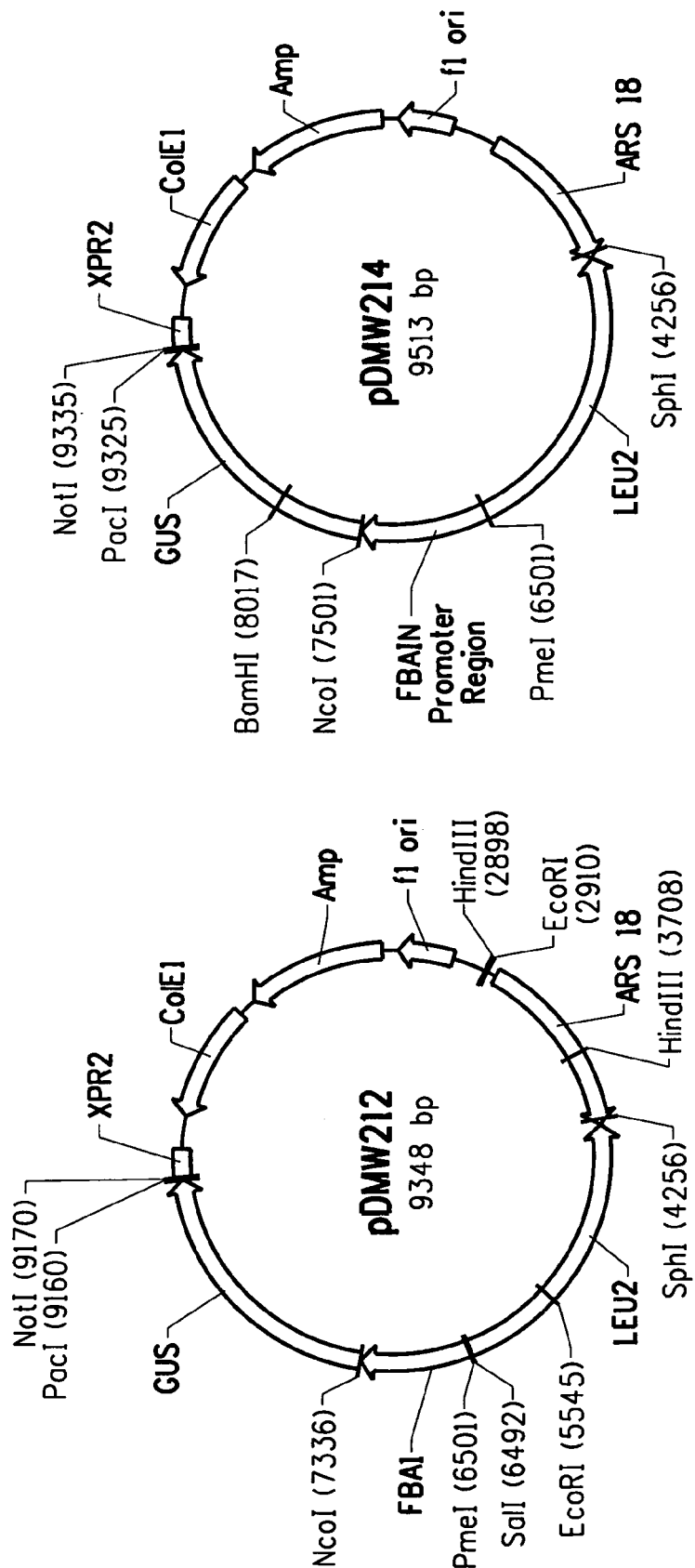

FBAIN

GPM

GPM::FBAIN

TEF

FRUCTOSE-BISPHOSPHATE ALDOLASE REGULATORY SEQUENCES FOR GENE EXPRESSION IN OLEAGINOUS YEAST

This application claims the benefit of U.S. Provisional Application No. 60/519971, filed Nov. 14, 2003.

FIELD OF THE INVENTION

This invention is in the field of biotechnology. More specifically, this invention pertains to regulatory sequences (i.e., promoter regions, introns and enhancers) isolated from *Yarrowia lipolytica*, useful for gene expression in oleaginous yeast.

BACKGROUND OF THE INVENTION

Oleaginous yeast are defined as those organisms that are naturally capable of oil synthesis and accumulation, wherein oil accumulation ranges from at least about 25% up to about 80% of the cellular dry weight. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeast include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis* and *Yarrowia lipolytica* (formerly classified as *Candida lipolytica*).

The technology for growing oleaginous yeast with high oil content is well developed (for example, see EP 0 005 277B1; Ratledge, C., *Prog. Ind. Microbiol.* 16:119–206 (1982)). And, these organisms have been commercially used for a variety of purposes in the past. For example, various strains of *Yarrowa lipolytica* have historically been used for the manufacture and production of: isocitrate lyase; lipases; polyhydroxyalkanoates; citric acid; erythritol; 2-oxoglutaric acid; γ-decalactone; γ-dodecalactone; and pyruvic acid. Most recently, however, the natural abilities of oleaginous yeast have been enhanced by advances in genetic engineering, resulting in organisms capable of producing polyunsaturated fatty acids ("PUFAs"). Specifically, Picataggio et al. have demonstrated that *Yarrowia lipolytica* can be engineered for production of ω-3 and ω-6 fatty acids, by introducing and expressing genes encoding the ω-3/ω-6 biosynthetic pathway (co-pending U.S. patent application Ser. No. 10/840,579).

Recombinant production of any heterologous protein is generally accomplished by constructing an expression cassette in which the DNA coding for the protein of interest is placed under the control of appropriate regulatory sequences (i.e., promoters) suitable for the host cell. The expression cassette is then introduced into the host cell (usually by plasmid-mediated transformation or targeted integration into the host genome) and production of the heterologous protein is achieved by culturing the transformed host cell under conditions necessary for the proper function of the promoter contained within the expression cassette. Thus, the development of new host cells (e.g., oleaginous yeast) for recombinant production of proteins generally requires the availability of promoters that are suitable for controlling the expression of a protein of interest in the host cell.

A variety of strong promoters have been isolated from *Saccharomyces cerevisiae* that are useful for heterologous gene expression in yeast. For example, a glyceraldehyde-3-phosphate dehydrogenase (GPD) promoter was described by Bitter, G. A., and K. M. Egan (*Gene*, 32(3):263–274 (1984)); and, a phosphoglycerate mutase (GPM1) promoter was investigated by Rodicio, R. et al. (*Gene*, 125(2): 125–133 (1993)). Several promoters have also been isolated from *Yarrowia lipolytica* that have been suitable for the recombinant expression of proteins. For example, U.S. Pat. No. 4,937,189 and EP220864 (Davidow et al.) disclose the sequence of the XPR2 gene (which encodes an inducible alkaline extracellular protease) and upstream promoter region for use in expression of heterologous proteins. However, this promoter is only active at a pH above 6.0 on media lacking preferred carbon and nitrogen sources; and full induction requires high levels of peptone in the culture media. Subsequent analysis of the XPR2 promoter sequence by Blanchin-Roland, S. et al. (EP832258; *Mol. Cell Biol.* 14(1):327–338 (1994)) determined that hybrid promoters containing only parts of the XPR2 promoter sequence may be used to obtain high level expression in *Yarrowia*, without the limitations resulting from use of the complete promoter sequence.

U.S. Pat. No. 6,265,185 (Muller et al.) describe yeast promoters from *Yarrowia lipolytica* for the translation elongation factor EF1-α (TEF) protein and ribosomal protein S7 that are suitable for expression cloning in yeast and heterologous expression of proteins. These promoters were improved relative to the XPR2 promoter when tested for yeast promoter activity on growth plates (Example 9, U.S. Pat. No. 6,265,185) and based on their activity in the pH range of 4–11. The *Yarrowia* GPD and GPM promoters have also been isolated and proved to be strong promoters (copending U.S. patent application Ser. No. 10/869,630, herein incorporated entirely by reference).

Despite the utility of these known promoters, however, there is a need for new improved yeast regulatory sequences for metabolic engineering of yeast (oleaginous and non-oleaginous) and for controlling the expression of heterologous genes in yeast. Furthermore, possession of a suite of promoters that are regulatable under a variety of natural growth and induction conditions in yeast will play an important role in industrial settings, wherein it is desirable to express heterologous polypeptides in commercial quantities in said hosts for economical production of those polypeptides. Thus, it is an object of the present invention to provide such regulatory sequences that will be useful for gene expression in a variety of yeast cultures, and preferably in *Yarrowia* sp. cultures and other oleaginous yeast.

Applicants have solved the stated problem by identifying a gene (fba1) encoding fructose-bisphosphate aldolase (FBA1) from *Yarrowia lipolytica* and the regulatory sequences responsible for driving expression of this native gene. The promoter, intron and enhancer are useful for expression of heterologous genes in *Yarrowia* and the promoter regions have improved activity with respect to the previously described *Yarrowia lipolytica* TEF, GPD and GPM promoters.

SUMMARY OF THE INVENTION

The present invention provides methods for the expression of a coding region of interest in a transformed yeast cell, using regulatory sequences of the fructose-bisphosphate aldolase gene (fba1). Accordingly, the present invention provides a method for the expression of a coding region of interest in a transformed yeast cell comprising:
  (a) providing a transformed yeast cell having a chimeric gene comprising:
    (i) a regulatory sequence of the *Yarrowia* fba1 gene; and, (ii) a coding region of interest expressible in the yeast cell;
wherein the regulatory sequence is operably linked to the coding region of interest; and
(b) growing the transformed yeast cell of step (a) under conditions whereby the chimeric gene of step (a) is expressed.

Preferred regulatory sequences of the *Yarrowia* fba1 gene include the FBA promoter region; the FBAIN promoter region; the FBAINm promoter region; and the chimeric promoter comprising the fba1 intron.

In another embodiment the invention provides method for the production of an ω-3 or an ω-6 fatty acid comprising:
a) providing a transformed oleaginous yeast comprising a chimeric gene, the chimeric gene comprising:
  (i) a regulatory sequence of the *Yarrowia* fba1 gene; and,
  (ii) a coding region encoding at least one enzyme of the ω-3/ω-6 fatty biosynthetic pathway;
  wherein the regulatory sequence and coding region are operably linked;
b) growing the transformed oleaginous yeast of step (a) under conditions whereby the at least one enzyme of the ω-3/ω-6 fatty acid biosynthetic pathway is expressed and a ω-3 or ω-6 fatty acid is produced; and
c) optionally recovering the ω-3 or ω-6 fatty acid.

Additionally the invention provides an isolated nucleic acid molecule comprising a FBA, FBAIN or FBAINm promoter selected from the group consisting SEQ ID NOs: 17, 18, 19, 25, 26, 27, 46 and 72, as well as an isolated nucleic acid molecule comprising an intron of the *Yarrowia* fba1 gene as set forth in SEQ ID NO :55.

In similar fashion the invention provides A plasmid comprising a FBA, FBAIN or FBAINm promoter region and a plasmid comprising a fba1 intron

BRIEF DESCRIPTION OF THE DRAWINGS AND SEQUENCE DESCRIPTIONS

FIGS. 1A and 1B shows an alignment of known fructose-bisphosphate aldolase (FBA1) proteins from *Saccharomyces cerevisiae, Schizosaccharomyces pombe, Aspergillus oryzae, Haemophilus influenzae* and *Pasteurella multocida*, used to identify two conserved regions within the sequence alignment.

Figure 5B:
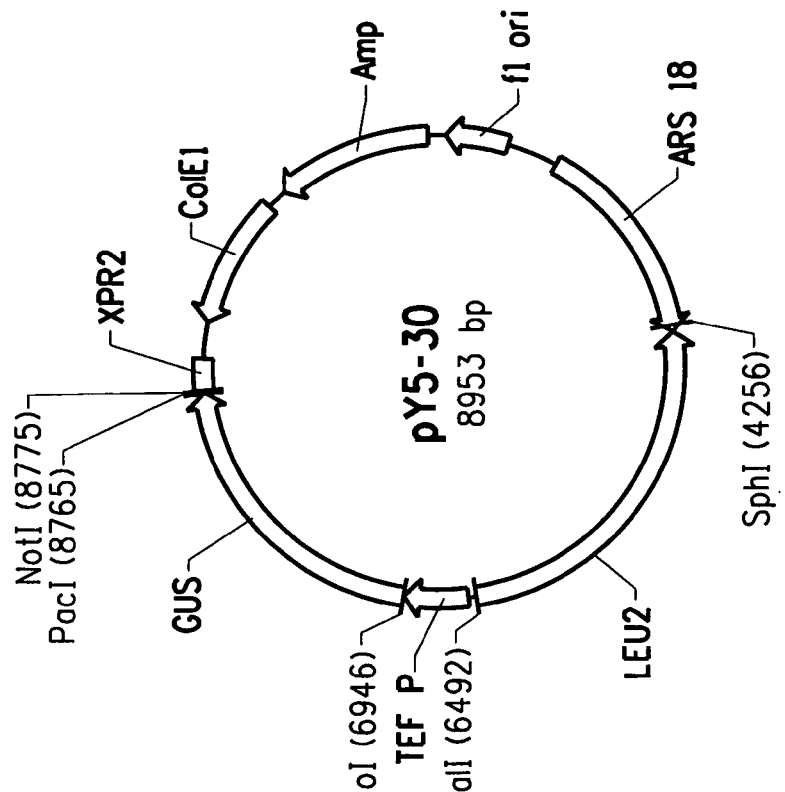
Figure 5A:
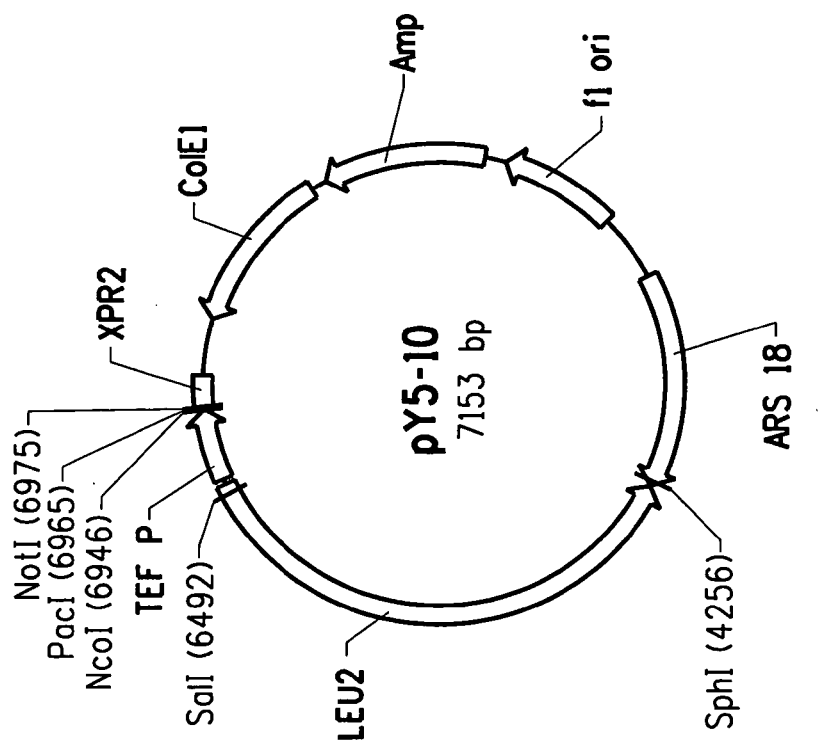

FIGS. 5A and 5B provide plasmid maps for pY5–10 and pY5–30, respectively.

Figure 6:
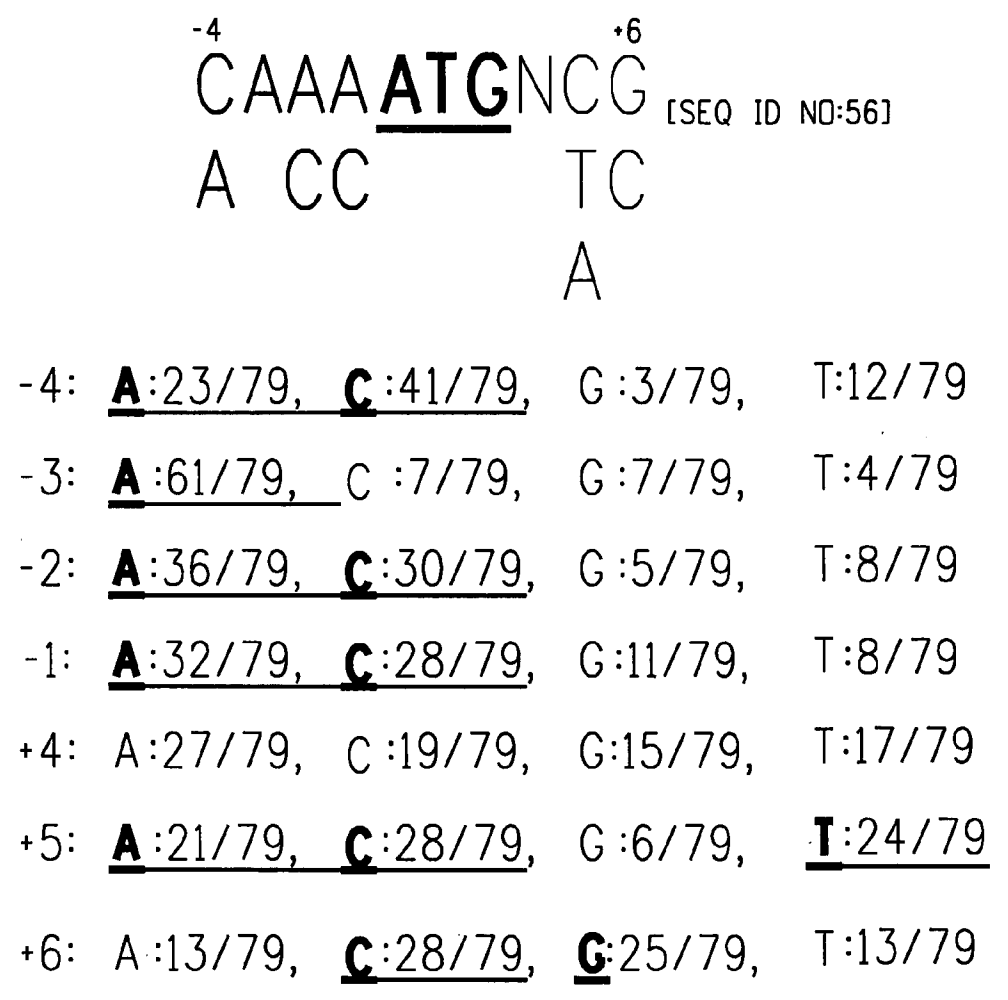

FIG. 6 provides the consensus motif around the translation initiation codon of *Yarrowia*.

FIGS. 7A, 7B, 7C and 7D provide plasmid maps for pDMW212, pDMW214, pYZGDG and pYZGMG, respectively.

Figure 8A:
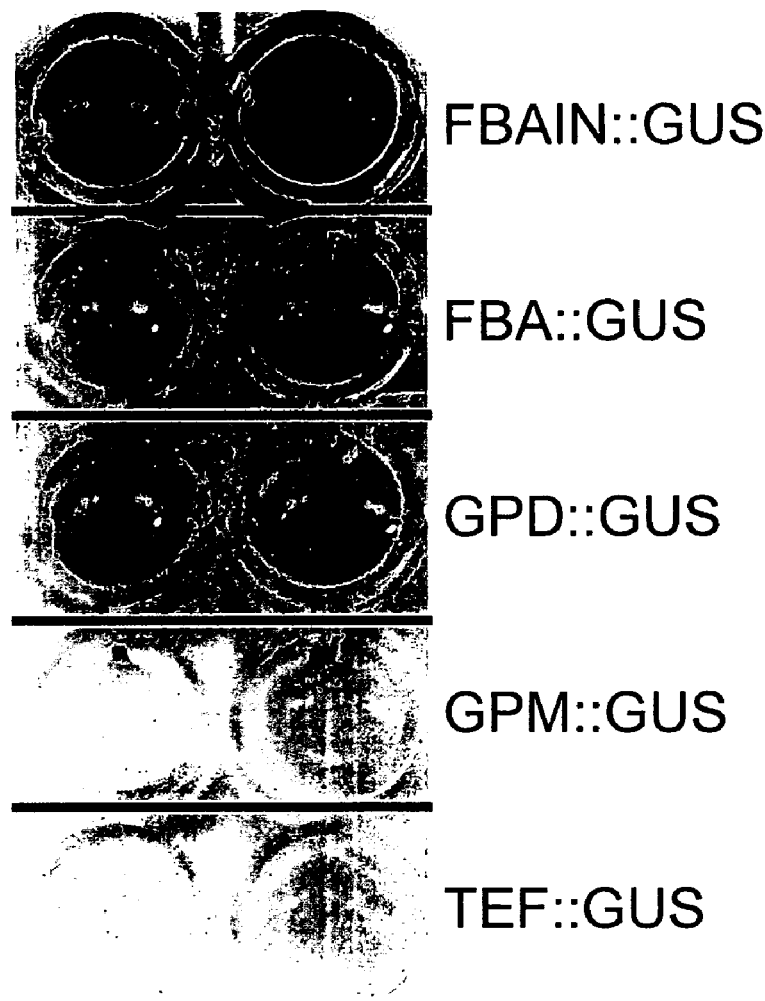
Figure 8B:
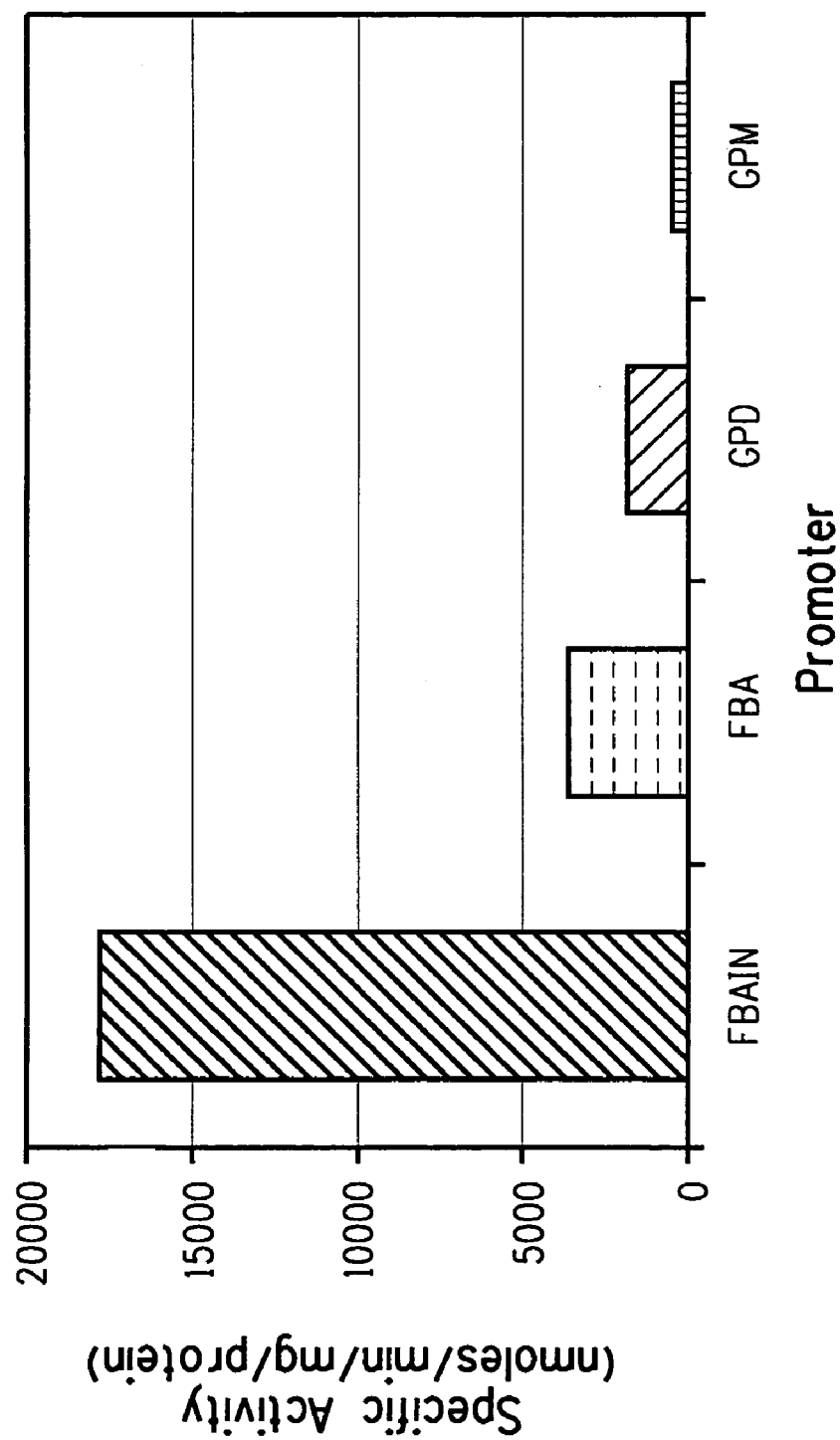
Figure 8C:
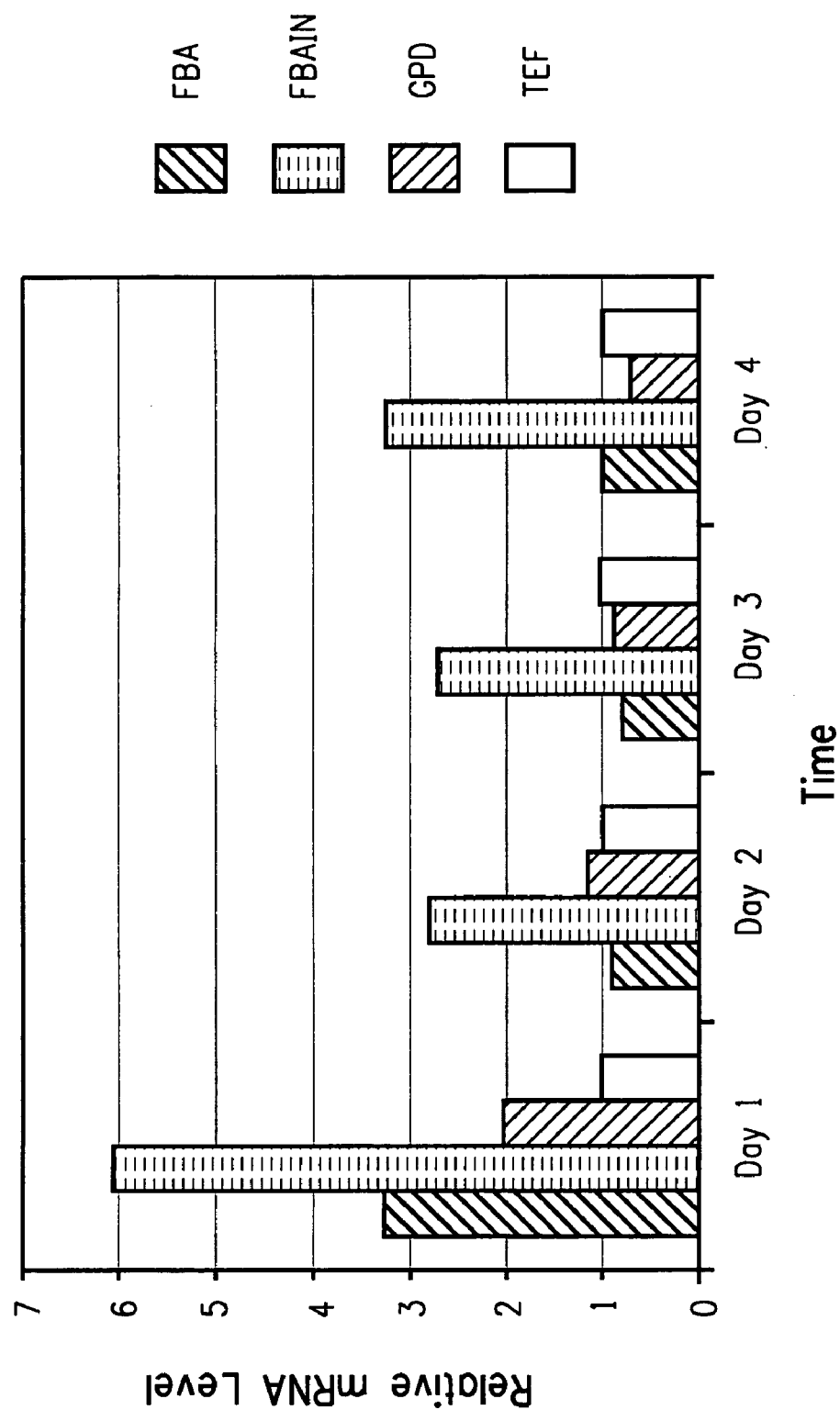

FIG. 8A illustrates the relative promoter activities of TEF, GPD, GPM, FBA and FBAIN in *Yarrowia lipolytica* as determined by histochemical staining. FIG. 8B is a graph comparing the promoter activity of GPD, GPM, FBA and FBAIN as determined fluorometrically. FIG. 8C graphically summarizes the results of Real Time PCR relative quantitation, wherein the GUS mRNA in different *Yarrowia lipolytica* strains (i.e., expressing GPD::GUS, FBA::GUS or FBAIN::GUS chimeric genes) was quantified to the mRNA level of the *Yarrowia lipolytica* strain expressing pY5–30 (i.e., a chimeric TEF::GUS gene).

Figure 9A:
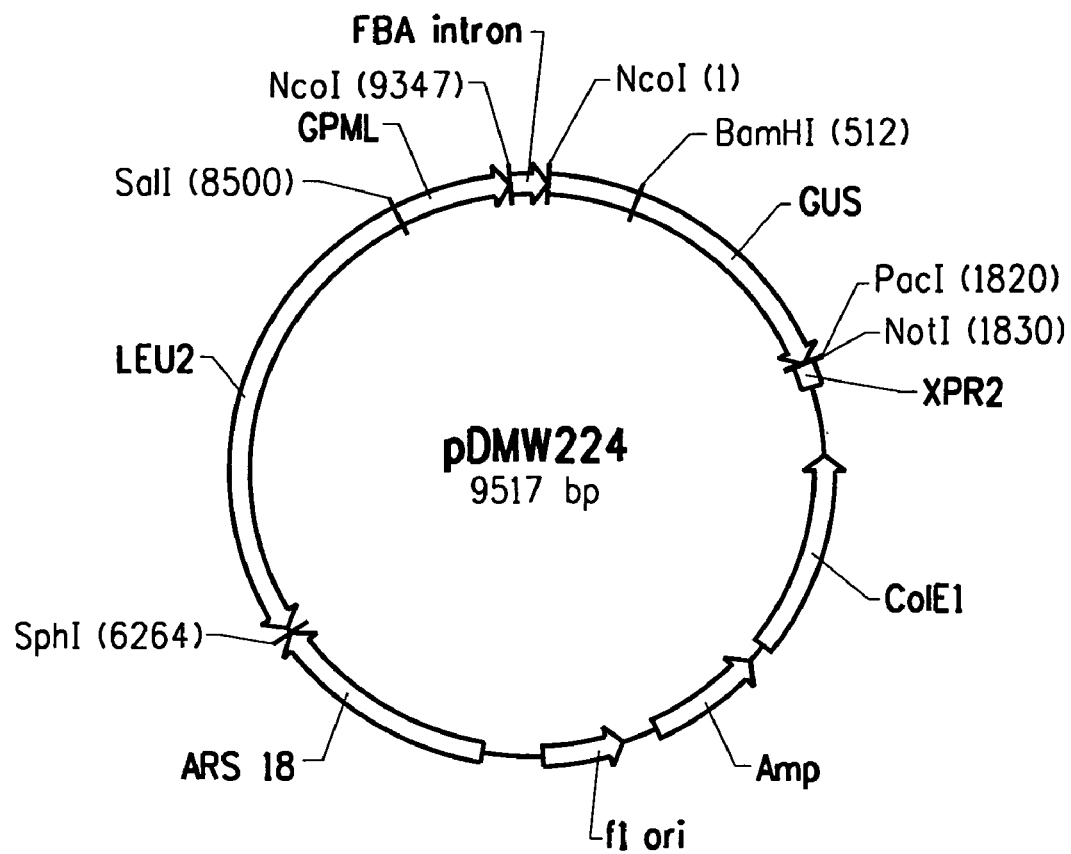
Figure 9B:
Figure 9B:
Figure 9B:
Figure 9B:
Figure 9C:
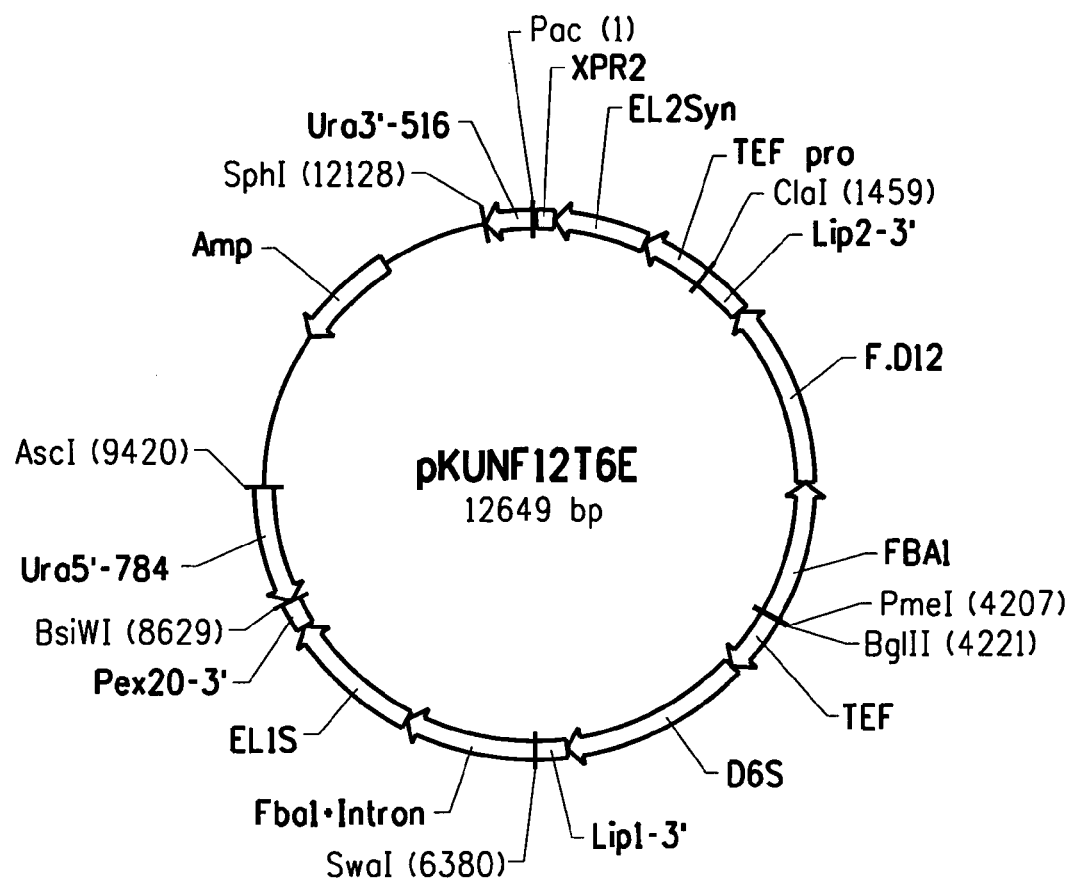

FIG. 9A provides a plasmid map for pDMW224. FIG. 9B illustrates the relative promoter activities of TEF, FBAIN, GPM and GPM::FBAIN in *Yarrowia lipolytica* as determined by histochemical staining. FIG. 9C provides a plasmid map for pKUNF12T6E.

Figure 10:
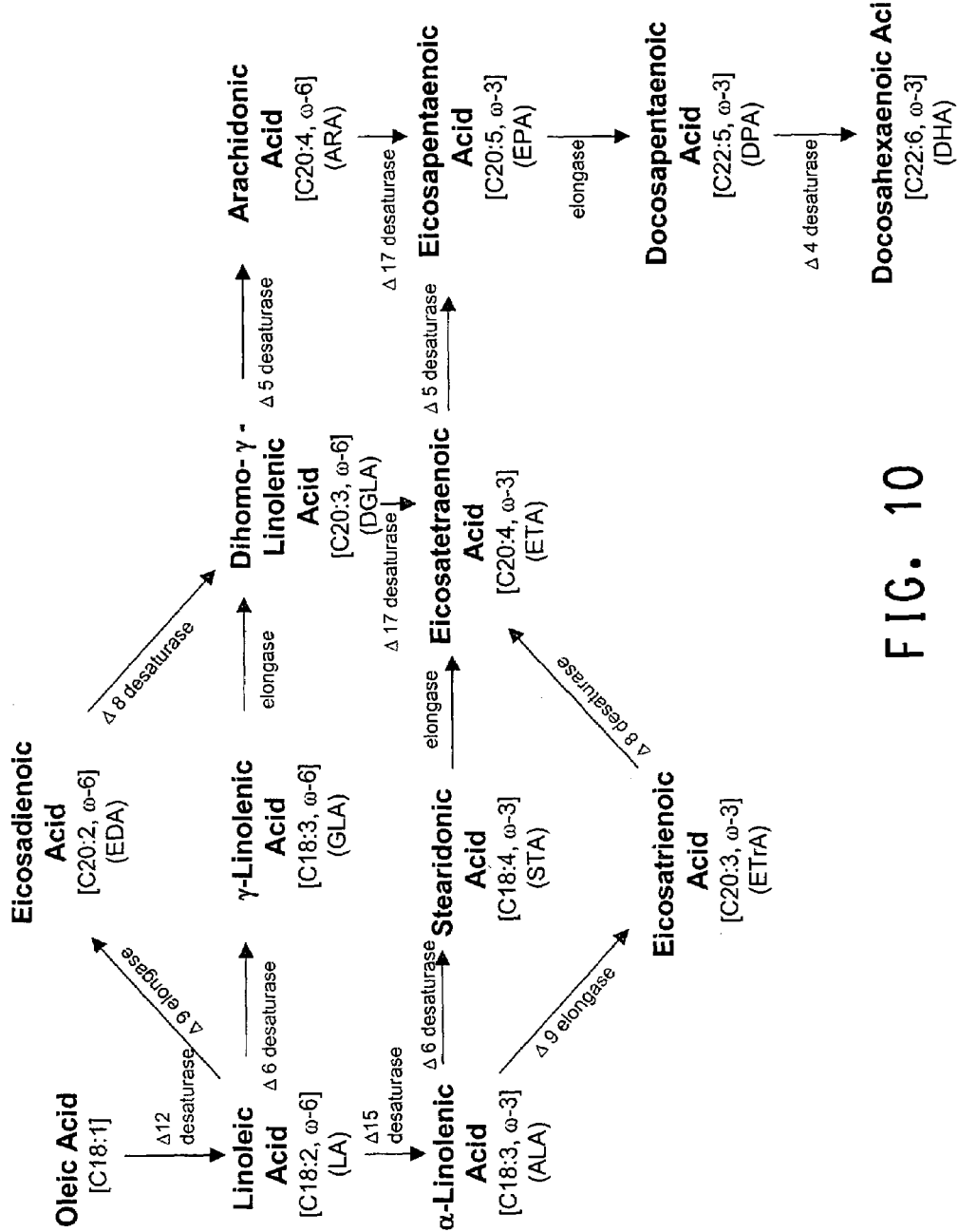

FIG. 10 illustrates the ω-3/ω-6 fatty acid biosynthetic pathway.

The invention can be more fully understood from the following detailed description and the accompanying sequence descriptions, which form a part of this application.

The following sequences comply with 37 C.F.R. §1.821–1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1–5, 10–13, 17–21, 25–27, 30, 33, 46, 49, 52, 55, 61 and 64–71 correspond to ORFs (i.e., encoding genes or proteins), promoters and terminators, as identified in Table 1.

TABLE 1

Summary Of Nucleotide And Protein SEQ ID Numbers

| Description | Nucleotide SEQ ID NO | Protein SEQ ID NO |
| --- | --- | --- |
| *Saccharomyces cerevisiae* FBA1 (GenBank Accession No. NP_012863) | — | 1 (359 AA) |
| *Schizosaccharomyces pombe* FBA1 (GenBank Accession No. NP_595692) | — | 2 (358 AA) |
| *Aspergillus oryzae* FBA1 (GenBank Accession No. BAB12232) | — | 3 (362 AA) |
| *Haemophilus influenzae* FBA1 (GenBank Accession No. NP_438682) | — | 4 (359 AA) |
| *Pasteurella multocida* FBA1 (GenBank Accession No. NP_246800) | — | 5 (359 AA) |
| *Kluyveromyces lactis* fba1 (GenBank Accession No. CAC29023) | — | 12 (361 AA) |

TABLE 1-continued

Summary Of Nucleotide And Protein SEQ ID Numbers

| Description | Nucleotide SEQ ID NO | Protein SEQ ID NO |
|---|---|---|
| *Paracoccidiodes brasiliensis* fba1 (GenBank Accession No. AAL34519) | — | 13 (360 AA) |
| *Yarrowia lipolytica* fba1 gene | 20 (531 bp) | 21 (177 AA) |
| *Yarrowia lipolytica* fba1 gene-internal portion | 10 (436 bp) | 11 (145 AA) |
| *Yarrowia lipolytica* fba1 gene-1st round genome walking product | 17 (857 bp) | — |
| *Yarrowia lipolytica* fba1 gene-5'-upstream portion of 1st round genome walking product | 18 (520 bp) | — |
| *Yarrowia lipolytica* fba1 gene-contig assembly of SEQ ID NOs: 10 and 17 | 19 (1153 bp) | — |
| *Yarrowia lipolytica* fba1 gene-2nd round genome walking product | 25 (1152 bp) | — |
| *Yarrowia lipolytica* fba1 gene-contig assembly of SEQ ID NOs: 10, 17 and 25 | 26 (2177 bp) | — |
| *Yarrowia lipolytica* fba1 gene-5' upstream portion | 27 (1542 bp) | — |
| *Yarrowia lipolytica* TEF promoter | 30 (426 bp) | — |
| *Yarrowia lipolytica* XPR2 terminator | 33 (173 bp) | — |
| *Yarrowia lipolytica* FBA promoter | 27 (1542 bp) | — |
| *Yarrowia lipolytica* FBAIN promoter | 46 (995 bp) | — |
| *Yarrowia lipolytica* FBAINm promoter | 72 (924 bp) | — |
| *Yarrowia lipolytica* GPD promoter | 49 (966 bp) | — |
| *Yarrowia lipolytica* GPM promoter | 52 (843 bp) | — |
| *Yarrowia lipolytica* fba1 intron | 55 (102 bp) | — |
| chimeric GPM::fba1 intron (GPM::FBAIN) promoter | 61 (1020 bp) | — |
| Synthetic high affinity elongase gene derived from *Mortierella alpina*, codon-optimized for expression in *Y. lipolytica* | 64 (957 bp) | 65 (318 AA) |
| Synthetic Δ6 desaturase, derived from *Mortierella alpina*, codon-optimized for expression in *Y. lipolytica* | 66 (1374 bp) | 67 (457 AA) |
| *Fusarium moniliforme* Δ12 desaturase | 68 (1434 bp) | 69 (477 AA) |
| Synthetic elongase gene derived from *Thraustochytrium aureum*, codon-optimized for expression in *Y. lipolytica* | 70 (819 bp) | 71 (272 AA) |

SEQ ID NOs:6 and 7 correspond to conserved amino acid regions of the FBA1 protein.

SEQ ID NOs:8 and 9 correspond to the degenerate primers YL214 and YL216, respectively, used for isolating a portion of coding region of the *Yarrowia lipolytica* fba1 gene.

SEQ ID NOs:14–16 and 22–24 are the oligonucleotides YL217, YL218, YL219, ODMW315, ODMW316 and ODMW317, respectively, used for genome-walking.

SEQ ID NOs:28 and 29 are the oligonucleotides YL33 and YL34, respectively, used for amplifying the reporter gene GUS.

SEQ ID NOs:31 and 32 are the oligonucleotides TEF5' and TEF3', respectively, used to isolate the TEF promoter.

SEQ ID NOs:34 and 35 are the oligonucleotides XPR5' and XPR3', respectively, used to isolate the XPR2 transcriptional terminator.

SEQ ID NOs:36–43 are the oligonucleotides YL1, YL2, YL3, YL4, YL23, YL24, YL9 and YL10, respectively, used for site-directed mutagenesis during construction of the pY5–10 plasmid.

SEQ ID NOs:44 and 45 are the oligonucleotides ODMW314 and YL341, respectively, used to amplify the FBA promoter region.

SEQ ID NOs:47 and 48 are the oligonucleotides ODMW320 and ODMW341, respectively, used to amplify the FBAIN promoter region.

SEQ ID NOs:50 and 51 are the oligonucleotides YL211 and YL212, respectively, used to amplify the putative GPD promoter.

SEQ ID NOs:53 and 54 are the oligonucleotides YL203 and YL204, respectively, used to amplify the putative GPM promoter.

SEQ ID NO:56 is the consensus sequence around the translation initiation codon in *Yarrowia lipolytica*.

SEQ ID NOs:57–60 are the oligonucleotides YL-URA-16F, YL-URA-78R, GUS-767F and GUS-891R, respectively, used for Real Time PCR analysis.

SEQ ID NOs:62 and 63 correspond to plasmids pY5–30 and pKUNF12T6E, respectively.

DETAILED DESCRIPTION OF THE INVENTION

In accordance with the subject invention, Applicants describe the isolation and characterization of a gene encoding fructose-bisphosphate aldolase (FBA1) from an oleaginous yeast, *Yarrowia lipolytica*, as well as the regulatory sequences associated with this fba1 gene. The promoter region ("FBA"), the promoter region plus the 5' portion of the coding sequence comprising an intron ("FBAIN"), a modified version of FBAIN known as "FBAINm", the fba1 intron and an enhancer within the fba1 intron are all useful for genetic engineering in *Y. lipolytica* and other yeast for the production of heterologous polypeptides.

Preferred heterologous polypeptides of the present invention are those that are involved in the synthesis of microbial oils and particularly polyunsaturated fatty acids (PUFAs). PUFAs, or derivatives thereof, made by the methodology disclosed herein can be used in many applications. For example, the PUFAs can be used as dietary substitutes, or supplements, particularly infant formulas, for patients undergoing intravenous feeding or for preventing or treating malnutrition. Alternatively, the purified PUFAs (or derivatives thereof may be incorporated into cooking oils, fats or margarines formulated so that in normal use the recipient would receive the desired amount for dietary supplementation. The PUFAs may also be incorporated into infant formulas, nutritional supplements or other food products, and may find use as anti-inflammatory or cholesterol lowering agents. Optionally, the compositions may be used for pharmaceutical use (human or veterinary). In this case, the PUFAs are generally administered orally but can be administered by any route by which they may be successfully absorbed, e.g., parenterally (e.g., subcutaneously, intramuscularly or intravenously), rectally, vaginally or topically (e.g., as a skin ointment or lotion).

Thus, the present invention advances the art by providing methods for the expression of a coding region of interest in a transformed yeast comprising: a) providing a transformed yeast cell having a chimeric gene comprising (i) a regulatory sequence of a fructose-bisphosphate aldolase (fba1) gene, wherein the regulatory sequence is a FBA promoter region, a FBA promoter region plus a portion of 5' coding region comprising an intron of a fba1 gene (FBAIN), a modified FBAIN promoter region (FBAINm) or a chimeric promoter comprising the fba1 intron or fba1 enhancer therein; and (ii) a coding region of interest expressible in the host cell, wherein the regulatory sequence is operably linked to the coding region of interest; and b) growing the transformed yeast cell of step (a) in the presence of a fermentable carbon source, wherein the chimeric gene is expressed and the expression product is optionally isolated from the cultivation medium. In preferred embodiments, the regulatory sequence comprises all or a portion of a sequence selected from the group consisting of SEQ ID NOs:17, 18, 19, 20, 25, 26, 27, 46, 55 and 72.

Definitions

In this disclosure, a number of terms and abbreviations are used. The following definitions are provided.

"Fructose-bisphosphate aldolase" is abbreviated FBA1.

"Glyceraldehyde-3-phosphate dehydrogenase" is abbreviated GPD.

"Phosphoglycerate mutase" is abbreviated GPM.

"Open reading frame" is abbreviated ORF.

"Polymerase chain reaction" is abbreviated PCR.

"Polyunsaturated fatty acid(s)" is abbreviated PUFA(s).

The term "oleaginous" refers to those organisms that tend to store their energy source in the form of lipid (Weete, In: Fungal Lipid Biochemistry, $2^{nd}$ ed., Plenum, 1980). These include oilseed plants (e.g., soybean, corn, safflower, sunflower, canola, rapeseed, flax, maize and primrose) and microorganisms (e.g., Thraustochytrium sp., Schizochytrium sp., Mortierella sp. and certain oleaginous yeast).

The term "oleaginous yeast" refers to those microorganisms classified as yeasts that can make oil. Generally, the cellular oil or triacylglycerol content of oleaginous microorganisms follows a sigmoid curve, wherein the concentration of lipid increases until it reaches a maximum at the late logarithmic or early stationary growth phase and then gradually decreases during the late stationary and death phases (Yongmanitchai and Ward, Appl. Environ. Microbiol. 57:419–25 (1991)). It is not uncommon for oleaginous microorganisms to accumulate in excess of about 25% of their dry cell weight as oil. Examples of oleaginous yeast include, but are no means limited to, the following genera: Yarrowia, Candida, Rhodotorula, Rhodosporidium, Cryptococcus, Trichosporon and Lipomyces.

The term "fermentable carbon source" will refer to a carbon source that a microorganism will metabolize to derive energy. Typical carbon sources for use in the present invention include, but are not limited to: monosaccharides, oligosaccharides, polysaccharides, alkanes, fatty acids, esters of fatty acids, monoglycerides, diglycerides, triglycerides, carbon dioxide, methanol, formaldehyde, formate and carbon-containing amines.

The term "FBA1" refers to a fructose-bisphosphate aldolase enzyme (E.C. 4.1.2.13) encoded by the fba1 gene and which converts D-fructose 1,6-bisphosphate into glycerone phosphate and D-glyceraldehyde 3-phosphate. SEQ ID NO:26 comprises the partial coding region of the fba1 gene isolated from Yarrowia lipolytica; specifically, the sequence lacks ~184 amino acids that encode the C-terminus of the gene (based on alignment with other known fba1 sequences).

The term "FBA promoter" or "FBA promoter region" refers to the 5' upstream untranslated region in front of the 'ATG' translation initiation codon of fba1 and that is necessary for expression. Examples of suitable FBA promoter regions are provided as SEQ ID NOs:18 and 27, but these are not intended to be limiting in nature. One skilled in the art will recognize that since the exact boundaries of this particular regulatory sequence has not been completely defined, DNA fragments of increased or diminished length may have identical promoter activity.

The term "FBAIN promoter" or "FBAIN promoter region" refers to the 5' upstream untranslated region in front of the 'ATG' translation initiation codon and that is necessary for expression, plus a portion of 5' coding region comprising an intron of the fba1 gene. An example of a suitable FBAIN promoter region is provided as SEQ ID NO:46, but this is not intended to be limiting in nature. Again, one will recognize that since the exact boundaries of the FBAIN promoter sequence has not been completely defined, DNA fragments of increased or diminished length may have identical promoter activity.

The term "FBAINm promoter" or "FBAINm promoter region" refers to a modified version of the FBAIN promoter (supra), wherein FBAINm has a 52 bp deletion between the ATG translation initiation codon and the intron of the FBAIN promoter (thereby including only 22 amino acids of the N-terminus) and a new translation consensus motif after the intron. Furthermore, while the FBAIN promoter generates a fusion protein when fused with the coding region of a gene to be expressed, the FBAINm promoter does not generate such a fusion protein. An example of a suitable FBAINm promoter region is provided as SEQ ID NO:72.

The term "fba1 intron" or "intron of the fba1 gene" refers to the intron as defined by SEQ ID NO:55.

The term "GPD" refers to a glyceraldehyde-3-phosphate dehydrogenase enzyme (E.C. 1.2.1.12) encoded by the gpd gene and which converts D-glyceraldehyde 3-phosphate to 3-phospho-D-glyceroyl phosphate during glycolysis. The term "GPD promoter" or "GPD promoter region" refers to the 5' upstream untranslated region in front of the 'ATG' translation initiation codon of GPD and that is necessary for expression. One example of a suitable GPD promoter region is provided as SEQ ID NO:49, but this is not intended to be limiting in nature (see co-pending U.S. patent application Ser. No. 10/869,630 for additional details).

The term "GPM" refers to a phosphoglycerate mutase enzyme (EC 5.4.2.1) encoded by the gpm gene and which is responsible for the interconversion of 3-phosphoglycerate and 2-phosphoglycerate during glycolysis. The term "GPM promoter" or "GPM promoter region" refers to the 5' upstream untranslated region in front of the 'ATG' translation initiation codon of GPM and that is necessary for expression. One example of a suitable GPM promoter region is provided as SEQ ID NO:52, but this is not intended to be limiting in nature (see co-pending U.S. patent application Ser. No. 10/869,630 for additional details).

The term "promoter activity" will refer to an assessment of the transcriptional efficiency of a promoter. This may, for instance, be determined directly by measurement of the amount of mRNA transcription from the promoter (e.g., by Northern blotting or primer extension methods) or indirectly by measuring the amount of gene product expressed from the promoter.

As used herein, the terms "isolated nucleic acid molecule" and "isolated nucleic acid fragment" are used interchangeably and mean a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

A nucleic acid molecule is "hybridizable" to another nucleic acid molecule, such as a cDNA, genomic DNA, or RNA molecule, when a single-stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, $2^{nd}$ ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washed with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50–9.51). For hybridizations with shorter nucleic acids, i.e., oligonucleotides, the position of mismatches becomes more important, and the length of the oligonucleotide determines its specificity (see Sambrook et al., supra, 11.7–11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.* 215:403–410 (1993)). In general, a sequence of ten or more contiguous amino acids or thirty or more nucleotides is necessary in order to identify putatively a polypeptide or nucleic acid sequence as homologous to a known protein or gene. Moreover, with respect to nucleotide sequences, gene-specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid molecule comprising the primers. Accordingly, a "substantial portion" of a nucleotide sequence comprises enough of the sequence to specifically identify and/or isolate a nucleic acid molecule comprising the sequence.

The instant specification teaches partial or complete amino acid and nucleotide sequences encoding one or more particular microbial proteins and regulatory sequences. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "oligonucleotide" refers to a nucleic acid, generally of at least 18 nucleotides, that is hybridizable to a genomic DNA molecule, a cDNA molecule, or an mRNA molecule. In one embodiment, a labeled oligonucleotide can be used as a "probe" to detect the presence of a nucleic acid according to the invention. Thus, the term "probe" refers to a single-stranded nucleic acid molecule that can base pair with a complementary single-stranded target nucleic acid to form a double-stranded molecule. The term "label" will refer to any conventional molecule which can be readily attached to mRNA or DNA and which can produce a detectable signal, the intensity of which indicates the relative amount of hybridization of the labeled probe to the DNA fragment.

The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid molecules that are complementary to the complete sequences as reported in the accompanying Sequence Listing, as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences is performed using the Clustal method of alignment (Higgins and Sharp. *CABIOS.* 5:151–153 (1989)) with default parameters (GAP PENALTY=10, GAP LENGTH PENALTY=10). Default parameters for pairwise alignments using the Clustal method are: KTUPLE 1, GAP PENALTY=3, WINDOW=5 and DIAGONALS SAVED=5.

Suitable nucleic acid molecules (isolated polynucleotides of the present invention) encode polypeptides that are at least about 70% identical, preferably at least about 75% identical, and more preferably at least about 80% identical to the amino acid sequences reported herein. Preferred nucleic acid molecules encode amino acid sequences that are about 85% identical to the amino acid sequences reported herein. More preferred nucleic acid molecules encode amino acid sequences that are at least about 90% identical to the amino acid sequences reported herein. Most preferred are nucleic acid molecules that encode amino acid sequences that are at least about 95% identical to the amino acid sequences reported herein. Suitable nucleic acid molecules not only have the above homologies but typically encode a polypeptide having at least 50 amino acids, preferably at least 100 amino acids, more preferably at least 150 amino acids, still more preferably at least 200 amino acids, and most preferably at least 250 amino acids.

Likewise, suitable promoter regions (isolated polynucleotides of the present invention) encode promoter regions that are at least about 70% identical, preferably at least about 75% identical, and more preferably at least about 80% identical to the nucleotide sequences reported herein. Preferred nucleic acid molecules are about 85% identical to the nucleotide sequences reported herein, more preferred nucleic acid molecules are at least about 90% identical, and most preferred are nucleic acid molecules at least about 95% identical to the nucleotide sequences reported herein. Suitable promoter regions not only have the above homologies but typically are at least 50 nucleotides in length, more preferably at least 100 nucleotides in length, more preferably at least 250 nucleotides in length, and more preferably at least 500 nucleotides in length.

"Codon degeneracy" refers to the nature in the genetic code permitting variation of the nucleotide sequence without affecting the amino acid sequence of an encoded polypeptide. Accordingly, the instant invention relates to any nucleic acid molecule that encodes all or a substantial portion of the amino acid sequence encoding the instant microbial polypeptide as set forth in SEQ ID NO:21. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Chemically synthesized", as related to a sequence of DNA, means that the component nucleotides were assembled in vitro. Manual chemical synthesis of DNA may be accomplished using well-established procedures; or, automated chemical synthesis can be performed using one of a number of commercially available machines. "Synthetic genes" can be assembled from oligonucleotide building blocks that are chemically synthesized using procedures known to those skilled in the art. These building blocks are ligated and annealed to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available.

"Gene" refers to a nucleic acid molecule that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. Chimeric genes of the present invention will typically comprise a regulatory sequence of the fba1 gene operably linked to a coding region of interest. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence that codes for a specific amino acid sequence.

"Suitable regulatory sequences" refer to transcriptional and translational "control" nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. The term "promoter region" as used herein means that region of a nucleic acid molecule that contains a functional promoter. The promoter region may comprise extraneous nucleic acid elements or fragments however contain all of the promoter in question. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "mutant promoter" is defined herein as a promoter having a nucleotide sequence comprising a substitution, deletion, and/or insertion of one or more nucleotides relative to the parent promoter, wherein the mutant promoter has more or less promoter activity than the corresponding parent promoter. The term "mutant promoter" will encompass natural variants and in vitro generated variants obtained using methods well known in the art (e.g., classical mutagenesis, site-directed mutagenesis and "DNA shuffling").

The term "introns" refers to sequences of non-coding DNA found in gene sequences (either in the coding region, 5' non-coding region, or 3' non-coding region) in most eukaryotes. Their full function is not known; however, some enhancers are located in introns (Giacopelli F. et al., *Gene Expr.* 11: 95–104 (2003)). These intron sequences are transcribed, but removed from within the pre-mRNA transcript before the mRNA is translated into a protein. This process of intron removal occurs by self-splicing of the sequences (exons) on either side of the intron.

The term "regulatory sequence" refers to those portions of a gene that service to regulate the expression, transcription or translation of the gene. Common regulatory sequences are initiation control regions, promoters and enhancers, although the term is not so limited.

The term "enhancer" refers to a cis-regulatory sequence that can elevate levels of transcription from an adjacent eukaryotic promoter, thereby increasing transcription of the gene. Enhancers can act on promoters over many tens of kilobases of DNA and can be 5' or 3' to the promoter they regulate. Enhancers can also be located within introns.

The term "3' non-coding sequences" or "transcription terminator" refers to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and that can be translated into protein by the cell. "cDNA" refers to a double-stranded DNA that is complementary to, and derived from, mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 99/28508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated and yet has an effect on cellular processes.

The term "operably linked" refers to the association of nucleic acid sequences on a single nucleic acid molecule so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from a coding sequence. Expression may also refer to translation of mRNA into a polypeptide.

"Transformation" refers to the transfer of a nucleic acid molecule into a host organism, resulting in genetically stable inheritance. The nucleic acid molecule may be a plasmid that replicates autonomously, for example; or, it may integrate into the genome of the host organism. Host organisms containing the transformed nucleic acid fragments are referred to as "transgenic" or "recombinant" or "transformed" organisms.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.* 215: 403–410 (1990)); 3.) DNASTAR (DNASTAR, Inc. Madison, Wis.); and 4.) the FASTA program incorporating the Smith-Waterman algorithm (W. R. Pearson, *Comput. Methods Genome Res.*, [Proc. Int. Symp.] (1994), Meeting Date 1992, 111–20. Suhai, Sandor, Ed. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

Standard recombinant DNA and molecular cloning techniques used herein are well known in the art and are described by Sambrook, J., Fritsch, E. F. and Maniatis, T., *Molecular Cloning: A Laboratory Manual*, 2nd ed., Cold Spring Harbor Laboratory: Cold Spring Harbor, N.Y. (1989) (hereinafter "Maniatis"); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience (1987).

Identification of the fba1 Gene in *Yarrowia lipolytica*

The present invention identifies the partial sequence of a *Yarrowia lipolytica* fructose-bisphosphate aldolase gene (fba1) and the corresponding encoded protein (FBA1) (wherein ~184 amino acids of the C-terminus of the protein are not disclosed herein).

Comparison of the deduced amino acid sequence (SED ID NO:21) from the partial sequence of the fba1 gene (i.e., as set forth in SEQ ID NO:26) to public databases reveals that the most similar known sequences are about 81% identical to the amino acid sequence of FBA1 reported herein over a length of 177 amino acids using a Smith-Waterman alignment algorithm (W. R. Pearson, *Comput Methods Genome Res.*, [Proc. Int. Symp.] Meeting Date 1992, 111-20. Suhai, Sandor, Ed., Plenum: New York, N.Y. (1994)). Preferred amino acid fragments are at least about 70%–80% identical to the sequences herein, where those sequences that are 85%–90% identical are particularly suitable and those sequences that are about 95% identical are most preferred. Similarly, preferred FBA1 encoding nucleic acid sequences corresponding to the instant ORF are those encoding partial proteins and which are at least about 70%–80% identical to the nucleic acid sequence of fba1 reported herein, where those sequences that are 85%–90% identical are particularly suitable and those sequences that are about 95% identical are most preferred.

Identification of Regulatory Sequences of the fba1 Gene in *Yarrowia lipolytica* and Relative Quantitation of their Activity The present invention also identifies putative promoter regions, an intron and an enhancer that naturally regulate the expression of the fba1 gene in *Yarrowia lipolytica*. These regulatory sequences have been identified as useful for driving expression of any suitable coding region of interest in a transformed yeast cell.

In the context of the present invention, a promoter useful in an oleaginous yeast should meet the following criteria:
 1.) Strength. A strong yeast promoter is a necessary premise for a high expression level, and the low copy number of the ars18 (Fournier, P. et al. *Yeast* 7:25–36 (1991)) based expression vectors or chimeric genes integrated into the genome makes this demand even more important when *Yarrowia lipolytica* is used as the host organism.
 2.) Activity in a medium suitable for expression of the coding region of interest, and high enzymatic activity of that coding region of interest.
 3.) pH Tolerance. If the coding region of interest is known to be produced only in e.g., an acidic environment, then the promoter operably linked to said coding region of interest must function at the appropriate pH. pH tolerance is of course limited by the tolerance of the host organism.
 4.) Inducibility. A tightly regulated yeast promoter makes it possible to separate the growth stage from the expression stage, thereby enabling expression of products that are known to inhibit cell growth.
 5.) Activity in the stationary phase of growth in oleaginous yeast hosts, to thereby enable accumulation of PUFAs.

Additionally, it is preferable for novel yeast promoters to possess differences in activity with respect to the known *Yarrowia lipolytica* TEF (U.S. Pat. No. 6,265,185), XPR2 (U.S. Pat. No. 4,937,189; EP220864; EP832258), GPD (co-pending U.S. patent application Ser. No. 10/869,630) and GPM (co-pending U.S. patent application Ser. No. 10/869,630) promoters. A comparative study of the known TEF, GPD and GPM promoters and the FBA and FBAIN promoters of the instant invention is provided in Examples 7 and 8. It is shown that the yeast promoters of the instant invention have improved activity compared to the TEF, GPD and GPM promoters. The promoter region (FBA) of the instant fba1 gene, and the promoter region plus the 5' portion of coding region comprising an intron (FBAIN) of the instant fba1 gene, or portions of FBA or FBAIN, are contained within several nucleic acid molecules (specifically, SEQ ID NOs:17, 18, 19, 26, 27 and 46).

In one embodiment, the FBA promoter will comprise nucleotides −500 to +1 of SEQ ID NO:27 (wherein the 'A' position of the 'ATG' translation initiation codon is designated as +1), thereby permitting relatively strong promoter activity; in alternate embodiments, the −100 to +1 region of SEQ ID NO:27 should be sufficient for basal activity of the promoter. The promoter regions of the invention may also comprise additional nucleotides to those specified above. For example, the FBAIN promoter (i.e., SEQ ID NO:46) includes the intron of the instant fba1 gene, which is located at position +64 to +165 within the fba1 gene (i.e., SEQ ID NO:55). Similarly, the FBAINm promoter (i.e., SEQ ID NO:72) is a modified version of the FBAIN promoter, wherein FBAINm has a 52 bp deletion between the ATG translation initiation codon and the intron of the FBAIN promoter (thereby including only 22 amino acids of the N-terminus) and a new translation consensus motif after the intron. Furthermore, while the FBAIN promoter generates a fusion protein when fused with the coding region of a gene to be expressed, the FBAINm promoter does not generate such a fusion protein. On the basis of the work presented herein and the knowledge of one of skill in the art, it will be obvious that various promoter sequences of the invention may be constructed on the basis of the DNA sequence presented as SEQ ID NO:26 (e.g., SEQ ID NO:46, corresponding to FBAIN, is a subsequence thereof. It should be recognized that promoter fragments of various diminishing lengths may have identical promoter activity, since the exact boundaries of the regulatory sequences have not been completely defined.

In alternate embodiments, it was demonstrated herein that the fba1 intron (i.e., SEQ ID NO:55) or the enhancer within the intron of the fba1 gene may be used to enhance the activity of a promoter. Specifically, FBAIN demonstrated enhanced expression of a coding region relative to the FBA promoter (Examples 7, and 8). Upon further analysis, it was determined herein that the fba1 intron comprises an enhancer that is useful for increasing the transcription from an adjacent eukaryotic promoter, wherein the adjacent promoter can be the native FBA or FBAIN promoter or a chimeric promoter (e.g., a GPM promoter demonstrated increased activity when used in conjunction with the fba1 intron; see Example 9).

Although it may be useful to indirectly quantitate promoter activity based on reporter gene expression (i.e., the *E. coli* gene encoding β-glucuronidase (GUS)), it may sometimes be useful to quantify promoter activity using more quantitative means. One suitable method is the use of real-time PCR (for a general review of real-time PCR applications, see Ginzinger, D. J., *Experimental Hematology*, 30:503–512 (2002)). Real-time PCR is based on the detection and quantitation of a fluorescent reporter. This signal increases in direct proportion to the amount of PCR product in a reaction. By recording the amount of fluorescence emission at each cycle, it is possible to monitor the PCR reaction during exponential phase where the first significant increase in the amount of PCR product correlates to the initial amount of target template. There are two general methods for the quantitative detection of the amplicon: (1) use of fluorescent probes; or (2) use of DNA-binding agents (e.g., SYBR-green I, ethidium bromide). For relative gene expression comparisons, it is necessary to use an endogenous control as an internal reference (e.g., a chromosomally encoded 16S rRNA gene), thereby allowing one to normalize for differences in the amount of total DNA added to each real-time PCR reaction. Specific methods for real-time PCR are well documented in the art. See, for example, the Real Time PCR Special Issue (*Methods*, 25(4): 383–481 (2001)).

Following a real-time PCR reaction, the recorded fluorescence intensity is used to quantitate the amount of template by use of: 1.) an absolute standard method (wherein a known amount of standard such as in vitro translated RNA (cRNA) is used); 2.) a relative standard method (wherein known amounts of the target nucleic acid are included in the assay design in each run); or 3.) a comparative $C_T$ method ($\Delta\Delta C_T$) for relative quantitation of gene expression (wherein the relative amount of the target sequence is compared to any of the reference values chosen and the result is given as relative to the reference value).

The comparative $C_T$ method requires one to first determine the difference ($\Delta C_T$) between the $C_T$ values of the target and the normalizer, wherein: $\Delta C_T = C_T$ (target)$-C_T$ (normalizer). This value is calculated for each sample to be quantitated and one sample must be selected as the reference against which each comparison is made. The comparative $\Delta\Delta C_T$ calculation involves finding the difference between each sample's $\Delta C_T$ and the baseline's $\Delta C_T$, and then transforming these values into absolute values according to the formula $2^{-\Delta\Delta C_T}$.

In one aspect of the invention, it was desirable to compare the activity of various *Yarrowia lipolytica* promoters, to facilitate a determination of each promoter's strength for use in future applications wherein a suite of promoters would be necessary to construct chimeric genes useful for the production of ω-6 and ω-3 fatty acids.

Generation of Mutants Derived from the fba1 Gene and Putative Promoter Regions

In alternate embodiments mutant promoters may be constructed, wherein the DNA sequence of the promoter has one or more nucleotide substitutions (i.e., deletions, insertions, substitutions, or addition of one or more nucleotides in the sequence) which do not affect (in particular impair) the yeast promoter activity. Regions that can be modified without significantly affecting the yeast promoter activity can be identified by deletion studies. A mutant promoter of the present invention has at least about 20%, preferably at least about 40%, more preferably at least about 60%, more preferably at least about 80%, more preferably at least about 90%, more preferably at least about 100%, more preferably at least about 200%, more preferably at least about 300% and more preferably at least about 400% of the promoter activity of the FBA promoter region and/or the FBAIN promoter region and/or the FBAINm promoter region described herein. Examples of the FBA, FBAIN and FBAINm promoter regions are the DNA sequences set forth in SEQ ID NO:18, SEQ ID NO:46 and SEQ ID NO:72, respectively.

Methods for mutagenesis are well known in the art and suitable for the generation of mutant promoters. For example, in vitro mutagenesis and selection, PCR based random mutagenesis, site-directed mutagenesis, or other means can be employed to obtain mutations of the naturally occurring promoters and genes of the instant invention. This would permit production of a putative promoter having a more desirable level of promoter activity in the host cell, or production of a polypeptide having more desirable physical and kinetic parameters for function in the host cell.

If desired, the regions of a nucleotide of interest important for promoter or enzymatic activity, respectively, can be determined through routine mutagenesis, expression of the resulting mutant promoters or polypeptides and determination of their activities. Mutants may include deletions, insertions and point mutations, or combinations thereof. A typical functional analysis begins with deletion mutagenesis to determine either: 1.) the minimum portion of the putative promoter necessary for activity; or 2.) the N- and C-terminal limits of the protein necessary for function. Subsequently, internal deletions, insertions or point mutants are made to further determine regions necessary for function. Other techniques such as cassette mutagenesis or total synthesis also can be used.

Deletion mutagenesis of a coding sequence is accomplished, for example, by using exonucleases to sequentially remove the 5' or 3' coding regions. Kits are available for such techniques. After deletion, the coding region is completed by ligating oligonucleotides containing start or stop codons to the deleted coding region after 5' or 3' deletion, respectively. Alternatively, oligonucleotides encoding start or stop codons are inserted into the coding region by a variety of methods including site-directed mutagenesis, mutagenic PCR or by ligation onto DNA digested at existing restriction sites.

Internal deletions in a putative promoter region or within a coding sequence can similarly be made through a variety of methods including the use of existing restriction sites in the DNA, by use of mutagenic primers via site-directed mutagenesis or mutagenic PCR. Insertions are made through methods such as linker-scanning mutagenesis, site-directed mutagenesis or mutagenic PCR, while point mutations are made through techniques such as site-directed mutagenesis or mutagenic PCR.

Chemical mutagenesis also can be used for identifying regions of a putative promoter region or polypeptide important for activity. A mutated construct is expressed, and the ability of the resulting altered promoter or protein, respectively, is assayed. Such structure-function analysis can determine which regions may be deleted, which regions tolerate insertions, and which point mutations allow the mutant promoter or protein to function in substantially the same way as the native promoter or protein. All such mutant promoters and nucleotide sequences encoding polypeptides that are derived from the instant promoters and genes described herein are within the scope of the present invention.

Isolation of Homologs to the fba1 Gene and Putative Promoter Regions

It will be appreciated by a person of skill in the art that the promoter regions and genes of the present invention have homologs in a variety of yeast species; and, the use of the promoters and genes for heterologous gene expression are not limited to those promoters and genes derived from *Yarrowia lipolytica*, but extend to homologs in other yeast species. For example, the invention encompasses homologs derived from oleaginous genera including, but not limited to: *Yarrowia, Candida, Rhodotorula, Rhodosporidium, Cryptococcus, Trichosporon* and *Lipomyces*; examples of preferred species within these genera include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus* and *R. graminis*.

Homology typically is measured using sequence analysis software, wherein the term "sequence analysis software" refers to any computer algorithm or software program (commercially available or independently developed) that is useful for the analysis of nucleotide or amino acid sequences. In general, such computer software matches similar sequences by assigning degrees of homology to various substitutions, deletions and other modifications.

As is well known in the art, isolation of homologous promoter regions or genes using sequence-dependent protocols is readily possible using various techniques. Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Acad. Sci. USA* 82:1074 (1985); or strand displacement amplification (SDA), Walker, et al., *Proc. Natl. Acad. Sci. U.S.A.*, 89:392 (1992)]; and 3.) methods of library construction and screening by complementation.

For example, putative promoter regions or genes encoding similar proteins or polypeptides to those of the instant invention could be isolated directly by using all or a portion of the instant nucleic acid molecules as DNA hybridization probes to screen libraries from any desired microbe using methodology well known to those skilled in the art. Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation, or end-labeling techniques), or RNA probes using available in vitro transcription systems. In addition, specific primers can be designed and used to amplify a part of (or full-length of) the instant sequences.

The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotide as specific hybridization probes in the Diagnosis of Genetic Disorders", in *Human Genetic Diseases: A Practical Approach*, K. E. Davis (Ed.), (1986) pp 33–50 IRL: Herndon, VA; and Rychlik, W., In *Methods in Molecular Biology*, White, B. A. (Ed.), (1993) Vol. 15, pp 31–39, PCR Protocols: Current Methods and Applications. Humania: Totowa, N.J.).

Generally two short segments of the instant sequences may be used in polymerase chain reaction protocols to amplify longer nucleic acid molecules encoding homologous polynucleotides from DNA or RNA. The polymerase chain reaction may also be performed on a library of cloned nucleic acid molecules wherein the sequence of one primer is derived from the instant nucleic acid molecules, and the sequence of the other primer takes advantage of the presence of the polyadenylic acid tracts to the 3' end of the mRNA precursor encoding microbial genes.

Alternatively, the instant sequences may be employed as hybridization reagents for the identification of homologs. The basic components of a nucleic acid hybridization test include a probe, a sample suspected of containing the nucleotide sequence of interest, and a specific hybridization method. Probes of the present invention are typically single-stranded nucleic acid sequences that are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143–5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide and cesium trifluoroacetate, among others. Typically, the chaotropic agent will be present at a final concentration of about 3 M. If desired, one can add formamide to the hybridization mixture, typically 30–50% (v/v).

Various hybridization solutions can be employed. Typically, these comprise from about 20 to 60% volume, preferably 30%, of a polar organic solvent. A common hybridization solution employs about 30–50% v/v formamide, about 0.15 to 1 M sodium chloride, about 0.05 to 0.1 M buffers (e.g., sodium citrate, Tris-HCl, PIPES or HEPES (pH range about 6–9)), about 0.05 to 0.2% detergent (e.g., sodium dodecylsulfate), or between 0.5–20 mM EDTA, FICOLL (Pharmacia, Inc.) (about 300–500 kdaI), polyvinylpyrrolidone (about 250–500 kdaI) and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Recombinant Expression in Yeast

Regulatory sequences that are useful to drive expression of a coding gene of interest in the desired host cell are selected from those derived from the upstream and 5' portion of the fba1 gene; the DNA fragments set forth in SEQ ID NOs:26, 27, 46 and 72, for example, comprise promoters regions as described herein while SEQ ID NO:55 is an intron having enhancer activity. The promoter region may be identified from the upstream sequence of the fba1 gene and its homologs and isolated according to common methods (Maniatis, supra). Alternatively, it is possible to create a chimeric promoter that comprises the intron of the fba1 gene, as set forth in SEQ ID NO:55 (see, for example, SEQ ID NO:61). Once the promoter region is identified and isolated (or synthetically constructed), it may be operably linked to a coding region of interest to be expressed in a suitable expression vector. These chimeric genes may then be expressed in natural host cells and heterologous host cells, particularly in the cells of oleaginous yeast hosts. Thus, one aspect of the present invention provides a recombinant expression vector comprising a yeast promoter of the invention.

In a further aspect, the invention provides a method of expressing a coding region of interest in a transformed yeast cell, wherein a transformed cell is provided having a chimeric gene comprising: (i) a FBA. FBAIN or FBAINm promoter region; and (ii) a coding region of interest expressible in the host, wherein the FBA promoter region, FBAIN promoter region or FBAINm promoter region is operably linked to the coding region of interest; and wherein the transformed cell is grown under conditions wherein the chimeric gene is expressed. The polypeptide so produced can optionally be recovered from the culture.

In an alternate aspect, the invention provides a method of expressing a coding region of interest in a transformed yeast cell, wherein a transformed cell is provided having a chimeric gene comprising: (i) a chimeric promoter region comprising the fba1 intron (SEQ ID NO:55) or fba1 enhancer therein; and (ii) a coding region of interest expressible in the host, wherein the chimeric promoter region comprising the fba1 intron or fba1 enhancer therein is operably linked to the coding region of interest; and wherein the transformed cell is grown under conditions wherein the chimeric gene is expressed. The polypeptide so produced can optionally be recovered from the culture.

Microbial expression systems and expression vectors are well known to those skilled in the art. Any of these could be used to construct chimeric genes comprising the regulatory sequences derived from the fba1 gene for production of any specific coding region of interest suitable for expression in a desirable yeast host cell. These chimeric genes could then be introduced into appropriate microorganisms by integration via transformation to provide high-level expression of the enzymes upon induction. Alternatively, the regulatory sequences can be cloned into a plasmid that is capable of transforming and replicating itself in the preferred yeast host cell. The coding region of interest to be expressed can then be cloned downstream from the regulatory sequences. Once the recombinant host is established, gene expression can be accomplished by growing the cells under suitable conditions (infra).

Suitable Coding Regions of Interest

Useful chimeric genes will include the FBA promoter region, the FBAIN promoter region of the fba1 gene as defined herein, the FBAINm promoter region, a chimeric promoter comprising the intron or enhancer of the fba1 gene, or mutant promoters thereof, operably linked to a suitable coding region of interest to be expressed in a preferred host cell.

Coding regions of interest to be expressed in the recombinant yeast host may be either endogenous to the host or heterologous and must be compatible with the host organism. Genes encoding proteins of commercial value are particularly suitable for expression. For example, suitable coding regions of interest may include (but are not limited to) those encoding viral, bacterial, fungal, plant, insect, or vertebrate coding regions of interest, including mammalian polypeptides. Further, these coding regions of interest may be, for example, structural proteins, enzymes (e.g., oxidoreductases, transferases, hydrolyases, lyases, isomerases, ligases), or peptides. A non-limiting list includes genes encoding enzymes such as acyltransferases, aminopeptidases, amylases, carbohydrases, carboxypeptidases, catalyases, cellulases, chitinases, cutinases, cyclodextrin glycosyltransferases, deoxyribonucleases, esterases, α-galactosidases, β-glucanases, β-galactosidases, glucoamylases, α-glucosidases, β-glucosidases, invertases, laccases, lipases, mannosidases, mutanases, oxidases, pectinolytic enzymes, peroxidases, phospholipases, phytases, polyphenoloxidases, proteolytic enzymes, ribonucleases, transglutaminases and xylanases.

Preferred in the present invention in some embodiments are coding regions of the enzymes involved in the production of microbial oils, including ω-6 and ω-3 fatty acids. Many microorganisms, including algae, bacteria, molds and yeast, can synthesize PUFAs and omega fatty acids in the ordinary course of cellular metabolism. Particularly well-studied are fungi including *Schizochytrium aggregatm*, species of the genus *Thraustochytrium* and *Morteriella alpina*. Additionally, many dinoflagellates (Dinophyceaae) naturally produce high concentrations of PUFAs. As such, a variety of genes involved in oil production have been identified through genetic means and the DNA sequences of some of these genes are publicly available (e.g., see GenBank Accession No.'s AY131238, Y055118, AY055117, AF296076, AF007561, L11421, NM_031344, AF465283, AF465282, AF465281, AF110510, AF419296, AB052086, AJ250735, AF126799, AF126798, AF199596, AF226273, AF320509, AB072976, AF489588, AJ510244, AF419297, AF07879, AF067654, AB022097, AF489589.1, AY332747, MG36933, AF110509, AB020033, AAL13300, AF417244, AF161219, X86736, AF240777, AB007640, AB075526, AP002063, NP_441622, BM18302, BM02924, AAL36934, AF338466, AF438199, E11368, E11367, D83185, U90417, AF085500, AY504633, NM_069854, AF230693, AX464731, NM_119617, NM_134255, NM_134383, NM_134382, NM_068396, NM_068392, NM_070713, NM_068746 and NM_064685). Additionally, the patent literature provides many additional DNA sequences of genes (and/or details concerning several of the genes above and their methods of isolation) involved in oil production. See, for example: U.S. Pat. No. 5,968,809 (Δ6 desaturases); U.S. Pat. No. 5,972,664 and U.S. Pat. No. 6,075,183 (Δ5 desaturases); WO 91/13972 and U.S. Pat. No. 5,057,419 (Δ9 desaturases); WO 93/11245 (Δ15 desaturases); WO 94/11516, U.S. Pat. No. 5,443,974 and WO 03/099216 (Δ12 desaturases); U.S. 2003/0196217 A1 (Δ17 desaturase); WO 00/34439 (Δ8 desaturases); WO 00/12720 and U.S. 2002/0139974A1 (elongases), each of which is herein incorporated by reference in its entirety.

Components of Vectors/DNA Cassettes

Vectors or DNA cassettes useful for the transformation of suitable host cells are well known in the art. The specific choice of sequences present in the construct is dependent upon the desired expression products (supra), the nature of the host cell and the proposed means of separating transformed cells versus non-transformed cells. Typically, however, the vector or cassette contains regulatory sequences directing transcription and translation of the relevant gene(s), a selectable marker and sequences allowing autonomous replication or chromosomal integration. Suitable vectors comprise a region 5' of the gene that controls transcriptional initiation and a region 3' of the DNA fragment that controls transcriptional termination. It is most preferred when both control regions are derived from genes from the transformed host cell, although it is to be understood that such control regions need not be derived from the genes native to the specific species chosen as a production host.

Nucleotide sequences surrounding the translational initiation codon 'ATG' have been found to affect expression in yeast cells. If the desired polypeptide is poorly expressed in yeast, the nucleotide sequences of exogenous genes can be modified to include an efficient yeast translation initiation sequence motif to obtain optimal gene expression. For expression in yeast, this can be done by site-directed mutagenesis of an inefficiently expressed gene to include the favored translation initiation motif.

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Preferably, the termination region is derived from a yeast gene, particularly *Saccharomyces, Schizosaccharomyces, Candida, Yarrowia* or *Kluyveromyces*. The 3'-regions of mammalian genes encoding γ-interferon and α-2 interferon are also known to function in yeast. Termination control regions may also be derived from various genes native to the preferred hosts. Optionally, a termination site may be unnecessary; however, it is most preferred if included.

As one of skill in the art is aware, merely inserting a chimeric gene into a cloning vector does not ensure that it will be successfully expressed at the level needed. In response to needs for high expression rates, many specialized expression vectors have been created by manipulating a number of different genetic elements that control aspects of transcription, translation, protein stability, oxygen limitation and secretion from the host cell. More specifically, some of the molecular features that have been manipulated to control gene expression include: 1.) the nature of the relevant transcriptional promoter and terminator sequences; 2.) the number of copies of the cloned gene and whether the gene is plasmid-borne or integrated into the genome of the host cell; 3.) the final cellular location of the synthesized foreign protein; 4.) the efficiency of translation in the host organism; 5.) the intrinsic stability of the cloned gene protein within the host cell; and 6.) the codon usage within the cloned gene, such that its frequency approaches the frequency of preferred codon usage of the host cell. Each of these types of modifications are encompassed in the present invention, as means to further optimize expression of a chimeric gene comprising the FBA promoter region, FBAIN promoter region, the FBAINm promoter region, fba1 intron or enhancer of the fba1 gene as defined herein, or a mutant promoter thereof, operably linked to a suitable coding region of interest.

Transformation of Yeast Cells

Once an appropriate chimeric gene has been constructed that is suitable for expression in a yeast cell, it is placed in a plasmid vector capable of autonomous replication in a host cell or it is directly integrated into the genome of the host cell. Integration of expression cassettes can occur randomly within the host genome or can be targeted through the use of constructs containing regions of homology with the host genome sufficient to target recombination with the host locus. Where constructs are targeted to an endogenous locus, all or some of the transcriptional and translational regulatory sequences can be provided by the endogenous locus.

Where two or more genes are expressed from separate replicating vectors, it is desirable that each vector has a different means of selection and should lack homology to the other constructs to maintain stable expression and prevent reassortment of elements among constructs. Judicious choice of regulatory regions, selection means and method of propagation of the introduced construct can be experimentally determined so that all introduced genes are expressed at the necessary levels to provide for synthesis of the desired products.

Constructs comprising a coding region of interest may be introduced into a host cell by any standard technique. These techniques include transformation (e.g., lithium acetate transformation [*Methods in Enzymology*, 194:186–187 (1991)]), protoplast fusion, biolistic impact, electroporation, microinjection, or any other method that introduces the gene of interest into the host cell. More specific teachings applicable for oleaginous yeast (i.e., *Yarrowia lipolytica*) include U.S. Pat. Nos. 4,880,741 and 5,071,764 and Chen, D. C. et al. (*Appl Microbiol Biotechnol.* 48(2):232–235-(1997)).

For convenience, a host cell that has been manipulated by any method to take up a DNA sequence (e.g., an expression cassette) will be referred to as "transformed" or "recombinant" herein. The transformed host will have at least one copy of the expression construct and may have two or more, depending upon whether the gene is integrated into the genome, amplified, or is present on an extrachromosomal element having multiple copy numbers. The transformed host cell can be identified by selection for a marker contained on the introduced construct. Alternatively, a separate marker construct may be co-transformed with the desired construct, as many transformation techniques introduce many DNA molecules into host cells. Typically, transformed hosts are selected for their ability to grow on selective media. Selective media may incorporate an antibiotic or lack a factor necessary for growth of the untransformed host, such as a nutrient or growth factor. An introduced marker gene may confer antibiotic resistance or encode an essential growth factor or enzyme, thereby permitting growth on selective media when expressed in the transformed host. Selection of a transformed host can also occur when the expressed marker protein can be detected, either directly or indirectly. The marker protein may be expressed alone or as a fusion to another protein. The marker protein can be detected by: 1.) its enzymatic activity (e.g., β-galactosidase can convert the substrate X-gal [5-bromo-4-chloro-3-indolyl-β-D-galactopyranoside] to a colored product; luciferase can convert luciferin to a light-emitting product; β-glucuronidase (GUS) can convert the substrate "MUG" (4-methylumbellifery-b-glucuronide) to a colored product) or 2.) its light-producing or modifying characteristics (e.g., the green fluorescent protein of *Aequorea victoria* fluoresces when illuminated with blue light). Alternatively, antibodies can be used to detect the marker protein or a molecular tag on, for example, a protein of interest. Cells expressing the marker protein or tag can be selected, for example, visually, or by techniques such as FACS or panning using antibodies. For selection of yeast transformants, any marker that functions in yeast may be used. Preferred for use herein are resistance to kanamycin, hygromycin and the aminoglycoside G418, as well as ability to grow on media lacking uracil or leucine.

Techniques to Up-regulate Expression of a Chimeric Gene Comprising Regulatory Sequences of the Invention Operably Linked to a Coding Region of Interest Additional copies of a particular coding region of interest (operably linked to a FBA promoter, a FBAIN promoter, FBAINm promoter, or a chimeric promoter comprising the fba1 intron or fba1 enhancer) may be introduced into the host to increase expression. Expression of the coding region of interest also can be increased by removing/deleting destabilizing sequences from either the mRNA or the encoded protein, or by adding stabilizing sequences to the mRNA (U.S. Pat. No. 4,910,141).

Yet another approach to increase expression of the coding region of interest is to increase the translational efficiency of the encoded mRNAs by replacement of codons in the native gene with those for optimal gene expression in the selected host microorganism. As will be appreciated by one skilled in the art, use of host preferred codons can substantially enhance the expression of the foreign gene encoding the polypeptide. In general, host preferred codons can be determined within a particular host species of interest by examining codon usage in proteins (preferably those expressed in the largest amount) and determining which codons are used with highest frequency. Then, the coding sequence for a polypeptide of interest can be synthesized in whole or in part using the codons preferred in the host species.

Additionally, as shown herein, some enhancer elements located in the 5' or 3' noncoding region or introns can also be used to enhance the expression of a coding region of interest.

Preferred Hosts

Preferred host cells for expression of the instant genes and coding regions of interest operably linked to the instant regulatory sequences herein are yeast cells (where oleaginous yeast are most preferred where the desired use is for the production of microbial oils, infra). Oleaginous yeast are naturally capable of oil synthesis and accumulation, wherein the oil can comprise greater than about 25% of the cellular dry weight, more preferably greater than about 30% of the cellular dry weight, and most preferably greater than about 40% of the cellular dry weight. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeast include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis* and *Yarrowia lipolytica* (formerly classified as *Candida lipolytica*).

Most preferred is the oleaginous yeast *Yarrowia lipolytica*; and, in a further embodiment, most preferred are the *Y. lipolytica* strains designated as ATCC #20362, ATCC #8862, ATCC #18944, ATCC #76982 and/or LGAM S(7)1 (Papanikolaou S., and Aggelis G., *Bioresour. Technol.* 82(1):43–9 (2002)). The *Y. lipolytica* strain designated as ATCC #76982 was the particular strain from which the FBA, FBAIN and FBAINm promoters and fba1 gene were isolated herein.

Industrial Production Using Transformed Yeast Expressing a Suitable Coding Region of Interest In general, media conditions which may be optimized for high-level expression of a particular coding region of interest include the type and amount of carbon source, the type and amount of nitrogen source, the carbon-to-nitrogen ratio, the oxygen level, growth temperature, pH, length of the biomass production phase and the time of cell harvest. Microorganisms of interest, such as oleaginous yeast, are grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media in the present invention must contain a suitable carbon source. Suitable carbon sources may include, but are not limited to: monosaccharides (e.g., glucose, fructose), disaccharides (e.g., lactose, sucrose), oligosaccharides, polysaccharides (e.g., starch, cellulose or mixtures thereof, sugar alcohols (e.g., glycerol) or mixtures from renewable feedstocks (e.g., cheese whey permeate, cornsteep liquor, sugar beet molasses, barley malt). Additionally, carbon sources may include alkanes, fatty acids, esters of fatty acids, monoglycerides, diglycerides, triglycerides, phospholipids and various commercial sources of fatty acids including vegetable oils (e.g., soybean oil) and animal fats. Additionally, the carbon source may include one-carbon sources (e.g., carbon dioxide, methanol, formaldehyde, formate, carbon-containing amines) for which metabolic conversion into key biochemical intermediates has been demonstrated. Hence it is contemplated that the source of carbon utilized in the present invention may encompass a wide variety of carbon-containing sources and will only be limited by the choice of the host organism. Although all of the above mentioned carbon sources and mixtures thereof are expected to be suitable in the present invention, preferred carbon sources are sugars and/or fatty acids. Most preferred is glucose and/or fatty acids containing between 10–22 carbons.

Nitrogen may be supplied from an inorganic (e.g., $(NH_4)_2SO_4$) or organic source (e.g., urea or glutamate). In addition to appropriate carbon and nitrogen sources, the fermentation media must also contain suitable minerals, salts, cofactors, buffers, vitamins and other components known to those skilled in the art suitable for the growth of the microorganism.

Preferred growth media in the present invention are common commercially prepared media, such as Yeast Nitrogen Base (DIFCO Laboratories, Detroit, Mich.). Other defined or synthetic growth media may also be used and the appropriate medium for growth of the particular microorganism will be known by one skilled in the art of microbiology or fermentation science. A suitable pH range for the fermentation is typically between about pH 4.0 to pH 8.0, wherein pH 5.5 to pH 7.0 is preferred as the range for the initial growth conditions. The fermentation may be conducted under aerobic or anaerobic conditions, wherein microaerobic conditions are preferred.

Host cells comprising a suitable coding region of interest operably linked to the regulatory sequences of the present invention may be cultured using methods known in the art. For example, the cell may be cultivated by shake flask cultivation, small-scale or large-scale fermentation in laboratory or industrial fermentors performed in a suitable medium and under conditions allowing expression of the coding region of interest.

Where commercial production of a product that relies on the instant genetic chimera is desired, a variety of culture methodologies may be applied. For example, large-scale production of a specific gene product over-expressed from a recombinant host may be produced by a batch, fed-batch or continuous fermentation process.

A batch fermentation process is a closed system wherein the media composition is fixed at the beginning of the process and not subject to further additions beyond those required for maintenance of pH and oxygen level during the process. Thus, at the beginning of the culturing process the media is inoculated with the desired organism and growth or metabolic activity is permitted to occur without adding additional sources (i.e., carbon and nitrogen sources) to the medium. In batch processes the metabolite and biomass compositions of the system change constantly up to the time the culture is terminated. In a typical batch process, cells proceed through a static lag phase to a high growth log phase and finally to a stationary phase, wherein the growth rate is diminished or halted. Left untreated, cells in the stationary phase will eventually die. A variation of the standard batch process is the fed-batch process, wherein the source is continually added to the fermentor over the course of the fermentation process. A fed-batch process is also suitable in the present invention. Fed-batch processes are useful when catabolite repression is apt to inhibit the metabolism of the cells or where it is desirable to have limited amounts of source in the media at any one time. Measurement of the source concentration in fed-batch systems is difficult and therefore may be estimated on the basis of the changes of measurable factors such as pH, dissolved oxygen and the partial pressure of waste gases (e.g., $CO_2$). Batch and fed-batch culturing methods are common and well known in the art and examples may be found in Thomas D. Brock in *Biotechnology: A Textbook of Industrial Microbiology*, $2^{nd}$ ed., (1989) Sinauer Associates: Sunderland, Mass.; or Deshpande, Mukund V., *Appl. Biochem. Biotechnol.*, 36:227 (1992), herein incorporated by reference.

Commercial production may also be accomplished by a continuous fermentation process, wherein a defined media is continuously added to a bioreactor while an equal amount of culture volume is removed simultaneously for product recovery. Continuous cultures generally maintain the cells in the log phase of growth at a constant cell density. Continuous or semi-continuous culture methods permit the modulation of one factor or any number of factors that affect cell growth or end product concentration. For example, one approach may limit the carbon source and allow all other parameters to moderate metabolism. In other systems, a number of factors affecting growth may be altered continuously while the cell concentration, measured by media turbidity, is kept constant. Continuous systems strive to maintain steady state growth and thus the cell growth rate must be balanced against cell loss due to media being drawn off the culture. Methods of modulating nutrients and growth factors for continuous culture processes, as well as techniques for maximizing the rate of product formation, are well known in the art of industrial microbiology and a variety of methods are detailed by Brock, supra.

DESCRIPTION OF PREFERRED EMBODIMENTS

Although the regulatory sequences derived from the *Yarrowia lipolytica* fba1 gene of the present invention will be suitable for expression of any suitable coding region of interest in a yeast, in a preferred embodiment the promoters will be utilized in the development of an oleaginous yeast that accumulates oils enriched in PUFAs. Toward this end, it is necessary to introduce and express e.g., desaturases and elongases that allow for the synthesis and accumulation of ω-3 and/or ω-6 fatty acids.

The term "fatty acids" refers to long chain aliphatic acids (alkanoic acids) of varying chain lengths, from about $C_{12}$ to $C_{22}$ (although both longer and shorter chain-length acids are known). The predominant chain lengths are between $Cl_{16}$ and $C_{22}$. The structure of a fatty acid is represented by a simple notation system of "X:Y", where X is the total number of carbon (C) atoms and Y is the number of double bonds.

Generally, fatty acids are classified as saturated or unsaturated. The term "saturated fatty acids" refers to those fatty acids that have no "double bonds" between their carbon backbone. In contrast, "unsaturated fatty acids" are cis-isomers that have "double bonds" along their carbon backbones. "Monounsaturated fatty acids" have only one "double bond" along the carbon backbone (e.g., usually between the $9^{th}$ and $10^{th}$ carbon atom as for palmitoleic acid (16:1) and oleic acid (18:1)), while "polyunsaturated fatty acids" (or "PUFAs") have at least two double bonds along the carbon backbone (e.g., between the $9^{th}$ and $10^{th}$, and $12^{th}$ and $13^{th}$ carbon atoms for linoleic acid (18:2); and between the $9^{th}$ and $10^{th}$, $12^{th}$ and $13^{th}$, and $15^{th}$ and $16^{th}$ for α-linolenic acid (18:3)).

"PUFAs" can be classified into two major families (depending on the position (n) of the first double bond nearest the methyl end of the fatty acid carbon chain). Thus, the "ω-6 fatty acids" (ω-6 or n-6) have the first unsaturated double bond six carbon atoms from the omega (methyl) end of the molecule and additionally have a total of two or more double bonds, with each subsequent unsaturation occurring 3 additional carbon atoms toward the carboxyl end of the molecule. In contrast, the "ω-3 fatty acids" (ω-3 or n-3) have the first unsaturated double bond three carbon atoms away from the omega end of the molecule and additionally have a total of three or more double bonds, with each subsequent unsaturation occurring 3 additional carbon atoms toward the carboxyl end of the molecule.

For the purposes of this disclosure, the omega-reference system will be used to indicate the number of carbons, the number of double bonds and the position of the double bond closest to the omega carbon, counting from the omega carbon (which is numbered 1 for this purpose). This nomenclature is shown below in Table 2, in the column titled "Shorthand Notation". The remainder of the Table summarizes the common names of ω-3 and ω-6 fatty acids, the abbreviations that will be used throughout the remainder of the specification, and each compounds' chemical name.

TABLE 2

Nomenclature Of Polyunsaturated Fatty Acids

| Common Name | Abbreviation | Chemical Name | Shorthand Notation |
|---|---|---|---|
| Linoleic | LA | cis-9,12-octadecadienoic | 18:2 ω-6 |
| γ-Linoleic | GLA | cis-6,9,12-octadecatrienoic | 18:3 ω-6 |
| Eicosadienoic | EDA | cis-11,14-eicosadienoic | 20:2 ω-6 |
| Dihomo-γ-Linoleic | DGLA | cis-8,11,14-eicosatrienoic | 20:3 ω-6 |
| Arachidonic | ARA | cis-5,8,11,14-eicosatetraenoic | 20:4 ω-6 |
| α-Linolenic | ALA | cis-9,12,15-octadecatrienoic | 18:3 ω-3 |
| Stearidonic | STA | cis-6,9,12,15-octadecatetraenoic | 18:4 ω-3 |
| Eicosatrienoic | ETrA | cis-11,14,17-eicosatrienoic | 20:3 ω-3 |
| Eicosatetraenoic | ETA | cis-8,11,14,17-eicosatetraenoic | 20:4 ω-3 |
| Eicosapentaenoic | EPA | cis-5,8,11,14,17-eicosapentaenoic | 20:5 ω-3 |
| Docosapentaenoic | DPA | cis-7,10,13,16,19-docosapentaenoic | 22:5 ω-3 |
| Docosahexaenoic | DHA | cis-4,7,10,13,16,19-docosahexaenoic | 22:6 ω-3 |

Microbial Biosynthesis of Fatty Acids

In general, lipid accumulation in oleaginous microorganisms is triggered in response to the overall carbon to nitrogen ratio present in the growth medium. When cells have exhausted available nitrogen supplies (e.g., when the carbon to nitrogen ratio is greater than about 40), the depletion of cellular adenosine monophosphate (AMP) leads to the cessation of AMP-dependent isocitrate dehydrogenase activity in the mitochondria and the accumulation of citrate, transport of citrate into the cytosol, and subsequent cleavage of the citrate by ATP-citrate lyase to yield acetyl-CoA and oxaloacetate. Acetyl-CoA is the principle building block for de novo biosynthesis of fatty acids. The first committed step of fatty acid biosynthesis is the synthesis of malonyl-CoA, produced via carboxylation of acetyl-CoA. Fatty acid synthesis is catalyzed by a multi-enzyme fatty acid synthase complex and occurs by the condensation of eight two-carbon fragments (acetyl groups from acetyl-CoA) to form a 16-carbon saturated fatty acid, palmitate.

Palmitate is the precursor of longer chain saturated and unsaturated fatty acids (e.g., stearic (18:0), palmitoleic (16:1) and oleic (18:1) acids) through the action of elongases and desaturases present in the endoplasmic reticulum membrane. Palmitate and stearate are converted to their unsaturated derivatives, palmitoleic (16:1) and oleic (18:1) acids, respectively, by the action of a Δ9 desaturase.

Biosynthesis of Omega-3 and Omega-6 Fatty Acids

Simplistically, the metabolic process that converts LA to GLA, DGLA and ARA (the ω-6 pathway) and ALA to STA, ETA, EPA and DHA (the ω-3 pathway) involves elongation of the carbon chain through the addition of carbon atoms and desaturation of the molecule through the addition of double bonds. This requires a series of special desaturation and elongation enzymes present in the endoplasmic reticulim membrane, hereinafter referred to as "PUFA biosynthetic pathway enzymes".

More specifically, "PUFA biosynthetic pathway enzymes" will refer to any of the following enzymes (and genes which encode said enzymes) associated with the biosynthesis of a PUFA, including: a Δ4 desaturase, a Δ5 desaturase, a Δ6 desaturase, a Δ12 desaturase, a Δ15 desaturase, a Δ17 desaturase, a Δ8 desaturase, a Δ9 desaturase and/or an elongase(s). For further clarity within the present disclosure, the term "desaturase" refers to a polypeptide that can desaturate one or more fatty acids to produce a mono- or polyunsaturated fatty acid or precursor of interest. Thus, despite use of the omega-reference system to refer to specific fatty acids, it is more convenient to indicate the activity of a desaturase by counting from the carboxyl end of the source using the delta-system. For example, a Δ17 desaturase will desaturate a fatty acid between the $17^{th}$ and $18^{th}$ carbon atom numbered from the carboxyl-terminal end of the molecule and can, for example, catalyze the conversion of ARA to EPA and/or DGLA to ETA. In contrast, the term "elongase" refers to a polypeptide that can elongate a fatty acid carbon chain to produce a mono- or polyunsaturated fatty acid that is 2 carbons longer than the fatty acid source that the elongase acts upon. This process of elongation occurs in a multi-step mechanism in association with fatty acid synthase, whereby CoA is the acyl carrier (Lassner et al., *The Plant Cell* 8:281–292 (1996)). Briefly, malonyl-CoA is condensed with a long-chain acyl-CoA to yield $CO_2$ and a β-ketoacyl-CoA (where the acyl moiety has been elongated by two carbon atoms). Subsequent reactions include reduction to β-hydroxyacyl-CoA, dehydration to an enoyl-CoA and a second reduction to yield the elongated acyl-CoA.

Synthesis of ω-6 fatty acids occurs in the following fashion: oleic acid (the first of the ω-6 fatty acids) is converted to LA (18:2) by the action of a Δ12 desaturase (FIG. 10). Subsequent ω-6 fatty acids are produced as follows: 1.) LA is converted to GLA by the activity of a Δ6 desaturase; 2.) GLA is converted to DGLA by the action of an elongase; and 3.) DGLA is converted to ARA by the action of a Δ5 desaturase. Alternatively, LA is converted to EDA by a Δ9 elongase; and a Δ8 desaturase then converts the EDA to DGLA.

In contrast, ω-3 fatty acids are all derived from linoleic acid (LA). Specifically: 1.) LA is converted to ALA by the action of a Δ15 desaturase; 2.) ALA is converted to STA by the activity of a Δ6 desaturase; 3.) STA is converted to ETA by the activity of an elongase; and 4.) ETA is converted to EPA by the activity of a Δ5 desaturase. Alternatively, ETA and EPA can be produced from DGLA and ARA, respectively, by the activity of a Δ17 desaturase. Or, in another embodiment, a Δ9 elongase is able to catalyze the conversion of ALA to ETrA; the ETrA is then converted to ETA by a Δ8 desaturase. EPA can be further converted to DHA by the activity of an elongase and a Δ4 desaturase.

Production of PUFAs

As will be obvious to one skilled in the art, the particular functionalities required to be introduced into a host organism for production of a particular PUFA final product will depend on the host cell (and its native PUFA profile and/or desaturase profile), the availability of substrate and the desired end product(s). As shown in FIG. 10, LA, GLA, EDA, DGLA, ARA, ALA, STA, ETrA, ETA, EPA, DPA and DHA may all be produced in oleaginous yeast, by introducing various combinations of the following PUFA enzyme functionalities: a Δ4 desaturase, a Δ5 desaturase, a Δ6 desaturase, a Δ12 desaturase, a Δ15 desaturase, a Δ17 desaturase, a Δ9 desaturase, a Δ8 desaturase and/or an elongase(s). One skilled in the art will be able to identify various candidate genes encoding each of the above enzymes, according to publicly available literature (e.g., GenBank), the patent literature and experimental analysis of microorganisms having the ability to produce PUFAs. Thus, a variety of desaturases and elongases are suitable as coding regions of interest in the present invention. These coding regions of interest could be operably linked to the FBA promoter, FBAIN promoter, FBAINm promoter, and/or a chimeric promoter comprising the fba1 intron or fba1 enhancer of the present invention (or mutant promoters thereof) and used as chimeric genes for expression of various ω-6 and ω-3 fatty acids, using techniques well known to those skilled in the art (see, for example co-pending U.S. patent application Ser. No. 10/840,579, herein incorporated entirely by reference). As such, the invention provides a method for the production of ω-3 and/or ω-6 fatty acids comprising:

(a) providing a transformed oleaginous yeast host cell comprising a chimeric gene, the chimeric gene comprising:
1) a regulatory sequence of a fba1 gene; and
2) a coding region of interest expressible in the oleaginous yeast encoding an enzyme of a functional ω-3/ω-6 fatty acid biosynthetic pathway;
wherein the regulatory sequence and coding region are operably linked; and
(b) growing the host cell of step (a) under suitable growth conditions whereby one or more ω-3 or ω-6 fatty acids are produced.

In preferred embodiments, the nucleic acid sequence of the regulatory sequence is selected from the group consisting of: SEQ ID NOs:17, 18, 19, 25, 26, 27, 46, 55 and 72 and subsequences and mutant promoters thereof; and the coding region of interest is any desaturase or elongase suitable for expression in the oleaginous yeast for the production of ω-3 or ω-6 fatty acids.

For production of the greatest and the most economical yield of PUFAs, the transformed oleaginous yeast host cell is grown under conditions that optimize desaturase and elongase activities by optimizing expression of the chimeric genes of the present invention, wherein these chimeric genes comprise a regulatory sequence of a fba1 gene and a coding region of interest encoding a PUFA biosynthetic pathway enzyme.

In the fermentation media, particular attention is given to several metal ions (e.g., $Mn^{+2}$, $Co^{+2}$, $Zn^{+2}$, $Mg^{+2}$) that promote synthesis of lipids and PUFAs (Nakahara, T. et al. *Ind. Appl. Single Cell Oils*, D. J. Kyle and R. Colin, eds. pp 61–97 (1992)).

The preferred fermentable carbon source for production of oleaginous yeast expressing various ω-6 and ω-3 fatty acids will include (but is not limited to) monosaccharides, oligosaccharides, polysaccharides, alkanes, fatty acids, esters of fatty acids, monoglycerides, diglycerides, triglycerides, carbon dioxide, methanol, formaldehyde, formate and carbon-containing amines.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of PUFAs in oleaginous yeast. In this approach, the first stage of the fermentation is dedicated to the generation and accumulation of cell mass and is characterized by rapid cell growth and cell division. In the second stage of the fermentation, it is preferable to establish conditions of nitrogen deprivation in the culture to promote high levels of lipid accumulation. The effect of this nitrogen deprivation is to reduce the effective concentration of AMP in the cells, thereby reducing the activity of the NAD-dependent isocitrate dehydrogenase of mitochondria. When this occurs, citric acid will accumulate, thus forming abundant pools of acetyl-CoA in the cytoplasm and priming fatty acid synthesis. Thus, this phase is characterized by the cessation of cell division followed by the synthesis of fatty acids and accumulation of oil. Although cells are typically grown at about 30° C., some studies have shown increased synthesis of unsaturated fatty acids at lower temperatures (Yongmanitchai and Ward, *Appl. Environ. Microbiol.* 57:419–25 (1991)). Based on process economics, this temperature shift should likely occur after the first phase of the two-stage fermentation, when the bulk of the organisms' growth has occurred.

Purification of PUFAs

The PUFAs produced in a host microorganism as described herein may be found as free fatty acids or in esterified forms such as acylglycerols, phospholipids, sulfolipids or glycolipids, and may be extracted from the host cell through a variety of means well-known in the art. One review of extraction techniques, quality analysis and acceptability standards for yeast lipids is that of Z. Jacobs (*Critical Reviews in Biotechnology* 12(5/6):463–491 (1992)). A brief review of downstream processing is also available by A. Singh and O. Ward (*Adv. Appl. Microbiol.* 45:271–312 (1997)).

In general, means for the purification of PUFAs may include extraction with organic solvents, sonication, supercritical fluid extraction (e.g., using carbon dioxide), saponification, and physical means such as presses, or combinations thereof. Of particular interest is extraction with methanol and chloroform in the presence of water (E. G. Bligh & W. J. Dyer, *Can. J. Biochem. Physiol.* 37:911–917 (1959)). Where desirable, the aqueous layer can be acidified to protonate negatively-charged moieties and thereby increase partitioning of desired products into the organic layer. After extraction, the organic solvents can be removed by evaporation under a stream of nitrogen. When isolated in conjugated forms, the products may be enzymatically or chemically cleaved to release the free fatty acid or a less complex conjugate of interest, and can then be subject to further manipulations to produce a desired end product. Desirably, conjugated forms of fatty acids are cleaved with potassium hydroxide.

If further purification is necessary, standard methods can be employed. Such methods may include extraction, treatment with urea, fractional crystallization, HPLC, fractional distillation, silica gel chromatography, high-speed centrifugation or distillation, or combinations of these techniques. Protection of reactive groups, such as the acid or alkenyl groups, may be done at any step through known techniques (e.g., alkylation or iodination). Methods used include methylation of the fatty acids to produce methyl esters. Similarly, protecting groups may be removed at any step. Desirably, purification of fractions containing GLA, STA, ARA, DHA and EPA may be accomplished by treatment with urea and/or fractional distillation.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by: 1.) Sambrook, J., Fritsch, E. F. and Maniatis, T. *Molecular Cloning: A Laboratory Manual*; Cold Spring Harbor Laboratory: Cold Spring Harbor, N.Y. (1989) (Maniatis); 2.) T. J. Silhavy, M. L. Bennan, and L. W. Enquist, Experiments with Gene Fusions; Cold Spring Harbor Laboratory: Cold Spring Harbor, N.Y. (1984); and 3.) Ausubel, F. M. et al., Current Protocols in Molecular Biology, published by Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in *Biotechnology: A Textbook of Industrial Microbiology*, 2$^{nd}$ ed., Sinauer Associates: Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.) or Sigma Chemical Company (St. Louis, Mo.), unless otherwise specified.

A leucine autotrophic strain of *Yarrowia lipolytica* was purchased from the American Type Culture Collection (Rockville, Md.; ATCC #76982) and used for functional assays, as well as *Yarrowia lipolytica* ATCC #20362. *Y. lipolytica* strains were usually grown at 28° C. on YPD agar (1% yeast extract, 2% bactopeptone, 2% glucose, 2% agar). For transformation selection, minimal medium (0.17% yeast nitrogen base (DIFCO Laboratories) without ammonium sulfate and without amino acids, 2% glucose, 0.1% proline, pH 6.1) was used. Supplements of adenine, leucine, lysine and/or uracil were added to a final concentration of 0.01%.

General molecular cloning was performed according to standard methods (Sambrook et al., supra). Oligonucleotides were synthesized by Sigma-Genosys (Spring, Tex.). Site-directed mutagenesis was performed using Stratagene's QuickChange™ Site-Directed Mutagenesis kit (San Diego, Calif.), per the manufacturer's instructions. When polymerase chain reaction (PCR) or site-directed mutagenesis was involved in subcloning, the constructs were sequenced to confirm that no errors had been introduced to the sequence. PCR products were cloned into Promega's pGEM-T-easy vector (Madison, Wis.).

Manipulations of genetic sequences were accomplished using the suite of programs available from the Genetics Computer Group Inc. (Wisconsin Package Version 9.0, Genetics Computer Group (GCG), Madison, Wis.). The GCG program "Pileup" was used with the gap creation default value of 12, and the gap extension default value of 4. The GCG "Gap" or "Bestfit" programs were used with the default gap creation penalty of 50 and the default gap extension penalty of 3. Unless otherwise stated, in all other cases GCG program default parameters were used.

The meaning of abbreviations is as follows: "sec" means second(s), "min" means minute(s), "h" means hour(s), "d" means day(s), "μl" means microliter(s), "mL" means milliliter(s), "L" means liter(s), "μM" means micromolar, "mM" means millimolar, "M" means molar, "mmol" means millimole(s), "μmole" mean micromole(s), "g" means gram(s), "μg" means microgram(s), "ng" means nanogram(s), "U" means unit(s), "bp" means base pair(s), "kB" means kilobase(s) and "AA" means amino acid.

Example 1

Isolation of a Portion of the Coding Region of the *Yarrowia lipolytica* fba1 Gene The present Example describes the identification of a portion of the *Yarrowia lipolytica* gene encoding FBA1 (SEQ ID NOs:10 and 11), by use of primers derived from conserved regions of other fba1 sequences.

Figure 1A:
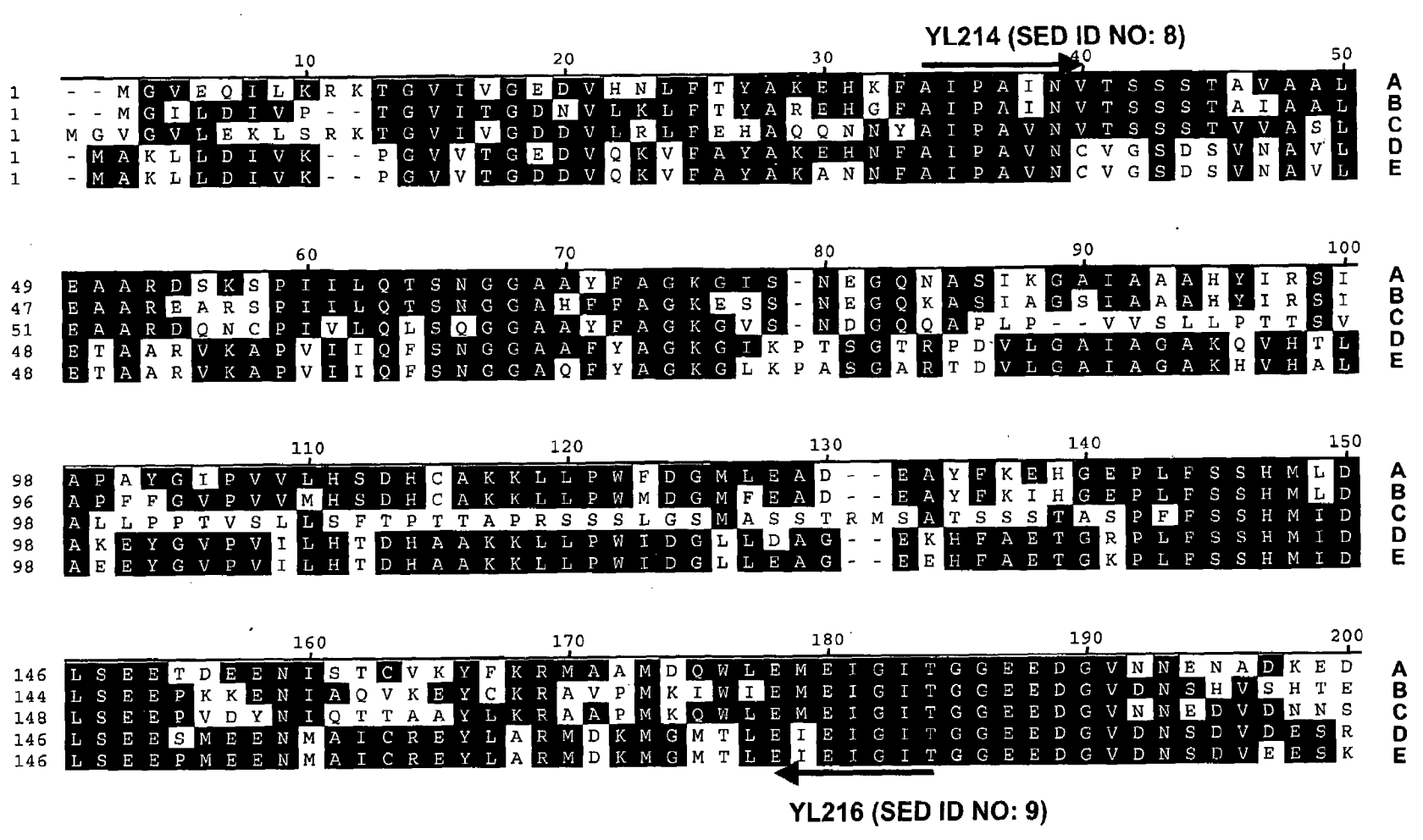

A comparison of the various protein sequences encoding fba1 genes from *Saccharomyces cerevisiae* (GenBank Accession No. NP_012863; SEQ ID NO:1), *Schizosaccharomyces pombe* (GenBank Accession No. NP_595692; SEQ ID NO:2), *Aspergillus oryzae* (GenBank Accession No. BAB12232; SEQ ID NO:3), *Haemophilus influenzae* (GenBank Accession No. NP_438682; SEQ ID NO:4) and *Pasteurella multocida* (GenBank Accession No. NP_246800; SEQ ID NO:5) showed that there were several stretches of conserved amino acid sequence between the 5 different organisms (FIGS. 1A and 1B). Thus, two degenerate oligonucleotides (shown below), corresponding to the conserved 'AIPAINV' (SEQ ID NO:6) and 'EMEIGIT' (SEQ ID NO:7) amino acid sequences, respectively, were designed and used to amplify a portion of the coding region of fba1 from *Y. lipolytica*:

Degenerate oligonucleotide YL214 (SEQ ID NO:8)
AAGTACGAYTCBACYCAYGG

Degenerate oligonucleotide YL216 (SEQ ID NO:9)
ACRGCCTTRGCRGCDCCRGT

[Note: The nucleic acid degeneracy code used for SEQ ID NOs:8 and 9 was as follows: R=A/G; Y=C/T; B=C/G/T; and D=A/G/T.]

Based on the full-length sequences of the fba1 sequences of FIG. 1, it was hypothesized that the *Yarrowia lipolytica* fba1 gene amplified as described above would be missing ~31 amino acids from its N-terminus and about ~180 amino acids from its C-terminus.

The PCR amplification was carried out in a 50 μl total volume comprising: PCR buffer (containing 10 mM KCl, 10 mM (NH$_4$)$_2$SO$_4$, 20 mM Tris-HCl (pH 8.75), 2 mM MgSO$_4$, 0.1% Triton X-100), 100 μg/mL BSA (final concentration), 200 μM each deoxyribonucleotide triphosphate, 10 pmole of each primer, 50 ng genomic DNA of *Y. lipolytica* (ATCC #76982) and 1 μl of Taq DNA polymerase (Epicentre Technologies, Madison, Wis.). The thermocycler conditions were set for 35 cycles at 95° C. for 1 min, 56° C. for 30 sec and 72° C. for 1 min, followed by a final extension at 72° C. for 10 min.

The PCR products were purified using a Qiagen PCR purification kit (Valencia, Calif.), and then further purified following gel electrophoresis in 1% (w/v) agarose. Subsequently, the PCR products were cloned into the pGEM-T-easy vector (Promega, Madison, Wis.). The ligated DNA was used to transform cells of E. coli DH10B and transformants were selected on LB (1% bacto-tryptone, 0.5% bacto-yeast extract and 1% NaCl) agar containing ampicillin (100 μg/mL). Analysis of the plasmid DNA from one transformant confirmed the presence of a plasmid of the expected size (designated as "pT-FBA1").

Sequence analyses showed that pT-FBA1 contained a 436 bp fragment (SEQ ID NO:10). Identity of this sequence was determined by conducting BLAST (Basic Local Alignment Search Tool; Altschul, S. F., et al., *J. Mol. Biol.* 215:403–410 (1993)) searches for similarity to sequences contained in the BLAST "nr" database (comprising all non-redundant GenBank CDS translations, sequences derived from the 3-dimensional structure Brookhaven Protein Data Bank, the SWISS-PROT protein sequence database, EMBL and DDBJ databases). The sequence was analyzed for similarity to all publicly available DNA sequences contained in the "nr" database using the BLASTN algorithm provided by the National Center for Biotechnology Information (NCBI). The DNA sequence was translated in all reading frames and compared for similarity to all publicly available protein sequences contained in the "nr" database, using the BLASTX algorithm (Gish, W. and States, D. J. *Nature Genetics* 3:266–272 (1993)) provided by the NCBI. The results of the BLAST comparison summarizing the sequence to which SEQ ID NO:10 has the most similarity are reported according to the % identity, % similarity and Expectation value. "% Identity" is defined as the percentage of amino acids that are identical between the two proteins. "% Similarity" is defined as the percentage of amino acids that are identical or conserved between the two proteins. "Expectation value" estimates the statistical significance of the match, specifying the number of matches, with a given score, that are expected in a search of a database of this size absolutely by chance.

Figure 2:
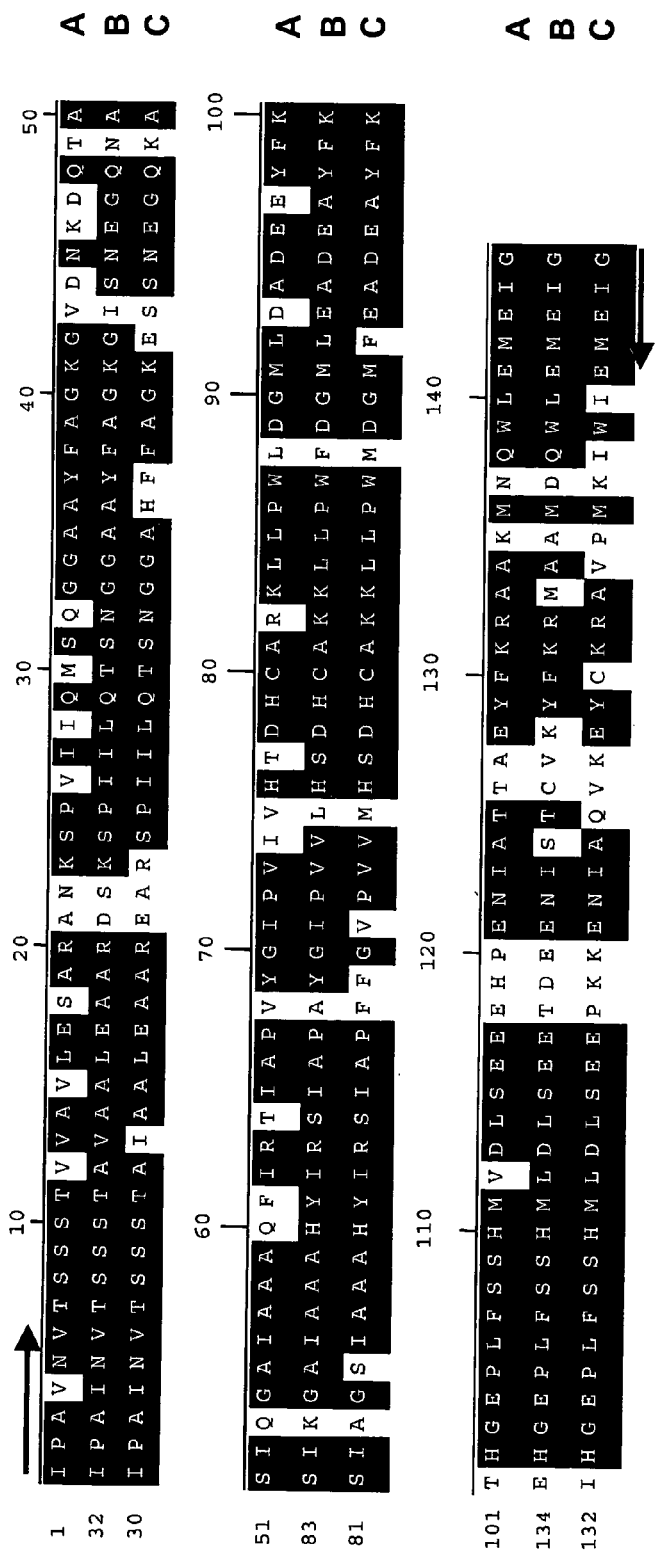
FIG. 2 shows an alignment of amino acids encoding portions of the FBA1 protein from *Yarrowia lipolytica, Saccharomyces cerevisiae* and *Schizosaccharomyces pombe*.

The 436 bp of pT-FBA1 was found to encode 145 amino acids (SEQ ID NO:11). This amino acid fragment had 77% identity and 86% similarity (FIG. 2) with the FBA protein sequence of *Saccharomyces cerevisiae* (GenBank Accession No. NP_012863), with an expectation value of 9E-54. The *Yarrowia* sequence possessed the 'AIPAINV' (SEQ ID NO:6) and 'EMEIGIT' (SEQ ID NO:7) amino acid sequences (corresponding to the degenerate primers used to amplify the fragment) at its N- and C-termini. Further sequence comparison of this partial FBA1 sequence determined that it also shared about 66% and 67% identity with the FBA1 proteins from *Kluyvermyces lactis* (SEQ ID NO:12; GenBank Accession No. CAC29023) and *Paracoccidiodes brasiliensis* (SEQ ID NO:13; GenBank Accession No. AAL34519), respectively.

Example 2

Isolation of the 5' Upstream Regions of the fba1 Gene from *Yarrowia lipolytica*

To isolate the promoter for the fba1 gene identified in Example 1, a genome-walking technique (TOPO® Walker Kit, Invitrogen, Carlsbad, Calif.) was utilized.

Briefly, genomic DNA of *Y. lipolytica* was digested with KpnI, SacI, SphI or PacI; each digest was then dephosphorylated with Calf Intestinal Alkaline Phosphatase (CIP). Primer extension reactions were then carried out individually using the dephosphorylated DNA as the template and oligonucleotide YL217 (SEQ ID NO:14) as the primer. The primer extended products were linked with TOPO® linker and used as templates for first PCR reactions using primers of LinkAmp Primer1 and YL218 (SEQ ID NO:15). The PCR amplifications were carried out in a 50 μl total volume, comprising: PCR buffer (containing 10 mM KCl, 10 mM $(NH_4)_2SO_4$, 20 mM Tris-HCl (pH 8.75), 2 mM $MgSO_4$, 0.1% Triton X-100), 100 μg/mL BSA (final concentration), 200 μM each deoxyribonucleotide triphosphate, 10 pmole of each primer and 1 μl of Taq DNA polymerase (Epicentre Technologies). The thermocycler conditions were set for 35 cycles at 95° C. for 1 min, 56° C. for 30 sec and 72° C. for 1 min, followed by a final extension at 72° C. for 10 min.

A second PCR reaction was then carried out using the first PCR product as the template and primers LinkAmp primer 2 and YL219 (SEQ ID NO:16). The PCR amplifications were carried out as described above.

The PCR product comprising the 5' upstream region of the fba1 gene was purified using a Qiagen PCR purification kit, followed by gel electrophoresis in 1% (w/v) agarose. Products were then cloned into the pGEM-T-easy vector (Promega, Madison, Wis.). The ligated DNA was used to transform *E. coli* DH10B and transformants were selected on LB agar containing ampicillin (100 μg/mL).

Figure 3:
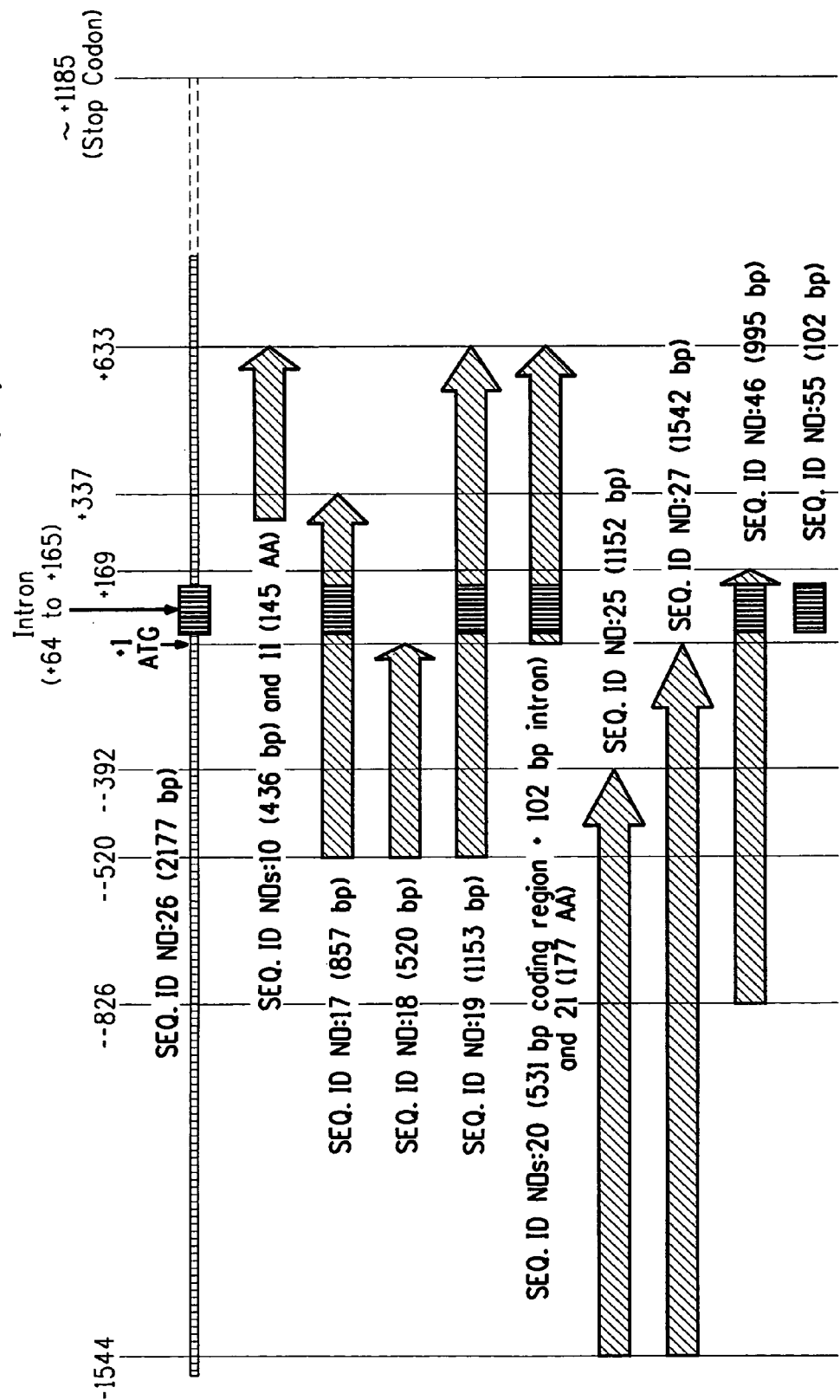
FIG. 3 illustrates the relationship between SEQ ID NOs: 10, 11, 17, 18, 19, 20, 21, 25, 26, 27, 46 and 55, each of which relates to the fructose-bisphosphate aldolase (fba1) gene in *Yarrowia lipolytica*.

Analysis of the plasmid DNA from one transformant comprising the 5' upstream region of the fba1 gene confirmed the presence of the expected plasmid, designated "pT-FBA1P". Sequence analyses showed that pT-FBA1P contained a fragment of 857 bp (SEQ ID NO:17), which included 520 bp of 5' upstream sequence (SEQ ID NO:18) from the nucleotide 'A' (designated as +1) of the putative translation initiation codon 'ATG' of the fba1 gene. A complete assembly of overlapping SEQ ID NOs:17 and 10 yielded a single contig comprising 520 bp upstream of the putative initiation codon and 633 bp coding region of the fba1 gene (SEQ ID NO:19; FIG. 3). Further analysis of the fba1 DNA sequence (+1 to +633) revealed the presence of an intron of 102 bp (base pairs +64 to +165, corresponding to SEQ ID NO:55). Thus, the isolated coding region of the fba1 gene in *Yarrowia lipolytica* is only 531 bp in length (SEQ ID NO:20) and the corresponding amino acid sequence (SEQ ID NO:21) is 177 amino acids. The amino acid sequence was compared via BLAST analysis for similarity to all publicly available protein sequences (supra, Example 1). Based on this analysis, it was determined that the *Yarrowia* FBA1 protein was most similar to the FBA1 of *Kluyveromyces lactis* (SEQ ID NO:12; GenBank Accession No. CAC29023) with 73% identity.

The gene walking technique was repeated to obtain more of the upstream sequence of the fba1 gene, using the methodology described above. However, primers ODMW315 (SEQ ID NO:22), ODMW316 (SEQ ID NO:23) and ODMW317 (SEQ ID NO:24) were substituted for primers YL217, YL218 and YL219, respectively. Analysis of the plasmid DNA from one transformant comprising the 5' upstream region of the fba1 gene confirmed the presence of the expected plasmid, designated "pT-FBA1P2". Sequence analyses showed that pT-FBA1P2 contained a fragment of 1152 bp (SEQ ID NO:25), entirely upstream from the 5' sequence of the fba1 gene that was identified from the first round of gene walking. A complete assembly of overlapping SEQ ID NOs:25, 17 and 10 yielded a single contig of 2177 bp (SEQ ID NO:26) comprising 1542 bp (SEQ ID NO:27) upstream and 633 bp downstream of the putative initiation codon of the fba1 gene (FIG. 3).

Example 3

Synthesis of pY5–30

The present Example describes the synthesis of pY5–30 (SEQ ID NO:62), comprising a chimeric TEF::GUS::XPR gene. This was required for comparative studies investigating the promoter activities of the GPD, GPM, TEF, FBA and FBAIN promoters, wherein constructs comprising each promoter and the *E. coli* gene encoding β-glucuronidase (GUS) as a reporter gene (Jefferson, R. A. *Nature*. 14(342):837–838 (1989)) were prepared and analyzed (Examples 4–6, infra).

Amplification of the GUS Coding Region

The GUS coding region was amplified using pBI101 (Jefferson, R. A. et al., *EMBO J.* 6:3901–3907 (1987)) as template and oligonucleotides YL33 (SEQ ID NO:28) and YL34 (SEQ ID NO:29) as primers. The PCR amplification was carried out in a 50 µl total volume comprising: PCR buffer (containing 10 mM KCl, 10 mM $(NH_4)_2SO_4$, 20 mM Tris-HCl (pH 8.75), 2 mM $MgSO_4$, 0.1% Triton X-100), 100 µg/mL BSA (final concentration), 200 µM each deoxyribonucleotide triphosphate, 10 pmole of each primer and 1 µl of Pfu DNA polymerase (Stratagene, San Diego, Calif.). The thermocycler conditions were set for 35 cycles at 95° C. for 1 min, 56° C. for 30 sec and 72° C. for 1 min, followed by a final extension at 72° C. for 10 min. The PCR products were digested with NcoI and PacI.

Synthesis of Plasmid pY5–10

The plasmid pY5, a derivative of pINA532 (a gift from Dr. Claude Gaillardin, Insitut National Agronomics, Centre de biotechnologie Agro-Industrielle, laboratoire de Genetique Moleculaire et Cellularie INRA-CNRS, F-78850 Thiverval-Grignon, France), was constructed for expression of heterologous genes in *Yarrowia lipolytica*, as diagrammed in FIG. 4. The partially-digested 3598 bp EcoRI fragment containing the ARS18 sequence and LEU2 gene of pINA532 was subcloned into the EcoRI site of pBluescript (Stratagene, San Diego, Calif.) to generate pY2.

The TEF promoter (SEQ ID NO 30; Muller S., et al. *Yeast*, 14: 1267–1283 (1998)) was amplified from *Yarrowia lipolytica* genomic DNA by PCR using TEF5' (SEQ ID NO:31) and TEF3' (SEQ ID NO:32) as primers. PCR amplification was carried out in a 50 µl total volume containing: 100 ng *Yarrowia* genomic DNA, PCR buffer (containing 10 mM KCl, 10 mM $(NH_4)_2SO_4$, 20 mM Tris-HCl (pH 8.75), 2 mM $MgSO_4$, 0.1% Triton X-100), 100 µg/mL BSA (final concentration), 200 µM each deoxyribonucleotide triphosphate, 10 pmole of each primer and 1 µl of Pfu Turbo DNA polymerase (Stratagene, San Diego, Calif.). Amplification was carried out as follows: initial denaturation at 95° C. for 3 min, followed by 35 cycles of the following: 95° C. for 1 min, 56° C. for 30 sec, 72° C. for 1 min. A final extension cycle of 72° C. for 10 min was carried out, followed by reaction termination at 4° C. The 418 bp PCR product was ligated into pCR-Blunt to generate pIP-tef. The BamHI/EcoRV fragment of pIP-tef was subcloned into the BamHI/SmaI sites of pY2 to generate pY4.

The XPR2 transcriptional terminator (SEQ ID NO:33) was amplified by PCR using pINA532 as template and XPR5' (SEQ ID NO:34) and XPR3' (SEQ ID NO:35) as primers. The PCR amplification was carried out in a 50 µl total volume, using the components and conditions described above. The 179 bp PCR product was digested with SacII and then ligated into the SacII site of pY4 to generate pY5. Thus, pY5 (shown in FIG. 4) contained: a *Yarrowia* autonomous replication sequence (ARS18); a ColE1 plasmid origin of replication; an ampicillin-resistance gene ($Amp^R$), for selection in *E. coli*; a *Yarrowia* LEU2 gene, for selection in *Yarrowia*; the translation elongation promoter ("TEF P"), for expression of heterologous genes in *Yarrowia*; and the extracellular protease gene terminator (XPR2) for transcriptional termination of heterologous gene expression in *Yarrowia*.

Figure 4A:
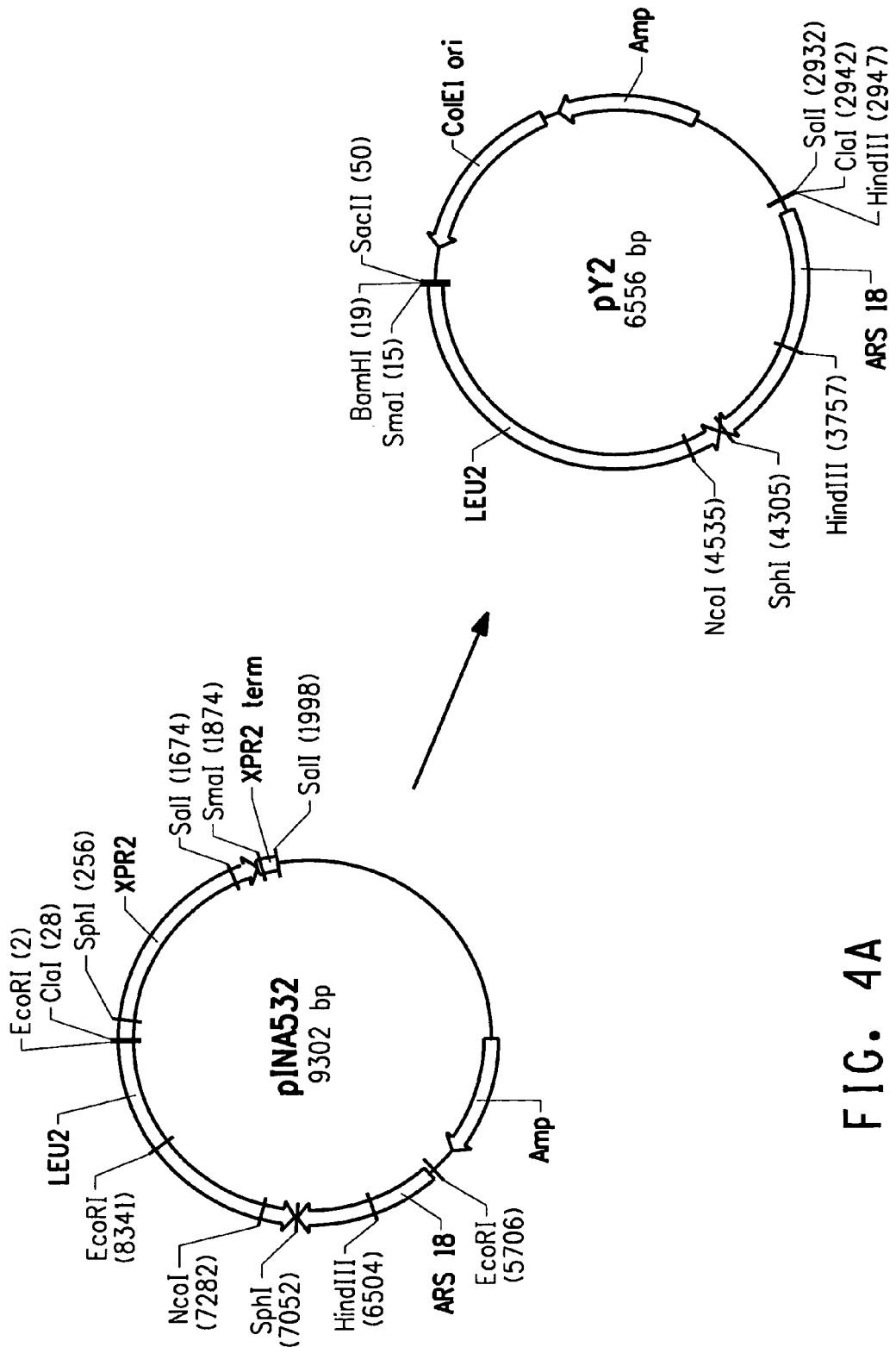
FIG. 4 illustrates the construction of plasmid vector pY5–4.
Figure 4B:
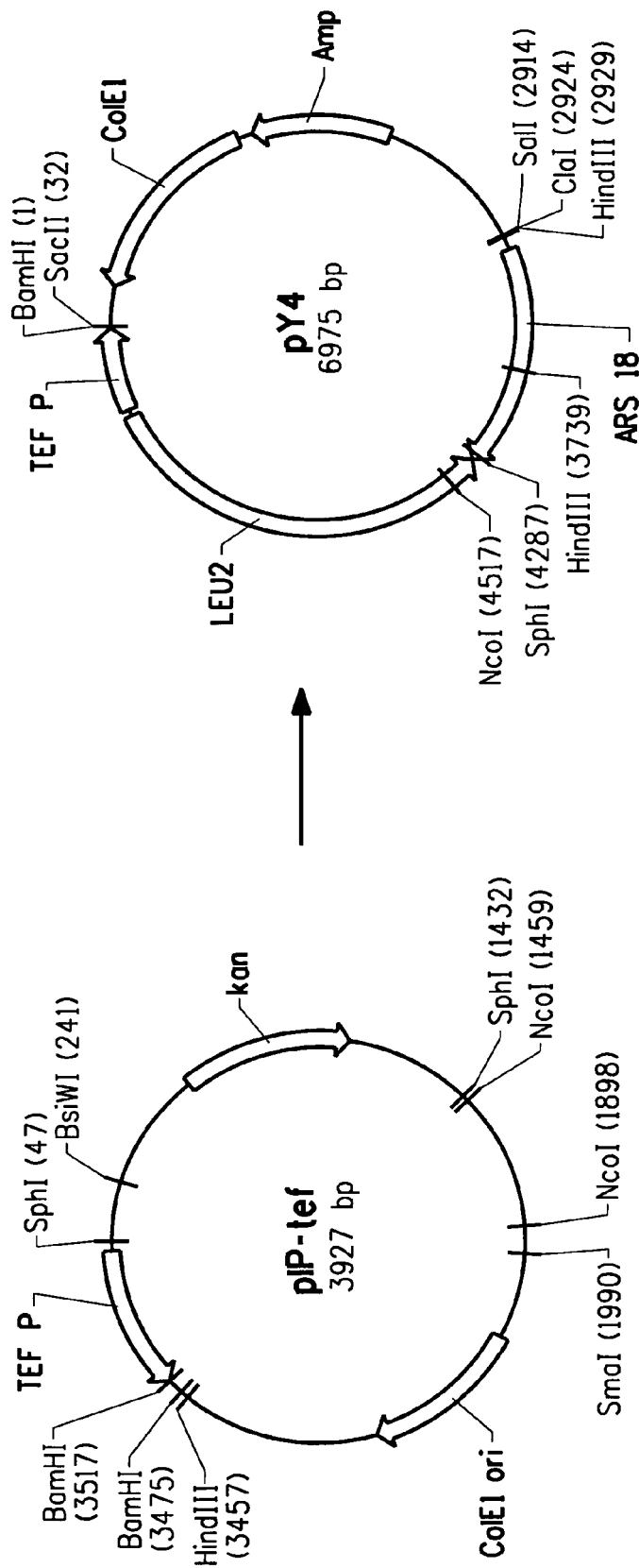
Figure 4C:
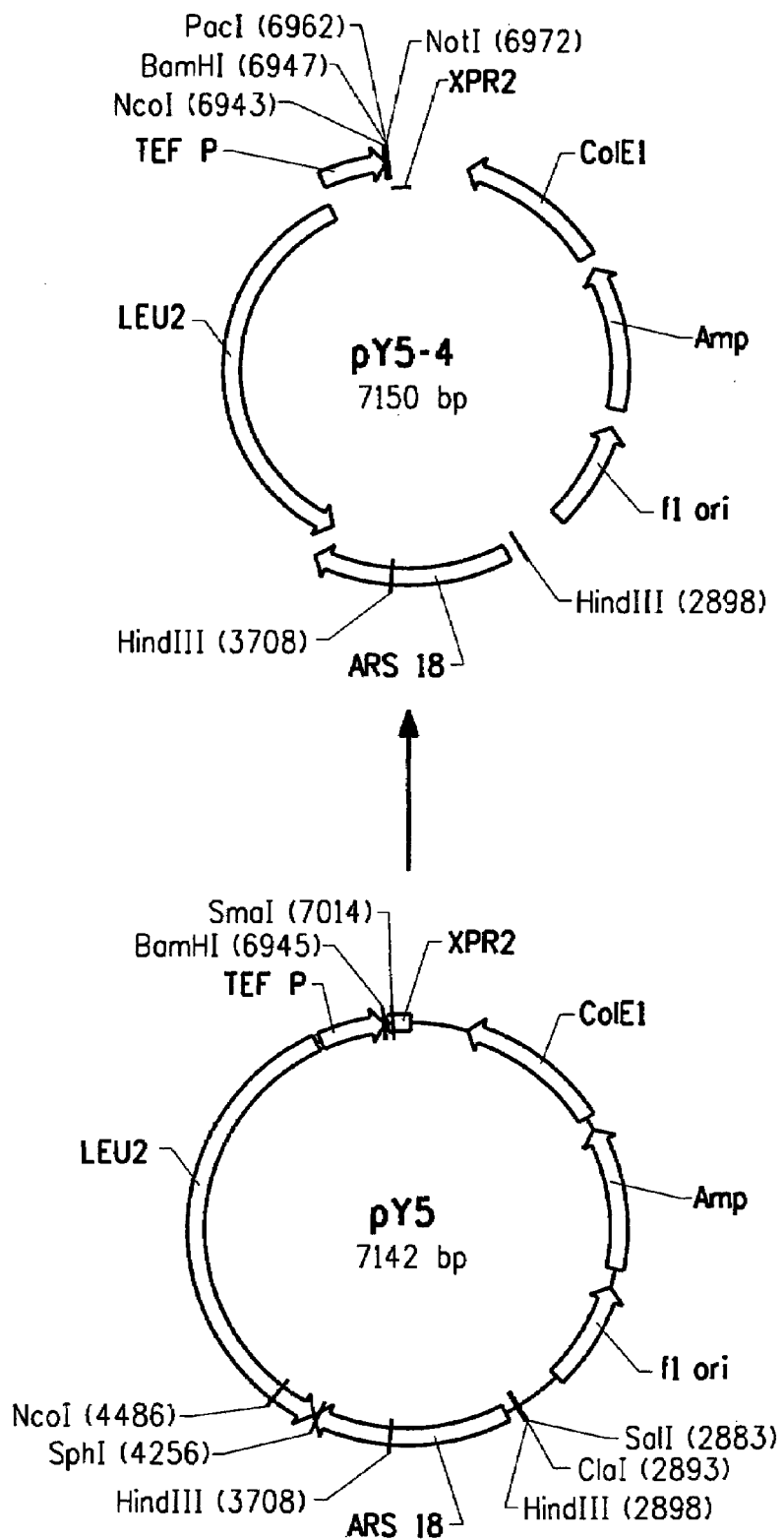

Plasmid pY5–10 was constructed as a derivative of pY5 (FIG. 4). First, pY5–4 (FIG. 4) was constructed by three rounds of site-directed mutagenesis using pY5 as template. A NcoI site located inside the Leu2 reporter gene was eliminated from pY5 using oligonucleotides YL1 and YL2 (SEQ ID NOs:36 and 37, respectively) to generate pY5–1. A NcoI site was introduced into pY5–1 between the TEF promoter and XPR transcriptional terminator by site-directed mutagenesis using oligonucleotides YL3 and YL4 (SEQ ID NOs:38 and 39, respectively) to generate pY5–2. A PacI site was then introduced into pY5–2 between the TEF promoter and XPR transcriptional terminator using oligonucleotides YL23 and YL24 (SEQ ID NOs:40 and 41, respectively) to generate pY5–4. Finally, a SalI site was introduced into pY5–4 between the TEF promoter and the Leu gene by site-directed mutagenesis using oligonucleotides YL9 (SEQ ID NO:42) and YL10 (SEQ ID NO:43) as primers to generate pY5–10 (FIG. 5A).

Synthesis of Plasmid pY5–30

Plasmid pY5–30 (FIG. 5B; SEQ ID NO:62), comprising a TEF promoter::GUS::XPR terminator chimeric gene, was synthesized by inserting the NcoI/PacI PCR product comprising the GUS coding region (supra) into NcoI/PacI digested pY5–10.

Example 4

Synthesis of pDMW212 and pDMW214

The present Example describes the synthesis of pDMW212 (comprising a FBA::GUS::XPR chimeric gene) and pDMW214 (comprising a FBAIN::GUS::XPR chimeric gene, wherein FBAIN is the FBA promoter region along with a portion of the 5' coding region comprising the fba1 intron). Synthesis of these plasmids first required identification and amplification of the putative FBA and FBAIN promoter regions. Then, each putative promoter region was cloned into a derivative of pY5–30 (described in Example 3).

Identification and Amplification of Putative Promoter Regions

After the isolation of the 5' upstream sequence of the fba1 gene by genome-walking, the translation start site was identified by looking for the consensus motif around the translation initiation ATG codon and by comparison of the translated coding region of the *Yarrowia* fba1 gene with the fba1 gene from other organisms. Previous studies had determined that the consensus sequence around the 'ATG' initiation codon in *Yarrowia lipolytica* was 'MAMMATGNHS' (SEQ ID NO:56), wherein the nucleic acid degeneracy code used is as follows: M=A/C; S=C/G; H=A/C/T; and N=A/C/G/T (FIG. 6). Thus, the region upstream of the fba1 gene's ATG start site was used to identify putative promoter regions.

The nucleotide region 5' upstream of the ATG translation initiation site of the fba1 gene (wherein the 'A' nucleotide of the 'ATG' translation initiation codon was designated as +1) was determined to contain the putative promoter region. 520 Base pairs (provided as SEQ ID NO:18) upsteam of the 'ATG' start codon may be enough for full function of the FBA promoter.

The putative promoter regions were amplified by PCR. Specifically, the FBA promoter region (corresponding to the nucleotide region between position −832 to −1 bp of SEQ ID NO:26 for the purposes herein) was amplified with oligonucleotides ODMW314 (SEQ ID NO:44) and YL341 (SEQ ID NO:45) as primers and genomic DNA of *Yarrowia lipolytica* as template. The FBAIN promoter region (exemplified by SEQ ID NO:46, and corresponding to the nucleotide region between position −826 bp to +169 bp around the putative translation initiation site) was amplified with oligonucleotides ODMW320 (SEQ ID NO:47) and ODMW341 (SEQ ID NO:48) as primers and genomic DNA of *Yarrowia lipolytica* as template. The individual PCR amplification reactions were carried out in a 50 µl total volume, comprising: PCR buffer (containing 10 mM KCl, 10 mM $(NH_4)_2SO_4$, 20 mM Tris-HCl (pH 8.75), 2 mM $MgSO_4$, 0.1% Triton X-100), 100 µg/mL BSA (final concentration), 200 µM each deoxyribonucleotide triphosphate, 10 pmole of each primer and 1 µl of Pfu DNA polymerase (Stratagene). The thermocycler conditions were set for 35 cycles at 95° C. for 1 min, 56° C. for 30 sec, 72° C. for 1 min, followed by a final extension at 72° C. for 10 min.

The individual PCR products were purified using a Qiagen PCR purification kit. The FBA promoter region and the FBAIN promoter region were then digested with NcoI and SalI for 1 hr at 37° C. and purified following gel electrophoresis in 1% (w/v) agarose. The NcoI/SalII-digested PCR products were ligated to NcoI/SalI digested pY5–30 vector. Ligated DNA from each reaction was then used to individually transform *E. coli* DH10B. Transformants were selected on LB agar containing ampicillin (100 µg/mL).

Analysis of the plasmid DNA from one transformant containing the FBA promoter region confirmed the presence of the expected plasmid, designated "pDMW212" (FIG. 7A). Thus, this plasmid contained a chimeric gene comprising a FBA promoter, GUS reporter gene and XPR terminator.

Analysis of the plasmid DNA from one transformant containing FBAIN promoter confirmed the presence of the expected plasmid, designated "pDMW214", and comprising a FBAIN promoter::GUS::XPR terminator chimeric gene (FIG. 7B).

Example 5

Synthesis of pYZGDG and pYZGMG

The present Example describes the synthesis of pYZGDG (comprising a GPD promoter::GUS::XPR terminator chimeric gene) and pYZGMG (comprising a GPM promoter::GUS::XPR terminator chimeric gene). Synthesis of these plasmids required amplification of the *Yarrowia lipolytica* GPD and GPM promoter regions (see co-pending U.S. patent application Ser. No. 10/869,630). Then, each promoter region was cloned into a derivative of pY5–30 (described in Example 3).

The GPD promoter (SEQ ID NO:49), corresponding to the nucleotide region between position −966 bp and the ATG translation initiation site of the GPD gene (wherein the 'A' nucleotide of the 'ATG' translation initiation codon was designated as +1), was amplified by PCR using oligonucleotides YL211 (SEQ ID NO:50) and YL212 (SEQ ID NO:51) as primers and genomic DNA of *Yarrowia lipolytica* as template. In a similar manner, the GPM promoter (SEQ ID NO:52), corresponding to the nucleotide region between position −843 bp and the ATG translation initiation site of the GPM gene (wherein the 'A' nucleotide of the 'ATG' translation initiation codon was designated as +1), was amplified with oligonucleotides YL203 (SEQ ID NO:53) and YL204 (SEQ ID NO:54) and genomic DNA.

Each individual PCR amplification reaction was carried out in a 50 µl total volume, comprising: PCR buffer (containing 10 mM KCl, 10 mM $(NH_4)_2SO_4$, 20 mM Tris-HCl (pH 8.75), 2 mM $MgSO_4$, 0.1% Triton X-100), 100 µg/mL BSA (final concentration), 200 µM each deoxyribonucleotide triphosphate, 10 pmole of each primer and 1 µl of Pfu DNA polymerase (Stratagene, San Diego, Calif.). The thermocycler conditions were set for 35 cycles at 95° C. for 1 min, 56° C. for 30 sec and 72° C. for 1 min, followed by a final extension at 72° C. for 10 min.

The individual PCR products were then purified using a Qiagen PCR purification kit and subjected to the following restriction digestions and ligation reactions. Specifically, GPD was completely digested with SalI and then partially digested with NocI. The SalI/NocI fragment was purified following gel electrophoresis in 1% (w/v) agarose and ligated to NocI/SalI digested pY5–30 vector (wherein the NocI/SalI digestion had excised the TEF promoter from the pY5–30 vector backbone). In a similar manner, GPM was digested with NocI and SalI for 1 hr at 37° C. and then purified following gel electrophoresis in 1% (w/v) agarose. The NocI/SalIII-digested PCR product was ligated to NocI/SalI digested pY5–30 vector. Ligated DNA from each reaction was then used to individually transform *E. coli* DH5α. Transformants were selected on LB agar containing ampicillin (100 µg/mL).

Figure 7D:
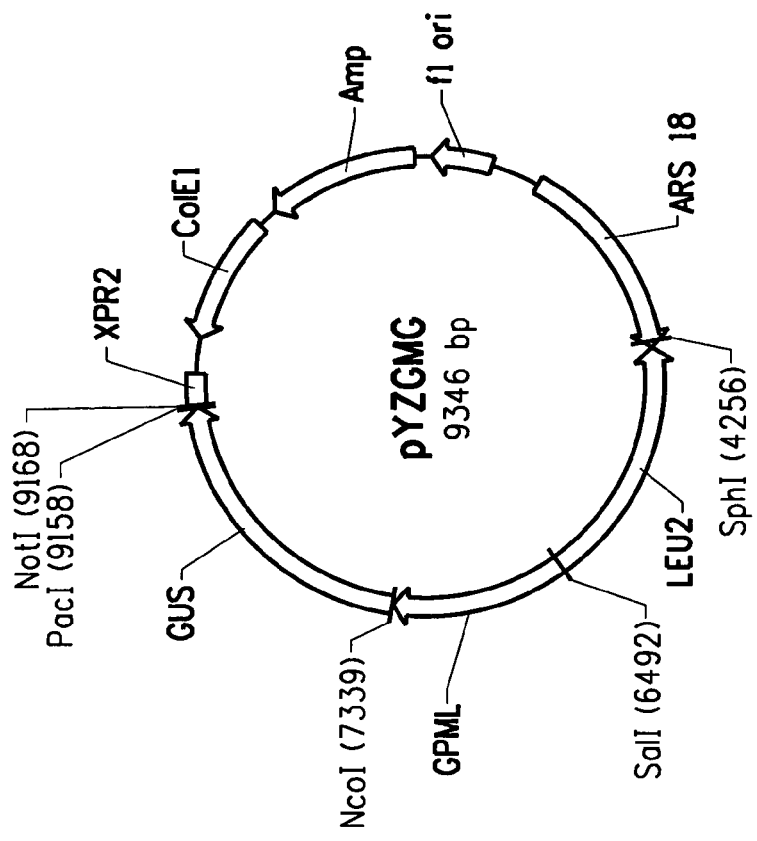
Figure 7C:
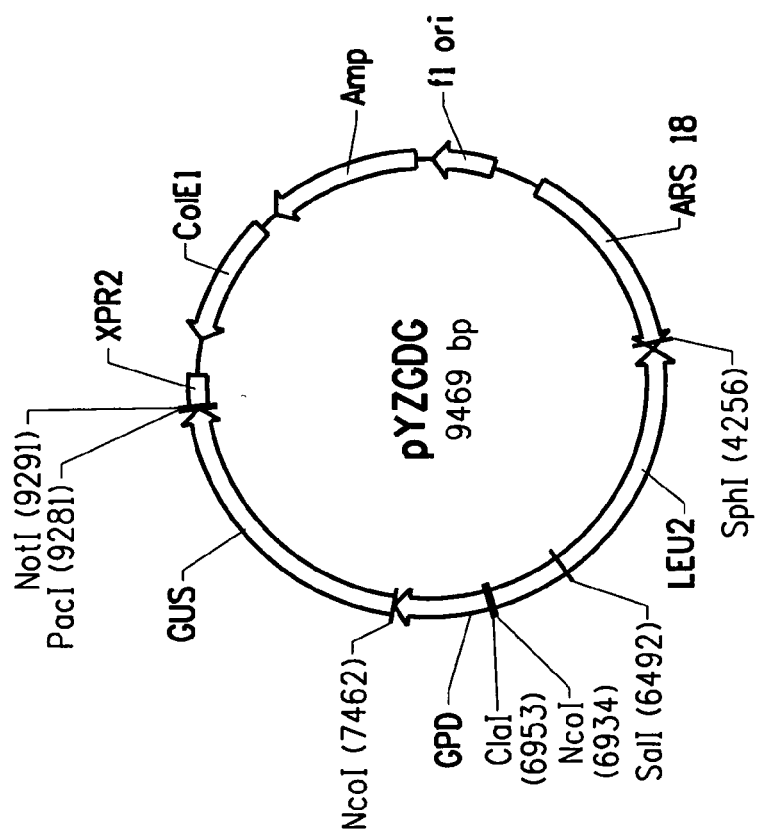

Analysis of the plasmid DNA from one transformant containing GPD confirmed the presence of the expected plasmid, designated "pYZGDG" (FIG. 7C). Thus, this plasmid contained a chimeric gene comprising a GPD promoter, GUS reporter gene and XPR terminator.

Analysis of the plasmid DNA from one transformant containing GPM confirmed the presence of the expected plasmid, designated "pYZGMG", and comprising a GPM::GUS::XPR chimeric gene (FIG. 7D).

Example 6

Transformation of *Y. lipolytica* with pY5–30, pYZGDG, pYZGMG, pDMW212 and pDMW214

The plasmids pY5–30 (Example 3; comprising a TEF::GUS::XPR chimeric gene), pDMW212 (Example 4; comprising a FBA::GUS::XPR chimeric gene), pDMW214 (Example 4; comprising a FBAIN::GUS::XPR chimeric gene), pYZGDG (Example 5; comprising a GPD::GUS::XPR chimeric gene) and pYZGMG (Example 5; comprising a GPM::GUS::XPR chimeric gene) were transformed separately into *Y. lipolytica* ATCC #76982 according to the method of Chen, D. C. et al. (*Appl. Microbiol Biotechnol.* 48(2):232–235 (1997)).

Briefly, a leucine auxotroph of *Yarrowia* was streaked onto a YPD plate and grown at 30° C. for approximately 18 hr. Several large loopfuls of cells were scraped from the plate and resuspended in 1 mL of transformation buffer containing: 2.25 mL of 50% PEG, average MW 3350; 0.125 mL of 2 M Li acetate, pH 6.0; 0.125 mL of 2 M DTT; and 50 µg sheared salmon sperm DNA. Approximately 500 ng of plasmid DNA was incubated in 100 µl of resuspended cells, and maintained at 39° C. for 1 hr with vortex mixing at 15 min intervals. The cells were plated onto minimal media plates lacking leucine and maintained at 30° C. for 2 to 3 days.

Using this technique, transformants were obtained that contained pY5–30, pYZGDG, pYZGMG, pDMW212 and pDMW214.

Example 7

Comparative Analysis of the TEF, GPD, GPM, FBA and FBAIN Promoter Activities in *Yarrowia lipolytica*

The promoter activities of the TEF, GPD, GPM, FBA and FBAIN were determined in *Yarrowia lipolytica* containing the pY5–30, pYZGDG, pYZGMG, pDMW212 and pDMW214 constructs, each of which possessed a GUS reporter gene and an XPR terminator. GUS activity in each expressed construct was measured by histochemical and fluorometric assays (Jefferson, R. A. *Plant Mol. Biol. Reporter* 5:387–405 (1987)).

GUS Activities, Determined by Histochemical Assay

Specifically, *Yarrowia lipolytica* strains containing plasmids pY5–30, pYZGDG, pYZGMG, pDMW212 and pDMW214 were grown from single colonies in 3 mL minimal medium (20 g/L glucose, 1.7 g/L yeast nitrogen base without amino acids, 1 g/L L-proline, 0.1 g/L L-adenine, 0.1 g/L L-lysine, pH 6.1) at 30° C. to an $OD_{600}$~1.0. Then, 100 µl of cells were collected by centrifugation, resuspended in 100 µl of histochemical staining buffer and incubated at 30° C. Staining buffer was prepared by dissolving 5 mg of 5-bromo-4-chloro-3-indolyl glucuronide (X-Gluc) in 50 µl dimethyl formamide, followed by the addition of 5 mL 50 mM $NaPO_4$, pH 7.0.

The results of histochemical staining showed that the TEF promoter in construct pY5–30, the GPD promoter in construct pYZGDG, the GPM promoter in construct pYZGMG, the FBA promoter in construct pDMW212, and the FBAIN promoter in construct pDMW214 were all active. Both the FBA and FBAIN promoters appeared to be much stronger than any of the other promoters, with the FBAIN promoter having the strongest promoter activity (FIG. 8A).

GUS Activities, Determined by Fluorometric Assay

GUS activity was also assayed by fluorometric determination of the production of 4-methylumbelliferone (4-MU) from the corresponding substrate β-glucuronide (Jefferson, R. A. *Plant Mol. Biol. Reporter* 5:387–405 (1987)).

*Yarrowia lipolytica* strains containing plasmids pY5–30, pYZGDG, pYZGMG, pDMW212 and pDMW214 were grown from single colonies in 3 mL minimal medium (as described above) at 30° C. to an $OD_{600}$~1.0. Then, the 3 mL cultures were each added to a 500 mL flask containing 50 mL minimal medium and grown in a shaking incubator at 30° C. for about 24 hrs. The cells were collected by centrifugation, resuspended in Promega Cell Lysis Buffer and lysed using the BIO 101 Biopulverizer system (Vista, Calif.). After centrifugation, the supernatants were removed and kept on ice.

For each fluorometric assay, 100 µl of extract was added to 700 µl of GUS assay buffer (2 mM 4-methylumbelliferyl-β-D-glucuronide ("MUG") in extraction buffer) and placed at 37° C. Aliquots of 100 µl were taken at 0, 30 and 60 min time points and added to 900 µl of stop buffer (1 M $Na_2CO_3$). Each time point was read using a CytoFluor Series 4000 Fluorescence Multi-Well Plate Reader (PerSeptive Biosystems, Framingham, Mass.) set to an excitation wavelength of 360 nm and an emission wavelength of 455 nm. Total protein concentration of each sample was determined using 10 µl of extract and 200 µl of BioRad Bradford reagent (Bradford, M. M. *Anal. Biochem.* 72:248–254 (1976)). GUS activity was expressed as nmoles of 4-MU per minute per mg of protein.

Results of these fluorometric assays are shown in FIG. 8B. Specifically, the FBA promoter was 2.2 times stronger than the GPD promoter in *Y. lipolytica*. Additionally, the GUS activity of the FBAIN promoter was about 6.6 times stronger than the GPD promoter.

Example 8

Quantitative Comparison of the Transcriptional Activities of the TEF, GPD, FBA and FBAIN Promoters in *Yarrowia lipolytica*

The transcriptional activities of the TEF, GPD, FBA and FBAIN promoters were determined in *Y. lipolytica* containing the pY5–30, pYZGDG, pDMW212 and pDMW214 constructs by quantitative PCR analyses. This required isolation of RNA and real time RT-PCR.

More specifically, *Y. lipolytica* strains containing each plasmid above were grown from single colonies in 6 mL of minimal media (20 g/L glucose, 1.7 g/L yeast nitrogen base without amino acids, 1 g/L L-proline, 0.1 g/L L-adenine, 0.1 g/L L-lysine, pH 6.1) in 25 mL Erlenmeyer flasks for 16 hrs at 30° C. Each of the 6 mL starter cultures was then added to individual 500 mL flasks containing 140 mL high glucose media (14 g/L $KH_2PO_4$, 4 g/L $K_2HPO_4$, 2 g/L $MgSO_4 \cdot 7H_2O$, 80 g/L glucose, pH 6.5) and incubated at 30° C. for 4 days. In each interval of 24 hrs, 1 mL of each culture was removed from each flask to measure the optical density, 27 mL was removed and used for a fluorometric GUS assay (as described in Example 7), and two aliquots of 1.5 mL were removed for RNA isolation. The culture for RNA isolation was centrifuged to produce a cell pellet.

RNA Isolation

The RNA was isolated from *Yarrowia* strains according to the modified Qiagen RNeasy mini protocol (Qiagen, San Diego, Calif.). Briefly, at each time point for each sample, 340 µL of Qiagen's buffer RLT was used to resuspend each of the two cell pellets. The buffer RLT/cell suspension mixture from each of the two tubes was combined in a bead beating tube (Bio101, San Diego, Calif.). About 500 µL of 0.5 mL glass beads was added to the tube and the cells were disrupted by bead beating 2 min at setting 5 (BioPulverizer, Bio101 Company, San Diego, Calif.). The disrupted cells were then pelleted by centrifugation at 14,000 rpm for 1 min and 350 µl of the supernatent was transferred to a new microcentrifuge tube. Ethanol (350 µL of 70%) was added to each homogenized lysate. After gentle mixing, the entire sample was added to a RNeasy mini column in a 2 mL collection tube. The sample was centrifuged for 15 sec at 10,000 rpm. Buffer RW1 (350 µL) was added to the RNeasy mini column and the column was centrifuged for 15 sec at 10,000 rpm to wash the cells. The eluate was discarded. Qiagen's DNase1 stock solution (10 µL) was added to 70 µl of Buffer RDD and gently mixed. This entire DNase solution was added to the RNeasy mini column and incubated at room temperature for 15 min. After the incubation step, 350

μL of Buffer RW1 was added to the mini column and the column was centrifuged for 15 sec at 10,000 rpm. The column was washed twice with 700 μL Buffer RW1. RNase-free water (50 μL) was added to the column. The column was centrifuged for 1 min at 10,000 rpm to elute the RNA.

Real Time RT-PCR Analysis

A two-step RT-PCR protocol was used, wherein total *Yarrowia* RNA was first converted to cDNA and then the cDNA was analyzed using Real Time PCR. The conversion to cDNA was performed using Applied Biosystems' High Capacity cDNA Archive Kit (PN #4322171; Foster City, Calif.) and Molecular Biology Grade water from MediaTech, Inc. (PN# 46–000-Con; Holly Hill, Fla.). Total RNA from *Yarrowia* (100 ng) was converted to cDNA by combining it with 10 μl of RT buffer, 4 μl of 25× dNTPs, 10 μl 10× Random Hexamer primers, 5 μl Multiscribe Reverse Transcriptase and 0.005 μl RNase Inhibitor, and brought to a total reaction volume of 100 μl with water. The reactions were incubated in a thermocycler for 10 min at 25° C. followed by 2 hrs at 37° C. The cDNA was stored at −20° C. prior to Real Time analysis.

Real Time analysis was performed using the SYBR Green PCR Master Mix from Applied Biosystems (PN#4309155). The Reverse Transcription reaction (2 μl) was added to 10 μl of 2× SYBR PCR Mix, 0.2 μl of 100 μM Forward and Reverse primers for either URA (i.e., primers YL-URA-16F [SEQ ID NO:57] and YL-URA-78R [SEQ ID NO:58]) or GUS (i.e., primers GUS-767F [SEQ ID NO:59] and GUS-891R [SEQ ID NO:60]) and 7.2 μl water. The reactions were thermocycled for 10 min at 95° C. followed by 40 cycles of 95° C. for 5 sec and 60° C. for 1 min in an ABI 7900 Sequence Detection System instrument. Real time fluorescence data was collected during the 60° C. extension during each cycle.

Relative quantitation was performed using the ΔΔCT method as per User Bulletin #2: "Relative Quantitation of Gene Expression", Applied Biosystems, Updated October 2001. The URA gene was used for normalization of GUS expression. In order to validate the use of URA as a normalizer gene, the PCR efficiency of GUS and URA were compared and they were found to be 1.04 and 0.99, respectively (where 1.00 equals 100% efficiency). Since the PCR efficiencies were both near 100%, the use of URA as a normalizer for GUS expression was validated, as was the use of the ΔΔCT method for expression quantitation. The normalized quantity is referred to as the ΔCT.

The GUS mRNA in each different strain (i.e., *Y. lipolytica* containing the pYZGDG, pDMW212 and pDMW214 constructs) was quantified to the mRNA level of the *Y. lipolytica* strain with pY5–30 (i.e., TEF::GUS). Thus, relative quantitation of expression was calculated using the mRNA level of the strain with TEF::GUS as the reference sample. The normalized value for GPD::GUS, FBA::GUS and FBAIN::GUS was compared to the normalized value of the TEF::GUS reference. This quantity is referred to as the ΔΔCT. The ΔΔCT values were then converted to absolute values by utilizing the formula $2^{-\Delta\Delta CT}$. These values refer to the fold increase in the mRNA level of GUS in the strains comprising the chimeric GPD::GUS, FBA::GUS and FBAIN::GUS genes, as compared to the chimeric TEF::GUS gene. Using this methodology, it was possible to compare the activity of the TEF promoter to the GPD, FBA and FBAIN promoters.

The results of the relative quantitation of mRNA for each GUS chimeric gene are shown in FIG. 8C. More specifically, the assay showed that after 24 hrs in high glucose media, the transcription activity of the FBA and FBAIN promoters was about 3.3 and 6 times stronger than the TEF promoter, respectively. Similarly, the transcription activity of the GPD promoter is about 2 times stronger than the TEF promoter. While the transcription activities of the chimeric FBA:: GUS, FBAIN::GUS and GPD::GUS gene fusions decreased over the 4 day period of the experiment, the transcriptional activity of the FBAIN promoter was still about 3 times stronger than the TEF promoter in the final day of the experiment.

Example 9

Confirmation of the Presence of Enhancers within the fba1 Intron

The present Example describes construction of a chimeric promoter that was generated to drive expression of the GUS reporter gene, in order to confirm the presence of an enhancer located within the intron of the fba1 gene. This chimeric promoter thus consisted of a GPM::FBAIN promoter fusion.

The chimeric promoter is described below in Table 3 and is designated herein as "GPM::FBAIN". The chimeric promoter provided as SEQ ID NO:61 consisted of the complete GPM promoter, plus an additional component comprising the intron of the fba1 gene.

TABLE 3

Construction of A Chimeric Promoter

| Chimeric Promoter | Component 1 | Component 2 | SEQ ID NO |
|---|---|---|---|
| GPM::FBAIN | −1 to −843 region of GPM | +1 to +171 region of FBAIN, wherein the intron is located from +62 to +165 | 61 |

The chimeric promoter was then positioned such that it drove expression of the GUS reporter gene in the pY5–30 vector backbone (wherein the TEF promoter had been removed). Specifically, pDMW224 (FIG. 9A) contained a chimeric gene comprising the chimeric GPM::FBAIN promoter, GUS and the XPR terminator.

The activity of the GPM::FBAIN promoter was compared with the TEF, FBAIN and GPM promoters by comparing the GUS activity in the *Y. lipolytica* strain comprising pDMW224 relative to the GUS activity in *Y. lipolytica* strains comprising pY5–30, pDMW214 and pYZGMG constructs, respectively. As in previous Examples, this direct comparison was possible, since each strain possessed a different promoter but the same GUS reporter gene and XPR terminator. GUS activity in each expressed construct was measured by histochemical assays (supra, Example 7).

Results of these histochemical assays are shown in FIG. 9B. As previously determined, the FBAIN promoter was the strongest promoter. However, the chimeric GPM::FBAIN promoter was much stronger than the GPM promoter. Thus, this confirmed the existence of an enhancer in the fba1 intron (SEQ ID NO:55).

Example 10

Production of DGLA in *Yarrowia lipolytica* Using Chimeric Genes Constructed with the FBA and FBAIN Promoters Construct pKUNF12T6E (FIG. 9C; SEQ ID NO:63) was generated to integrate four chimeric genes (comprising a Δ12 desaturase, a Δ6 desaturase and 2 elongases) into the Ura3 loci of wild type *Yarrowia* strain ATCC #20362, to thereby enable production of DGLA. The pKUNF12T6E plasmid contained the following components:

TABLE 4

Description of Plasmid pKUNF12T6E (SEQ ID NO: 63)

| RE Sites And Nucleotides Within SEQ ID NO: 63 | Description Of Fragment And Chimeric Gene Components |
|---|---|
| AscI/BsiWI (9420-8629) | 784 bp 5' part of *Yarrowia* Ura3 gene (GenBank Accession No. AJ306421) |
| SphI/PacI (12128-1) | 516 bp 3' part of *Yarrowia* Ura3 gene (GenBank Accession No. AJ306421) |
| SwaI/BsiWI (6380-8629) | FBAIN::EL1S::Pex20, comprising: FBAIN: FBAIN promoter EL1S: codon-optimized elongase 1 gene (SEQ ID NO: 64), derived from *Mortierella alpina* (GenBank Accession No. AX464731) Pex20: Pex20 terminator sequence from *Yarrowia* Pex20 gene (GenBank Accession No. AF054613) |
| BglII/SwaI (4221-6380) | TEF::Δ6S::Lip1, comprising: TEF: TEF promoter (GenBank Accession No. AF054508) Δ6S: codon-optimized Δ6 desaturase gene (SEQ ID NO: 66), derived from *Mortierella alpina* (GenBank Accession No. AF465281) Lip1: Lip1 terminator sequence from *Yarrowia* Lip1 gene (GenBank Accession No. Z50020) |
| PmeI/ClaI (4207-1459) | FBA::F.Δ12::Lip2, comprising: FBA: FBA promoter F.Δ12: *Fusarium moniliforme* Δ12 desaturase gene (SEQ ID NO: 68) Lip2: Lip2 terminator sequence from *Yarrowia* Lip2 gene (GenBank Accession No. AJ012632) |
| ClaI/PacI (1459-1) | TEF::EL2S::XPR, comprising: TEF: TEF promoter (GenBank Accession No. AF054508) EL2S: codon-optimized elongase gene (SEQ ID NO: 70), derived from *Thraustochytrium aureum* (U.S. Pat. No. 6,677,145) XPR: XPR terminator sequence of *Yarrowia* Xpr gene (GenBank Accession No. M17741) |

The pKUNF12T6E plasmid was digested with AscI/SphI, and then used for transformation of wild type *Y. lipolytica* ATCC #20362 (as described in Example 6). The transformant cells were plated onto 5-fluorouracil-6-carboxylic acid monohydrate ("FOA") selection media plates (0.17% yeast nitrogen base (DIFCO Laboratories, Detroit, Mich.) without ammonium sulfate or amino acids, 2% glucose, 0.1% proline, 75 mg/L uracil, 75 mg/L uridine, 20 g/L agar and 800 mg/L FOA (Zymo Research Corp., Orange, Calif. 92867)) and maintained at 30° C. for 2 to 3 days. The FOA resistant colonies were picked and streaked onto selection plates comprising either minimal media (20 g/L glucose, 1.7 g/L yeast nitrogen base without amino acids, 1 g/L L-proline, 0.1 g/L L-adenine, 0.1 g/L L-lysine, pH 6.1) or minimal media plus 0.01% uracil ("MMU"). The colonies that could grow on MMU plates but not on the minimal media plates were selected as Ura-strains. Single colonies of Ura-strains were then inoculated into liquid MMU at 30° C. and shaken at 250 rpm/min for 2 days.

For fatty acid analysis, cells were collected by centrifugation and lipids were extracted as described in Bligh, E. G. & Dyer, W. J. (*Can. J. Biochem. Physiol.* 37:911–917 (1959)). Fatty acid methyl esters were prepared by transesterification of the lipid extract with sodium methoxide (Roughan, G., and Nishida I. *Arch Biochem Biophys.* 276 (1):3846 (1990)) and subsequently analyzed with a Hewlett-Packard 6890 GC fitted with a 30-m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water, and dried under vacuum in a Speed-Vac for 5–10 min. Sodium methoxide (100 μl of 1%) was added to the sample, and then the sample was vortexed and rocked for 20 min. After adding 3 drops of 1 M NaCl and 400 μl hexane, the sample was vortexed and spun. The upper layer was removed and analyzed by GC as described above.

GC analyses showed the presence of DGLA in the transformants containing the 4 chimeric genes of pKUNF12T6E (FIG. 9C), but not in the wild type *Yarrowia* control strain. Most of the selected 32 Ura-strains produced about 6% DGLA of total lipids. There were 2 strains that produced about 8% DGLA of total lipids.

SEQUENCE LISTING

```
<160> NUMBER OF SEQ ID NOS: 72

<210> SEQ ID NO 1
<211> LENGTH: 359
<212> TYPE: PRT
<213> ORGANISM: Saccharomyces cerevisiae (GenBank Accession NP_012863)

<400> SEQUENCE: 1

Met Gly Val Glu Gln Ile Leu Lys Arg Lys Thr Gly Val Ile Val Gly
1               5                   10                  15

Glu Asp Val His Asn Leu Phe Thr Tyr Ala Lys Glu His Lys Phe Ala
            20                  25                  30

Ile Pro Ala Ile Asn Val Thr Ser Ser Thr Ala Val Ala Ala Leu
        35                  40                  45

Glu Ala Ala Arg Asp Ser Lys Ser Pro Ile Ile Leu Gln Thr Ser Asn
    50                  55                  60
```

Gly Gly Ala Ala Tyr Phe Ala Gly Lys Gly Ile Ser Asn Glu Gly Gln
65                  70                  75                  80

Asn Ala Ser Ile Lys Gly Ala Ile Ala Ala His Tyr Ile Arg Ser
            85                  90                  95

Ile Ala Pro Ala Tyr Gly Ile Pro Val Val Leu His Ser Asp His Cys
                100                 105                 110

Ala Lys Lys Leu Leu Pro Trp Phe Asp Gly Met Leu Glu Ala Asp Glu
            115                 120                 125

Ala Tyr Phe Lys Glu His Gly Glu Pro Leu Phe Ser Ser His Met Leu
            130                 135                 140

Asp Leu Ser Glu Glu Thr Asp Glu Glu Asn Ile Ser Thr Cys Val Lys
145                 150                 155                 160

Tyr Phe Lys Arg Met Ala Ala Met Asp Gln Trp Leu Glu Met Glu Ile
                165                 170                 175

Gly Ile Thr Gly Gly Glu Glu Asp Gly Val Asn Asn Glu Asn Ala Asp
                180                 185                 190

Lys Glu Asp Leu Tyr Thr Lys Pro Glu Gln Val Tyr Asn Val Tyr Lys
            195                 200                 205

Ala Leu His Pro Ile Ser Pro Asn Phe Ser Ile Ala Ala Phe Gly
            210                 215                 220

Asn Cys His Gly Leu Tyr Ala Gly Asp Ile Ala Leu Arg Pro Glu Ile
225                 230                 235                 240

Leu Ala Glu His Gln Lys Tyr Thr Arg Glu Gln Val Gly Cys Lys Glu
                245                 250                 255

Glu Lys Pro Leu Phe Leu Val Phe His Gly Ser Gly Ser Thr Val
            260                 265                 270

Gln Glu Phe His Thr Gly Ile Asp Asn Gly Val Val Lys Val Asn Leu
            275                 280                 285

Asp Thr Asp Cys Gln Tyr Ala Tyr Leu Thr Gly Ile Arg Asp Tyr Val
290                 295                 300

Leu Asn Lys Lys Asp Tyr Ile Met Ser Pro Val Gly Asn Pro Glu Gly
305                 310                 315                 320

Pro Glu Lys Pro Asn Lys Lys Phe Phe Asp Pro Arg Val Trp Val Arg
                325                 330                 335

Glu Gly Glu Lys Thr Met Gly Ala Lys Ile Thr Lys Ser Leu Glu Thr
                340                 345                 350

Phe Arg Thr Thr Asn Thr Leu
            355

<210> SEQ ID NO 2
<211> LENGTH: 358
<212> TYPE: PRT
<213> ORGANISM: Schizosaccharomyces pombe (GenBank Accession No. NP_595692)

<400> SEQUENCE: 2

Met Gly Ile Leu Asp Ile Val Pro Thr Gly Val Ile Thr Gly Asp Asn
1               5                   10                  15

Val Leu Lys Leu Phe Thr Tyr Ala Arg Glu His Gly Phe Ala Ile Pro
            20                  25                  30

Ala Ile Asn Val Thr Ser Ser Thr Ala Ile Ala Leu Glu Ala
            35                  40                  45

Ala Arg Glu Ala Arg Ser Pro Ile Ile Leu Gln Thr Ser Asn Gly Gly
50                  55                  60

```
Ala His Phe Phe Ala Gly Lys Glu Ser Ser Asn Glu Gly Gln Lys Ala
 65                  70                  75                  80

Ser Ile Ala Gly Ser Ile Ala Ala His Tyr Ile Arg Ser Ile Ala
             85                  90                  95

Pro Phe Phe Gly Val Pro Val Val Met His Ser Asp His Cys Ala Lys
            100                 105                 110

Lys Leu Leu Pro Trp Met Asp Gly Met Phe Glu Ala Asp Glu Ala Tyr
            115                 120                 125

Phe Lys Ile His Gly Glu Pro Leu Phe Ser Ser His Met Leu Asp Leu
            130                 135                 140

Ser Glu Glu Pro Lys Lys Glu Asn Ile Ala Gln Val Lys Glu Tyr Cys
145                 150                 155                 160

Lys Arg Ala Val Pro Met Lys Ile Trp Ile Glu Met Glu Ile Gly Ile
                165                 170                 175

Thr Gly Gly Glu Glu Asp Gly Val Asp Asn Ser His Val Ser His Thr
            180                 185                 190

Glu Leu Tyr Thr Gln Pro Glu Asp Ile Trp Asp Val Tyr Arg Glu Leu
            195                 200                 205

Ser Ser Val Thr Pro Tyr Phe Ser Ile Ala Ala Ala Phe Gly Asn Val
210                 215                 220

His Gly Val Tyr Lys Pro Gly Asn Val Lys Leu Gln Pro Ala Leu Leu
225                 230                 235                 240

Gly Gln His Gln Ala Tyr Val Lys Glu Gln Leu Lys Thr Thr Asn Asp
                245                 250                 255

Lys Pro Val Phe Phe Val Phe His Gly Gly Ser Gly Ser Ser Val Asn
            260                 265                 270

Glu Phe Arg Thr Gly Ile Lys Cys Gly Val Val Lys Val Asn Ile Asp
            275                 280                 285

Thr Asp Thr Gln Phe Ala Tyr Val Glu Gly Val Arg Asp Tyr Val Leu
290                 295                 300

Lys Tyr Lys Asp Tyr Leu Met Thr Pro Val Gly Asn Pro Glu Gly Ala
305                 310                 315                 320

Asp Lys Pro Asn Lys Lys Phe Asp Pro Arg Val Trp Ile His Glu
                325                 330                 335

Gly Glu Lys Thr Met Thr Lys Arg Val Leu Thr Ala Leu Glu Asp Phe
            340                 345                 350

Tyr Thr Val Asn Thr Leu
            355

<210> SEQ ID NO 3
<211> LENGTH: 362
<212> TYPE: PRT
<213> ORGANISM: Aspergillus oryzae (GenBank Accession No. BAB12232)

<400> SEQUENCE: 3

Met Gly Val Gly Val Leu Glu Lys Leu Ser Arg Lys Thr Gly Val Ile
  1               5                  10                  15

Val Gly Asp Asp Val Leu Arg Leu Phe Glu His Ala Gln Gln Asn Asn
             20                  25                  30

Tyr Ala Ile Pro Ala Val Asn Val Thr Ser Ser Thr Val Val Ala
         35                  40                  45

Ser Leu Glu Ala Ala Arg Asp Gln Asn Cys Pro Ile Val Leu Gln Leu
 50                  55                  60

Ser Gln Gly Gly Ala Ala Tyr Phe Ala Gly Lys Gly Val Ser Asn Asp
 65                  70                  75                  80
```

```
Gly Gln Gln Ala Pro Leu Pro Val Val Ser Leu Leu Pro Thr Thr Ser
                85                  90                  95

Val Ala Leu Leu Pro Pro Thr Val Ser Leu Leu Ser Phe Thr Pro Thr
                100                 105                 110

Thr Ala Pro Arg Ser Ser Ser Leu Gly Ser Met Ala Ser Ser Thr Arg
                115                 120                 125

Met Ser Ala Thr Ser Ser Ser Thr Ala Ser Pro Phe Phe Ser Ser His
                130                 135                 140

Met Ile Asp Leu Ser Glu Glu Pro Val Asp Tyr Asn Ile Gln Thr Thr
145                 150                 155                 160

Ala Ala Tyr Leu Lys Arg Ala Ala Pro Met Lys Gln Trp Leu Glu Met
                165                 170                 175

Glu Ile Gly Ile Thr Gly Gly Glu Asp Gly Val Asn Asn Glu Asp
                180                 185                 190

Val Asp Asn Asn Ser Leu Tyr Thr Gln Pro Glu Asp Ile Leu Ala Ile
                195                 200                 205

His Lys Ala Leu Ser Pro Ile Ser Pro Tyr Phe Ser Ile Ala Ala Gly
    210                 215                 220

Phe Gly Asn Val His Gly Val Tyr Lys Pro Gly Asn Val Lys Leu His
225                 230                 235                 240

Pro Glu Leu Leu Lys Lys His Gln Ala Tyr Val Lys Glu Lys Ile Gly
                245                 250                 255

Ser Asn Lys Asp Lys Pro Val Phe Phe Val Phe His Gly Gly Ser Gly
                260                 265                 270

Ser Ser Lys Glu Glu Tyr Lys Glu Ala Ile Ser Tyr Gly Val Val Lys
                275                 280                 285

Val Asn Val Asp Thr Asp Met Gln Phe Ala Tyr Met Ser Gly Ile Arg
    290                 295                 300

Asp Tyr Ile Leu Lys Lys Asp Tyr Leu Met Thr Ala Val Gly Asn
305                 310                 315                 320

Pro Glu Gly Glu Asp Lys Pro Asn Lys Lys Ser Phe Asp Pro Arg Val
                325                 330                 335

Trp Val Arg Glu Gly Glu Lys Thr Met Ser Gln Arg Val Lys Val Ala
                340                 345                 350

Leu Glu Asp Phe Asn Thr Ala Gly Gln Leu
                355                 360

<210> SEQ ID NO 4
<211> LENGTH: 359
<212> TYPE: PRT
<213> ORGANISM: Haemophilus influenzae (GenBank Accession NP_438682)

<400> SEQUENCE: 4

Met Ala Lys Leu Leu Asp Ile Val Lys Pro Gly Val Val Thr Gly Glu
1               5                   10                  15

Asp Val Gln Lys Val Phe Ala Tyr Ala Lys Glu His Asn Phe Ala Ile
                20                  25                  30

Pro Ala Val Asn Cys Val Gly Ser Asp Ser Val Asn Ala Val Leu Glu
                35                  40                  45

Thr Ala Ala Arg Val Lys Ala Pro Val Ile Ile Gln Phe Ser Asn Gly
            50                  55                  60

Gly Ala Ala Phe Tyr Ala Gly Lys Gly Ile Lys Pro Thr Ser Gly Thr
65              70                  75                  80

Arg Pro Asp Val Leu Gly Ala Ile Ala Gly Ala Lys Gln Val His Thr
```

```
                    85                  90                  95
Leu Ala Lys Glu Tyr Gly Val Pro Val Ile Leu His Thr Asp His Ala
                100                 105                 110

Ala Lys Lys Leu Leu Pro Trp Ile Asp Gly Leu Leu Asp Ala Gly Glu
            115                 120                 125

Lys His Phe Ala Glu Thr Gly Arg Pro Leu Phe Ser Ser His Met Ile
        130                 135                 140

Asp Leu Ser Glu Glu Ser Met Glu Glu Asn Met Ala Ile Cys Arg Glu
145                 150                 155                 160

Tyr Leu Ala Arg Met Asp Lys Met Gly Met Thr Leu Glu Ile Glu Ile
                165                 170                 175

Gly Ile Thr Gly Gly Glu Glu Asp Gly Val Asp Asn Ser Asp Val Asp
                180                 185                 190

Glu Ser Arg Leu Tyr Thr Gln Pro Ser Asp Val Leu Tyr Val Tyr Asp
            195                 200                 205

Gln Leu His Pro Val Ser Pro Asn Phe Thr Val Ala Ala Ala Phe Gly
        210                 215                 220

Asn Val His Gly Val Tyr Lys Pro Gly Asn Val Lys Leu Lys Pro Ser
225                 230                 235                 240

Ile Leu Gly Glu Ser Gln Glu Phe Val Ser Lys Glu Arg Asn Leu Pro
                245                 250                 255

Ala Lys Pro Ile Asn Phe Val Phe His Gly Ser Gly Ser Ser Arg
                260                 265                 270

Glu Glu Ile Arg Glu Ala Ile Gly Tyr Gly Ala Ile Lys Met Asn Ile
            275                 280                 285

Asp Thr Asp Thr Gln Trp Ala Ser Trp Asn Gly Ile Leu Asn Phe Tyr
        290                 295                 300

Lys Ala Asn Glu Ala Tyr Leu Gln Gly Gln Leu Gly Asn Pro Glu Gly
305                 310                 315                 320

Pro Asp Ala Pro Asn Lys Lys Tyr Tyr Asp Pro Arg Val Trp Leu Arg
                325                 330                 335

Lys Met Glu Glu Ser Met Ser Lys Arg Leu Glu Gln Ser Phe Glu Asp
            340                 345                 350

Leu Asn Cys Val Asp Val Leu
        355

<210> SEQ ID NO 5
<211> LENGTH: 359
<212> TYPE: PRT
<213> ORGANISM: Pasteurella multocida (GenBank Accession NP_246800)

<400> SEQUENCE: 5

Met Ala L

```
Leu Ala Glu Glu Tyr Gly Val Pro Val Ile Leu His Thr Asp His Ala
                100                 105                 110

Ala Lys Lys Leu Leu Pro Trp Ile Asp Gly Leu Leu Glu Ala Gly Glu
            115                 120                 125

Glu His Phe Ala Glu Thr Gly Lys Pro Leu Phe Ser Ser His Met Ile
        130                 135                 140

Asp Leu Ser Glu Glu Pro Met Glu Asn Met Ala Ile Cys Arg Glu
145                 150                 155                 160

Tyr Leu Ala Arg Met Asp Lys Met Gly Met Thr Leu Glu Ile Glu Ile
                165                 170                 175

Gly Ile Thr Gly Gly Glu Asp Gly Val Asp Asn Ser Asp Val Glu
            180                 185                 190

Glu Ser Lys Leu Tyr Thr Gln Pro Glu Asp Val Leu Tyr Val Tyr Asp
        195                 200                 205

Gln Leu Asn Pro Val Ser Pro Arg Phe Thr Val Ala Ala Ala Phe Gly
    210                 215                 220

Asn Val His Gly Val Tyr Lys Pro Gly Asn Val Lys Leu Lys Pro Ser
225                 230                 235                 240

Ile Leu Gly Ala Ser Gln Glu Phe Val Ser Lys Glu Arg Gly Leu Pro
                245                 250                 255

Ala Lys Ser Ile Asp Phe Val Phe His Gly Ser Gly Ser Ser Arg
            260                 265                 270

Glu Glu Ile Arg Glu Ala Ile Ser Tyr Gly Ala Ile Lys Met Asn Ile
        275                 280                 285

Asp Thr Asp Thr Gln Trp Ala Ser Trp Glu Gly Ile Leu Lys Phe Tyr
    290                 295                 300

Asn Ala Asn Gln Asp Tyr Leu Gln Gly Gln Leu Gly Asn Pro Glu Gly
305                 310                 315                 320

Pro Asp Ala Pro Asn Lys Lys Tyr Tyr Asp Pro Arg Val Trp Leu Arg
                325                 330                 335

Lys Met Glu Glu Ser Met Ser Lys Arg Leu Glu Gln Ser Phe Glu Asp
            340                 345                 350

Leu Asn Cys Ile Asp Val Leu
        355

<210> SEQ ID NO 6
<211> LENGTH: 7
<212> TYPE: PRT
<213> ORGANISM: Yarrowia lipolytica

<400> SEQUENCE: 6

Ala Ile Pro Ala Val Asn Val
1               5

<210> SEQ ID NO 7
<211> LENGTH: 7
<212> TYPE: PRT
<213> ORGANISM: Yarrowia lipolytica

<400> SEQUENCE: 7

Glu Met Glu Ile Gly Ile Thr
1               5

<210> SEQ ID NO 8
<211> LENGTH: 20
<212> TYPE: DNA
<213> ORGANISM: Artificial Sequence
<220> FEATURE:
```

<223> OTHER INFORMATION: Primer YL214

<400> SEQUENCE: 8
aagtacgayt cbacycaygg                                          20

<210> SEQ ID NO 9
<211> LENGTH: 20
<212> TYPE: DNA
<213> ORGANISM: Artificial Sequence
<220> FEATURE:
<223> OTHER INFORMATION: Primer YL216

<400> SEQUENCE: 9
acrgccttrg crgcdccrgt                                          20

<210> SEQ ID NO 10
<211> LENGTH: 436
<212> TYPE: DNA
<213> ORGANISM: Yarrowia lipolytica

<400> SEQUENCE: 10
attcctgctg tcaacgtgac ctcttcgtcc accgttgtcg ccgttcttga gtctgcccga      60
gccaacaagt cccccgtcat catccagatg tcccagggtg gcgctgccta ctttgctggc     120
aagggtgtcg acaacaagga tcagaccgcc tccatccagg gagccattgc cgctgcccag     180
ttcatccgaa ccattgctcc cgtttacggc attcccgtca tcgtccacac cgaccactgt     240
gcccgaaagc tgctcccctg gctcgacggt atgctcgacg ccgatgagga gtacttcaag     300
actcacggtg agcccctctt ctcttcacac atggtggatc tctccgagga ggagcacccc     360
gagaacatcg ccaccaccgc cgagtacttc aagcgagccg ccaagatgaa ccagtggctc     420
gagatggaga tcggca                                                     436

<210> SEQ ID NO 11
<211> LENGTH: 145
<212> TYPE: PRT
<213> ORGANISM: Yarrowia lipolytica

<400> SEQUENCE: 11

Ile Pro Ala Val Asn Val Thr Ser Ser Thr Val Val Ala Val Leu
1               5                   10                  15

Glu Ser Ala Arg Ala Asn Lys Ser Pro Val Ile Ile Gln Met Ser Gln
                20                  25                  30

Gly Gly Ala Ala Tyr Phe Ala Gly Lys Gly Val Asp Asn Lys Asp Gln
            35                  40                  45

Thr Ala Ser Ile Gln Gly Ala Ile Ala Ala Gln Phe Ile Arg Thr
        50                  55                  60

Ile Ala Pro Val Tyr Gly Ile Pro Val Ile Val His Thr Asp His Cys
65                  70                  75                  80

Ala Arg Lys Leu Leu Pro Trp Leu Asp Gly Met Leu Asp Ala Asp Glu
                85                  90                  95

Glu Tyr Phe Lys Thr His Gly Glu Pro Leu Phe Ser Ser His Met Val
                100                 105                 110

Asp Leu Ser Glu Glu Glu His Pro Glu Asn Ile Ala Thr Thr Ala Glu
            115                 120                 125

Tyr Phe Lys Arg Ala Ala Lys Met Asn Gln Trp Leu Glu Met Glu Ile
        130                 135                 140

Gly
145

<210> SEQ ID NO 12
<211> LENGTH: 361
<212> TYPE: PRT
<213> ORGANISM: Kluyveromyces lactis (GenBank Accession No.CAC29023)

<400> SEQUENCE: 12

Met Pro Ala Gln Asp Val Leu Thr Arg Lys Thr Gly Val Ile Val Gly
1               5                   10                  15

Asp Asp Val Lys Ala Leu Phe Asp Tyr Ala Lys Glu His Lys Phe Ala
            20                  25                  30

Ile Pro Ala Ile Asn Val Thr Ser Ser Thr Val Ala Ala Leu
        35                  40                  45

Glu Ala Ala Arg Asp Asn Lys Ser Pro Ile Ile Leu Gln Thr Ser Asn
    50                  55                  60

Gly Gly Ala Ala Tyr Phe Ala Gly Lys Gly Val Ser Asn Glu Gly Gln
65                  70                  75                  80

Asn Ala Ser Ile Arg Gly Ser Ile Ala Ala His Tyr Ile Arg Ser
                85                  90                  95

Ile Ala Pro Ala Tyr Gly Ile Pro Val Val Leu His Thr Asp His Cys
            100                 105                 110

Ala Lys Lys Leu Leu Pro Trp Phe Asp Gly Met Leu Lys Ala Asp Glu
        115                 120                 125

Glu Tyr Phe Ala Lys His Gly Glu Pro Leu Phe Ser Ser His Met Leu
    130                 135                 140

Asp Leu Ser Glu Glu Thr Asp Glu Glu Asn Ile Gly Leu Cys Val Lys
145                 150                 155                 160

Tyr Phe Thr Arg Met Ala Lys Ile His Gln Trp Leu Glu Met Glu Ile
                165                 170                 175

Gly Ile Thr Gly Gly Glu Glu Asp Gly Val Asn Asn Glu Gly Thr Ser
            180                 185                 190

Asn Asp Lys Leu Tyr Thr Thr Pro Glu Thr Val Phe Ser Val His Glu
        195                 200                 205

Ala Leu Ser Lys Ile Ser Pro Asn Phe Ser Ile Ala Ser Ala Phe Gly
    210                 215                 220

Asn Val His Gly Val Tyr Lys Ile Ala Ala Leu Lys Pro Glu Leu
225                 230                 235                 240

Leu Gly Thr Phe Gln Asp Tyr Ala Ala Lys Gln Leu Asn Lys Lys Ala
                245                 250                 255

Glu Asp Lys Pro Leu Tyr Leu Val Phe His Gly Gly Ser Gly Ser Ser
            260                 265                 270

Thr Lys Asp Phe His Thr Ala Ile Asp Phe Gly Val Val Lys Val Asn
        275                 280                 285

Leu Asp Thr Asp Cys Gln Phe Ala Tyr Leu Ser Gly Ile Arg Asp Tyr
    290                 295                 300

Val Leu Asn Lys Lys Asp Tyr Leu Met Thr Pro Val Gly Asn Pro Thr
305                 310                 315                 320

Gly Glu Asp Ser Pro Asn Lys Lys Tyr Tyr Asp Pro Arg Val Trp Val
                325                 330                 335

Arg Glu Gly Glu Lys Thr Met Ser Lys Arg Ile Thr Gln Ala Leu Glu
            340                 345                 350

Ile Phe Arg Thr Lys Gly Ala Leu Glu
        355                 360

<210> SEQ ID NO 13
<211> LENGTH: 360
<212> TYPE: PRT
<213> ORGANISM: Paracoccidiodes brasiliensis (GenBank Accession No. AAL34519)

<400> SEQUENCE: 13

```
Met Gly Val Lys Asp Ile Leu Ser Arg Lys Thr Gly Val Ile Val Gly
1               5                   10                  15

Asp Val Leu Arg Leu Phe Gln His Ala Gln Glu Lys Val Phe Ala
                20                  25                  30

Ile Pro Ala Ile Asn Val Thr Ser Ser Thr Val Val Ala Ala Leu
            35                  40                  45

Glu Ala Ala Arg Asp Lys Asn Ser Pro Ile Ile Leu Gln Val Ser Gln
50                  55                  60

Gly Gly Ala Ala Phe Phe Ala Gly Lys Gly Val Pro Asn Gly Lys Gln
65                  70                  75                  80

Glu Ala Ser Val Ala Gly Ala Ile Ala Ala His Tyr Ile Arg Ser
                85                  90                  95

Ile Ala Pro Ser Tyr Gly Ile Pro Val Val Leu His Thr Asp His Cys
            100                 105                 110

Ala Lys Lys Leu Leu Pro Trp Leu Asp Gly Met Leu Asp Ala Asp Glu
        115                 120                 125

Cys Tyr Phe Lys Leu His Asn Glu Pro Leu Phe Ser Ser His Met Ile
130                 135                 140

Asp Leu Ser Glu Glu Ser Val Glu Trp Asn Ile Glu Thr Thr Ala Lys
145                 150                 155                 160

Tyr Leu Lys Arg Ala Ala Pro Met Lys Gln Trp Leu Glu Met Glu Ile
                165                 170                 175

Gly Ile Thr Gly Gly Glu Glu Asp Gly Val Asn Asn Glu Ser Val Asp
            180                 185                 190

Asn Asn Ser Leu Tyr Thr Gln Pro Glu Asp Ile Tyr Thr Ile Tyr Lys
        195                 200                 205

Thr Leu Ser Ala Ile Ser Pro Tyr Phe Ser Ile Ala Ala Gly Phe Gly
210                 215                 220

Asn Val His Gly Val Tyr Lys Pro Gly Asn Val Arg Leu His Pro Glu
225                 230                 235                 240

Leu Leu Ser Lys His Gln Ala His Val Lys Glu Lys Thr Gly Ser Ser
                245                 250                 255

Lys Asn Lys Pro Val Tyr Leu Val Phe His Gly Gly Ser Gly Ser Thr
            260                 265                 270

Lys Ala Glu Phe Lys Glu Ala Ile Ser Tyr Gly Val Val Lys Val Asn
        275                 280                 285

Leu Asp Thr Asp Leu Gln Tyr Ala Tyr Leu Ser Gly Val Arg Asp Phe
290                 295                 300

Val Leu Lys Lys Lys Asp Tyr Leu Met Ser Ala Val Gly Asn Pro Glu
305                 310                 315                 320

Gly Glu Asp Lys Pro Asn Lys Lys Tyr Phe Asp Pro Arg Val Trp Ile
                325                 330                 335

Arg Glu Gly Glu Lys Thr Met Cys Ala Arg Val Gln Glu Ala Phe Asp
            340                 345                 350

Asp Phe Asn Thr Ser Asn Gln Leu
        355                 360
```

<210> SEQ ID NO 14

```
<211> LENGTH: 24
<212> TYPE: DNA
<213> ORGANISM: Artificial Sequence
<220> FEATURE:
<223> OTHER INFORMATION: Primer YL217

<400> SEQUENCE: 14
cttgttggct cgggcagact caag                                            24

<210> SEQ ID NO 15
<211> LENGTH: 24
<212> TYPE: DNA
<213> ORGANISM: Artificial Sequence
<220> FEATURE:
<223> OTHER INFORMATION: Primer YL218

<400> SEQUENCE: 15
gcagcgccac cctgggacat ctgg                                            24

<210> SEQ ID NO 16
<211> LENGTH: 24
<212> TYPE: DNA
<213> ORGANISM: Artificial Sequence
<220> FEATURE:
<223> OTHER INFORMATION: Primer YL219

<400> SEQUENCE: 16
gatccttgtt gtcgacaccc ttgc                                            24

<210> SEQ ID NO 17
<211> LENGTH: 857
<212> TYPE: DNA
<213> ORGANISM: Yarrowia lipolytica

<400> SEQUENCE: 17
gggcctcaaa actacctcgg aactgctgcg ctgatctgga caccacagag gttccgagca     60
ctttaggttg caccaaatgt cccaccaggt gcaggcagaa aacgctggaa cagcgtgtac    120
agtttgtctt aacaaaaagt gagggcgctg aggtcgagca gggtggtgtg acttgttata    180
gcctttagag ctgcgaaagc gcgtatggat ttggctcatc aggccagatt gagggtctgt    240
ggacacatgt catgttagtg tacttcaatc gcccctgga tatagccccg acaataggcc     300
gtggcctcat ttttttgcct tccgcacatt tccattgctc ggtacccaca ccttgcttct    360
cctgcacttg ccaaccttaa tactggttta cattgaccaa catcttacaa gcgggggct     420 tgtctagggt atatataaac agtggctctc ccaatcggtt gccagtctct ttttccttt     480 ctttccccac agattcgaaa tctaaactac acatcacaca atgcctgtta ctgacgtcct    540
taagcgaaag tccggtgtca tcgtcggcga cgatgtccga gccgtgagta tccacgacaa    600
gatcagtgtc gagacgacgc gttttgtgta atgacacaat ccgaaagtcg ctagcaacac    660
acactctcta cacaaactaa cccagctctt cgagtacgcc cgagagcaca agttcgccct    720
ccccgccgtc aacgtgacct cttcgtccac cgttgtcgcc gttcttgagt ctgcccgagc    780
caacaagtcc cccgtcatca tccagatgtc ccagggtggc gctgcctact ttgctggcaa    840
gggtgtcgac aacaagg                                                   857

<210> SEQ ID NO 18
<211> LENGTH: 520
<212> TYPE: DNA
<213> ORGANISM: Yarrowia lipolytica

<400> SEQUENCE: 18
```

```
gggcctcaaa actacctcgg aactgctgcg ctgatctgga caccacagag gttccgagca      60
ctttaggttg caccaaatgt cccaccaggt gcaggcagaa aacgctggaa cagcgtgtac     120
agtttgtctt aacaaaaagt gagggcgctg aggtcgagca gggtggtgtg acttgttata     180
gcctttagag ctgcgaaagc gcgtatggat ttggctcatc aggccagatt gagggtctgt     240
ggacacatgt catgttagtg tacttcaatc gcccctgga tatagccccg acaataggcc      300
gtggcctcat ttttttgcct tccgcacatt tccattgctc ggtacccaca ccttgcttct     360
cctgcacttg ccaaccttaa tactggttta cattgaccaa catcttacaa gcggggggct     420
tgtctagggt atatataaac agtggctctc ccaatcggtt gccagtctct ttttttcctt      480
ctttccccac agattcgaaa tctaaactac acatcacaca                            520
```

<210> SEQ ID NO 19
<211> LENGTH: 1153
<212> TYPE: DNA
<213> ORGANISM: Yarrowia lipolytica

<400> SEQUENCE: 19

```
gggcctcaaa actacctcgg aactgctgcg ctgatctgga caccacagag gttccgagca      60
ctttaggttg caccaaatgt cccaccaggt gcaggcagaa aacgctggaa cagcgtgtac     120
agtttgtctt aacaaaaagt gagggcgctg aggtcgagca gggtggtgtg acttgttata     180
gcctttagag ctgcgaaagc gcgtatggat ttggctcatc aggccagatt gagggtctgt     240
ggacacatgt catgttagtg tacttcaatc gcccctgga tatagccccg acaataggcc      300
gtggcctcat ttttttgcct tccgcacatt tccattgctc ggtacccaca ccttgcttct     360
cctgcacttg ccaaccttaa tactggttta cattgaccaa catcttacaa gcggggggct     420
tgtctagggt atatataaac agtggctctc ccaatcggtt gccagtctct ttttttcctt      480
ctttccccac agattcgaaa tctaaactac acatcacaca atgcctgtta ctgacgtcct     540
taagcgaaag tccggtgtca tcgtcggcga cgatgtccga gccgtgagta tccacgacaa     600
gatcagtgtc gagacgacgc gttttgtgta atgcacaat ccgaaagtcg ctagcaacac      660
acactctcta cacaaactaa cccagctctt cgagtacgcc cgagagcaca agttcgccct     720
ccccgccgtc aacgtgacct cttcgtccac cgttgtcgcc gttcttgagt ctgcccgagc     780
caacaagtcc cccgtcatca tccagatgtc ccagggtggc gctgcctact tgctggcaa     840
gggtgtcgac aacaaggatc agaccgcctc catccaggga gccattgccg ctgcccagtt     900
catccgaacc attgctcccg tttacggcat tcccgtcatc gtccacaccg accactgtgc     960
ccgaaagctg ctcccctggc tcgacggtat gctcgacgcc gatgaggagt acttcaagac    1020
tcacggtgag cccctcttct cttcacacat ggtggatctc tccgaggagg agcaccccga    1080
gaacatcgcc accaccgccg agtacttcaa gcgagccgcc aagatgaacc agtggctcga    1140
gatggagatc ggc                                                       1153
```

<210> SEQ ID NO 20
<211> LENGTH: 531
<212> TYPE: DNA
<213> ORGANISM: Yarrowia lipolytica

<400> SEQUENCE: 20

```
atgcctgtta ctgacgtcct taagcgaaag tccggtgtca tcgtcggcga cgatgtccga      60
gccctcttcg agtacgcccg agagcacaag ttcgccctcc ccgccgtcaa cgtgacctct     120
```

-continued

```
tcgtccaccg ttgtcgccgt tcttgagtct gcccgagcca acaagtcccc cgtcatcatc    180
cagatgtccc agggtggcgc tgcctacttt gctggcaagg gtgtcgacaa caaggatcag    240
accgcctcca tccagggagc cattgccgct gcccagttca tccgaaccat tgctcccgtt    300
tacggcattc ccgtcatcgt ccacaccgac cactgtgccc gaaagctgct ccctggctc    360 gacggtatgc tcgacgccga tgaggagtac ttcaagactc acggtgagcc cctcttctct    420
tcacacatgg tggatctctc cgaggaggag caccccgaga catcgccac accgccgag     480 tacttcaagc gagccgccaa gatgaaccag tggctcgaga tggagatcgg c            531
```

<210> SEQ ID NO 21
<211> LENGTH: 177
<212> TYPE: PRT
<213> ORGANISM: Yarrowia lipolytica

<400> SEQUENCE: 21

```
Met Pro Val Thr Asp Val Leu Lys Arg Lys Ser Gly Val Ile Val Gly
1               5                   10                  15
Asp Asp Val Arg Ala Leu Phe Glu Tyr Ala Arg Glu His Lys Phe Ala
            20                  25                  30
Leu Pro Ala Val Asn Val Thr Ser Ser Ser Thr Val Val Ala Val Leu
        35                  40                  45
Glu Ser Ala Arg Ala Asn Lys Ser Pro Val Ile Ile Gln Met Ser Gln
    50                  55                  60
Gly Gly Ala Ala Tyr Phe Ala Gly Lys Gly Val Asp Asn Lys Asp Gln
65                  70                  75                  80
Thr Ala Ser Ile Gln Gly Ala Ile Ala Ala Gln Phe Ile Arg Thr
                85                  90                  95
Ile Ala Pro Val Tyr Gly Ile Pro Val Ile Val His Thr Asp His Cys
            100                 105                 110
Ala Arg Lys Leu Leu Pro Trp Leu Asp Gly Met Leu Asp Ala Asp Glu
        115                 120                 125
Glu Tyr Phe Lys Thr His Gly Glu Pro Leu Phe Ser Ser His Met Val
    130                 135                 140
Asp Leu Ser Glu Glu Glu His Pro Glu Asn Ile Ala Thr Thr Ala Glu
145                 150                 155                 160
Tyr Phe Lys Arg Ala Ala Lys Met Asn Gln Trp Leu Glu Met Glu Ile
                165                 170                 175
Gly
```

<210> SEQ ID NO 22
<211> LENGTH: 26
<212> TYPE: DNA
<213> ORGANISM: Artificial Sequence
<220> FEATURE:
<223> OTHER INFORMATION: Primer ODMW315

<400> SEQUENCE: 22

```
cacctggtgg gacatttggt gcaacc                                          26
```

<210> SEQ ID NO 23
<211> LENGTH: 26
<212> TYPE: DNA
<213> ORGANISM: Artificial Sequence
<220> FEATURE:
<223> OTHER INFORMATION: Primer ODMW316

<400> SEQUENCE: 23

-continued

```
gacaaactgt acacgctgtt ccagcg                                              26
```

<210> SEQ ID NO 24
<211> LENGTH: 24
<212> TYPE: DNA
<213> ORGANISM: Artificial Sequence
<220> FEATURE:
<223> OTHER INFORMATION: Primer ODMW317

<400> SEQUENCE: 24

```
cctgctcgac ctcagcgccc tcac                                                24
```

<210> SEQ ID NO 25
<211> LENGTH: 1152
<212> TYPE: DNA
<213> ORGANISM: Yarrowia lipolytica

<400> SEQUENCE: 25

```
agtcgaggac ttatcctagc ctcygaatac tttcaacaag ttacacccct attccccacc         60
aagccgctag atacgccact aagcaaagtt caagagccat cgcacaatta tctacgagta        120
ccgcagcaat cattcatttc aaggcacaca tggggtttct cttgcagaaa acgcacggt         180
ttcaaagtat aaacgcacat ctaggccgag acaagttgcg gggtatggta ctagtatttc        240
cgggtgcatt ccacgggtga atgggcgttt agaattgagg caattgccac gggttgggcc        300
acatatgttg agtactcatt tctcctctca atgaacgtct ccagaatgac atacattctc        360
ctccaacacc ttgtggggta aacttctgtc agattccacg taacaaggtt ggtgtcggaa        420
caacgaaaaa ggatcggaac agagcttccg gtgtcggtga ttgggcaggg ggctgaggcg        480
tgcctggcgc gtgcgcgtgg tagagagagt gtgctacagc agagagatat tactcgtttg        540
gagctagaga tgccgccgtt gaagaaatta acgaacgagt aactaacaga ccattccagg        600
atcatcgagg accgttgtca gcgcccttac tacagaaatg tatgtacagt aattacaact        660
gcgcggctgc ttgacggatg tatggagtct aagtaatgag tgcgtacgta gcaacaacag        720
tgtacgcagt actatagagg aacaattgcc ccggagaaga cggccaggcc gcctagatga        780
caaattcaac aactcacagc tgactttctg ccattgccac taggggggggg ccttttttata       840
tggccaagcc aagctctcca cgtcggttgg gctgcaccca acaataaatg ggtagggttg        900
caccaacaaa gggatgggat gggggggtaga agatacgagg ataacggggc tcaatggcac        960
aaataagaac gaatactgcc attaagactc gtgatccagc gactgacacc attgcatcat       1020
ctaagggcct caaaactacc tcggaactgc tgcgctgatc tggacaccac agaggttccg       1080
agcactttag gttgcaccaa atgtcccacc aggtgcaggc agaaaacgct ggaacagcgt       1140
gtacagtttg tc                                                          1152
```

<210> SEQ ID NO 26
<211> LENGTH: 2177
<212> TYPE: DNA
<213> ORGANISM: Yarrowia lipolytica

<400> SEQUENCE: 26

```
agtcgaggac ttatcctagc ctcygaatac tttcaacaag ttacacccct attccccacc         60
aagccgctag atacgccact aagcaaagtt caagagccat cgcacaatta tctacgagta        120
ccgcagcaat cattcatttc aaggcacaca tggggtttct cttgcagaaa acgcacggt         180
ttcaaagtat aaacgcacat ctaggccgag acaagttgcg gggtatggta ctagtatttc        240
cgggtgcatt ccacgggtga atgggcgttt agaattgagg caattgccac gggttgggcc        300
```

```
acatatgttg agtactcatt tctcctctca atgaacgtct ccagaatgac atacattctc     360
ctccaacacc ttgtggggta aacttctgtc agattccacg taacaaggtt ggtgtcggaa     420
caacgaaaaa ggatcggaac agagcttccg gtgtcggtga ttgggcaggg ggctgaggcg     480
tgcctggcgc gtgcgcgtgg tagagagagt gtgctacagc agagagatat tactcgtttg     540
gagctagaga tgccgccgtt gaagaaatta acgaacgagt aactaacaga ccattccagg     600
atcatcgagg accgttgtca gcgcccttac tacagaaatg tatgtacagt aattacaact     660
gcgcggctgc ttgacggatg tatggagtct aagtaatgag tgcgtacgta gcaacaacag     720
tgtacgcagt actatagagg aacaattgcc ccggagaaga cggccaggcc gcctagatga     780
caaattcaac aactcacagc tgactttctg ccattgccac tagggggggg ccttttata     840
tggccaagcc aagctctcca cgtcggttgg gctgcaccca acaataaatg ggtagggttg     900
caccaacaaa gggatgggat gggggtaga agatacgagg ataacggggc tcaatggcac     960
aaataagaac gaatactgcc attaagactc gtgatccagc gactgacacc attgcatcat    1020
ctaagggcct caaaactacc tcggaactgc tgcgctgatc tggacaccac agaggttccg    1080
agcactttag gttgcaccaa atgtcccacc aggtgcaggc agaaaacgct ggaacagcgt    1140
gtacagtttg tcttaacaaa aagtgagggc gctgaggtcg agcagggtgg tgtgacttgt    1200
tatagccttt agagctgcga aagcgcgtat ggatttggct catcaggcca gattgagggt    1260
ctgtggacac atgtcatgtt agtgtacttc aatcgccccc tggatatagc ccgacaata     1320
ggccgtggcc tcattttttt gccttccgca catttccatt gctcggtacc cacaccttgc    1380
ttctcctgca cttgccaacc ttaatactgg tttacattga ccaacatctt acaagcgggg    1440
ggcttgtcta gggtatatat aaacagtggc tctcccaatc ggttgccagt ctcttttttc    1500
ctttctttcc ccacagattc gaaatctaaa ctacacatca cacaatgcct gttactgacg    1560
tccttaagcg aaagtccggt gtcatcgtcg gcgacgatgt ccgagccgtg agtatccacg    1620
acaagatcag tgtcgagacg acgcgttttg tgtaatgaca caatccgaaa gtcgctagca    1680
acacacactc tctacacaaa ctaacccagc tcttcgagta cgcccgagag cacaagttcg    1740
ccctccccgc cgtcaacgtg acctcttcgt ccaccgttgt cgccgttctt gagtctgccc    1800
gagccaacaa gtccccgtc atcatccaga tgtcccaggg tggcgctgcc tactttgctg      1860
gcaagggtgt cgacaacaag gatcagaccg cctccatcca gggagccatt gccgctgccc    1920
agttcatccg aaccattgct cccgtttacg gcattcccgt catcgtccac accgaccact    1980
gtgcccgaaa gctgctcccc tggctcgacg gtatgctcga cgccgatgag gagtacttca    2040
agactcacgg tgagccctc ttctcttcac acatggtgga tctctccgag gaggagcacc      2100
ccgagaacat cgccaccacc gccgagtact tcaagcgagc cgccaagatg aaccagtggc    2160
tcgagatgga gatcggc                                                    2177
```

<210> SEQ ID NO 27
<211> LENGTH: 1542
<212> TYPE: DNA
<213> ORGANISM: Yarrowia lipolytica

<400> SEQUENCE: 27

```
tcgaggactt atcctagcct cygaatactt tcaacaagtt acacccttat tccccaccaa      60
gccgctagat acgccactaa gcaaagttca agagccatcg cacaattatc tacgagtacc    120
gcagcaatca ttcatttcaa ggcacacatg gggtttctct tgcagaaaaa cgcacggttt    180
```

-continued

```
caaagtataa acgcacatct aggccgagac aagttgcggg gtatggtact agtatttccg    240
ggtgcattcc acgggtgaat gggcgtttag aattgaggca attgccacgg gttgggccac    300
atatgttgag tactcatttc tcctctcaat gaacgtctcc agaatgacat acattctcct    360
ccaacacctt gtgggtaaa cttctgtcag attccacgta acaaggttgg tgtcggaaca     420
acgaaaaagg atcggaacag agcttccggt gtcggtgatt gggcagggg ctgaggcgtg     480
cctggcgcgt gcgcgtggta gagagagtgt gctacagcag agagatatta ctcgtttgga   540
gctagagatg ccgccgttga agaaattaac gaacgagtaa ctaacagacc attccaggat   600
catcgaggac cgttgtcagc gcccttacta cagaaatgta tgtacagtaa ttacaactgc   660
gcggctgctt gacggatgta tggagtctaa gtaatgagtg cgtacgtagc aacaacagtg   720
tacgcagtac tatagaggaa caattgcccc ggagaagacg gccaggccgc ctagatgaca   780
aattcaacaa ctcacagctg actttctgcc attgccacta gggggggggcc ttttatatg    840
gccaagccaa gctctccacg tcggttgggc tgcacccaac aataaatggg tagggttgca   900
ccaacaaagg gatgggatgg ggggtagaag atacgaggat aacggggctc aatggcacaa   960
ataagaacga atactgccat taagactcgt gatccagcga ctgacaccat tgcatcatct  1020
aagggcctca aaactacctc ggaactgctg cgctgatctg gacaccacag aggttccgag  1080
cactttaggt tgcaccaaat gtcccaccag gtgcaggcag aaaacgctgg aacagcgtgt  1140
acagtttgtc ttaacaaaaa gtgagggcgc tgaggtcgag cagggtggtg tgacttgtta  1200
tagcctttag agctgcgaaa gcgcgtatgg atttggctca tcaggccaga ttgagggtct  1260
gtggacacat gtcatgttag tgtacttcaa tcgcccctg gatatagccc cgacaatagg    1320
ccgtggcctc attttttgc cttccgcaca tttccattgc tcggtaccca caccttgctt   1380
ctcctgcact tgccaacctt aatactggtt tacattgacc aacatcttac aagcgggggg  1440
cttgtctagg gtatatataa acagtggctc tcccaatcgg ttgccagtct ctttttttcct 1500
ttctttcccc acagattcga aatctaaact acacatcaca ca                     1542
```

<210> SEQ ID NO 28
<211> LENGTH: 33
<212> TYPE: DNA
<213> ORGANISM: Artificial Sequence
<220> FEATURE:
<223> OTHER INFORMATION: Primer YL33

<400> SEQUENCE: 28

```
tttccatggt acgtcctgta gaaaccccaa ccc                                 33
```

<210> SEQ ID NO 29
<211> LENGTH: 36
<212> TYPE: DNA
<213> ORGANISM: Artificial Sequence
<220> FEATURE:
<223> OTHER INFORMATION: Primer YL34

<400> SEQUENCE: 29

```
cccttaatta atcattgttt gcctccctgc tgcggt                              36
```

<210> SEQ ID NO 30
<211> LENGTH: 436
<212> TYPE: DNA
<213> ORGANISM: Yarrowia lipolytica

<400> SEQUENCE: 30

```
gaccgggttg gcggcgtatt tgtgtcccaa aaaacagccc caattgcccc aattgacccc    60
```

```
aaattgaccc agtagcgggc ccaaccccgg cgagagcccc cttcacccca catatcaaac      120
ctcccccggt tcccacactt gccgttaagg gcgtagggta ctgcagtctg gaatctacgc      180
ttgttcagac tttgtactag tttctttgtc tggccatccg ggtaacccat gccggacgca      240
aaatagacta ctgaaaattt ttttgctttg tggttgggac tttagccaag ggtataaaag      300
accaccgtcc ccgaattacc tttcctcttc ttttctctct ctccttgtca actcacaccc      360
gaaatcgtta agcatttcct tctgagtata agaatcattc aaaggatcca ctagttctag      420
agcggccgct taaacc                                                     436

<210> SEQ ID NO 31
<211> LENGTH: 19
<212> TYPE: DNA
<213> ORGANISM: Artificial Sequence
<220> FEATURE:
<223> OTHER INFORMATION: Primer TEF5'

<400> SEQUENCE: 31
agagaccggg ttggcggcg                                                   19

<210> SEQ ID NO 32
<211> LENGTH: 30
<212> TYPE: DNA
<213> ORGANISM: Artificial Sequence
<220> FEATURE:
<223> OTHER INFORMATION: Primer TEF3'

<400> SEQUENCE: 32
ttggatcctt tgaatgattc ttatactcag                                       30

<210> SEQ ID NO 33
<211> LENGTH: 173
<212> TYPE: DNA
<213> ORGANISM: Yarrowia lipolytica

<400> SEQUENCE: 33
ccgcggcccg agattccggc ctcttcggcc gccaagcgac ccgggtggac gtctagaggt       60
acctagcaat taacagatag tttgccggtg ataattctct taacctccca cactcctttg      120
acataacgat ttatgtaacg aaactgaaat ttgaccagat attgtgtccg cgg             173

<210> SEQ ID NO 34
<211> LENGTH: 29
<212> TYPE: DNA
<213> ORGANISM: Artificial Sequence
<220> FEATURE:
<223> OTHER INFORMATION: Primer XPR5'

<400> SEQUENCE: 34
tttccgcggc ccgagattcc ggcctcttc                                        29

<210> SEQ ID NO 35
<211> LENGTH: 31
<212> TYPE: DNA
<213> ORGANISM: Artificial Sequence
<220> FEATURE:
<223> OTHER INFORMATION: Primer XPR3'

<400> SEQUENCE: 35
tttccgcgga cacaatatct ggtcaaattt c                                     31

<210> SEQ ID NO 36
```

```
<211> LENGTH: 31
<212> TYPE: DNA
<213> ORGANISM: Artificial Sequence
<220> FEATURE:
<223> OTHER INFORMATION: Primer YL1

<400> SEQUENCE: 36
cagtgccaaa agccaaggca ctgagctcgt c                               31

<210> SEQ ID NO 37
<211> LENGTH: 31
<212> TYPE: DNA
<213> ORGANISM: Artificial Sequence
<220> FEATURE:
<223> OTHER INFORMATION: Primer YL2

<400> SEQUENCE: 37
gacgagctca gtgccttggc ttttggcact g                               31

<210> SEQ ID NO 38
<211> LENGTH: 36
<212> TYPE: DNA
<213> ORGANISM: Artificial Sequence
<220> FEATURE:
<223> OTHER INFORMATION: Primer YL3

<400> SEQUENCE: 38
gtataagaat cattcaccat ggatccacta gttcta                          36

<210> SEQ ID NO 39
<211> LENGTH: 36
<212> TYPE: DNA
<213> ORGANISM: Artificial Sequence
<220> FEATURE:
<223> OTHER INFORMATION: Primer YL4

<400> SEQUENCE: 39
tagaactagt ggatccatgg tgaatgattc ttatac                          36

<210> SEQ ID NO 40
<211> LENGTH: 36
<212> TYPE: DNA
<213> ORGANISM: Artificial Sequence
<220> FEATURE:
<223> OTHER INFORMATION: Primer YL23

<400> SEQUENCE: 40
atggatccac tagttaatta actagagcgg ccgcca                          36

<210> SEQ ID NO 41
<211> LENGTH: 36
<212> TYPE: DNA
<213> ORGANISM: Artificial Sequence
<220> FEATURE:
<223> OTHER INFORMATION: Primer YL24

<400> SEQUENCE: 41
tggcggccgc tctagttaat taactagtgg atccat                          36

<210> SEQ ID NO 42
<211> LENGTH: 35
<212> TYPE: DNA
<213> ORGANISM: Artificial Sequence
<220> FEATURE:
<223> OTHER INFORMATION: Primer YL9

<400> SEQUENCE: 42
```

```
tggtaaataa atgatgtcga ctcaggcgac gacgg            35
```

<210> SEQ ID NO 43
<211> LENGTH: 35
<212> TYPE: DNA
<213> ORGANISM: Artificial Sequence
<220> FEATURE:
<223> OTHER INFORMATION: Primer YL10

<400> SEQUENCE: 43

```
ccgtcgtcgc ctgagtcgac atcatttatt tacca            35
```

<210> SEQ ID NO 44
<211> LENGTH: 33
<212> TYPE: DNA
<213> ORGANISM: Artificial Sequence
<220> FEATURE:
<223> OTHER INFORMATION: Primer ODMW314

<400> SEQUENCE: 44

```
cgtgccatgg tgtgatgtgt agtttagatt tcg              33
```

<210> SEQ ID NO 45
<211> LENGTH: 39
<212> TYPE: DNA
<213> ORGANISM: Artificial Sequence
<220> FEATURE:
<223> OTHER INFORMATION: Primer YL341

<400> SEQUENCE: 45

```
tttgtcgacg tttaaacagt gtacgcagta ctatagagg        39
```

<210> SEQ ID NO 46
<211> LENGTH: 995
<212> TYPE: DNA
<213> ORGANISM: Yarrowia lipolytica

<400> SEQUENCE: 46

```
agtgtacgca gtactataga ggaacaattg ccccggagaa gacggccagg ccgcctagat    60
gacaaattca caactcaca gctgactttc tgccattgcc actagggggg ggcctttta   120
tatggccaag ccaagctctc cacgtcggtt gggctgcacc caacaataaa tgggtaggggt  180
tgcaccaaca aagggatggg atgggggta aagatacga ggataacggg gctcaatggc    240
acaaataaga acgaatactg ccattaagac tcgtgatcca gcgactgaca ccattgcatc   300
atctaagggc ctcaaaacta cctcggaact gctgcgctga tctggacacc acagaggttc    360
cgagcacttt aggttgcacc aaatgtccca ccaggtgcag gcagaaaacg ctggaacagc    420
gtgtacagtt tgtcttaaca aaaagtgagg gcgctgaggt cgagcagggt ggtgtgactt     480
gttatagcct ttagagctgc gaaagcgcgt atggatttgg ctcatcaggc cagattgagg    540
gtctgtggac acatgtcatg ttagtgtact tcaatcgccc cctggatata gccccgacaa    600
taggccgtgg cctcattttt ttgccttccg cacatttcca ttgctcggta cccacacctt    660
gcttctcctg cacttgccaa ccttaatact ggtttacatt gaccaacatc ttacaagcgg    720
ggggcttgtc tagggtatat ataaacagtg gctctcccaa tcggttgcca gtctcttttt    780
tcctttcttt ccccacagat tcgaaatcta aactacacat cacacaatgc ctgttactga    840
cgtccttaag cgaaagtccg gtgtcatcgt cggcgacgat gtccgagccg tgagtatcca    900
cgacaagatc agtgtcgaga cgacgcgttt tgtgtaatga cacaatccga aagtcgctag    960
```

```
caacacacac tctctacaca aactaaccca gctct                                    995
```

<210> SEQ ID NO 47
<211> LENGTH: 34
<212> TYPE: DNA
<213> ORGANISM: Artificial Sequence
<220> FEATURE:
<223> OTHER INFORMATION: Primer ODMW320

<400> SEQUENCE: 47

```
cgtgccatgg agagctgggt tagtttgtgt agag                                     34
```

<210> SEQ ID NO 48
<211> LENGTH: 39
<212> TYPE: DNA
<213> ORGANISM: Artificial Sequence
<220> FEATURE:
<223> OTHER INFORMATION: Primer ODMW341

<400> SEQUENCE: 48

```
tttgtcgacg tttaaacagt gtacgcagta ctatagagg                                39
```

<210> SEQ ID NO 49
<211> LENGTH: 966
<212> TYPE: DNA
<213> ORGANISM: Yarrowia lipolytica

<400> SEQUENCE: 49

```
gcagtaggat gtcctgcacg ggtctttttg tggggtgtgg agaaagggt gcttggagat          60
ggaagccggt agaaccgggc tgcttgtgct tggagatgga agccggtaga accgggctgc        120
ttgggggat ttggggccgc tgggctccaa agaggggtag gcatttcgtt ggggttacgt         180
aattgcggca tttgggtcct cgcgcatgt cccattggtc agaattagtc cggataggag         240
acttatcagc caatcacagc gccggatcca cctgtaggtt gggttgggtg ggagcacccc        300
tccacagagt agagtcaaac agcagcagca acatgatagt tgggggtgtg cgtgttaaag        360
gaaaaaaaag aagcttgggt tatattcccg ctctatttag aggttgcggg atagacgccg        420
acggagggca atggcgccat ggaaccttgc ggatatcgat acgccgcggc ggactgcgtc        480
cgaaccagct ccagcagcgt ttttccggg ccattgagcc gactgcgacc ccgccaacgt        540
gtcttggccc acgcactcat gtcatgttgg tgttgggagg ccactttta agtagcacaa        600
ggcacctagc tcgcagcaag gtgtccgaac caaagaagcg gctgcagtgg tgcaaacggg        660
gcggaaacgg cgggaaaaag ccacggggc acgaattgag gcacgccctc gaatttgaga        720
cgagtcacgg ccccattcgc ccgcgcaatg gtcgccaac gcccggtctt ttgcaccaca        780
tcaggttacc ccaagccaaa cctttgtgtt aaaaagctta acatattata ccgaactag        840
gtttgggcgg gcttgctccg tctgtccaag gcaacattta tataagggtc tgcatcgccg        900
gctcaattga atctttttc ttcttctctt ctctatattc attcttgaat taaacacaca        960
tcaacc                                                                   966
```

<210> SEQ ID NO 50
<211> LENGTH: 30
<212> TYPE: DNA
<213> ORGANISM: Artificial Sequence
<220> FEATURE:
<223> OTHER INFORMATION: Primer YL211

<400> SEQUENCE: 50

```
tttgtcgacg cagtaggatg tcctgcacgg                                          30
```

<210> SEQ ID NO 51
<211> LENGTH: 34
<212> TYPE: DNA
<213> ORGANISM: Artificial Sequence
<220> FEATURE:
<223> OTHER INFORMATION: Primer YL212

<400> SEQUENCE: 51
tttccatggt tgatgtgtgt ttaattcaag aatg                          34

<210> SEQ ID NO 52
<211> LENGTH: 843
<212> TYPE: DNA
<213> ORGANISM: Yarrowia lipolytica

<400> SEQUENCE: 52
cattaattct cacgtgacac agattattaa cgtctcgtac caaccacaga ttacgaccca    60
ttcgcagtca cagttcacta gggtttgggt tgcatccgtt gagagcggtt tgtttttaac   120
cttctccatg tgctcactca ggttttgggt tcagatcaaa tcaaggcgtg aaccactttg   180
tttgaggaca aatgtgacac aaccaaccag tgtcagggc aagtccgtga caaaggggaa    240
gatacaatgc aattactgac agttacagac tgcctcgatg ccctaacctt gccccaaaat   300
aagacaactg tcctcgttta agcgcaaccc tattcagcgt cacgtcataa tagcgtttgg   360
atagcactag tctatgagga gcgttttatg ttgcggtgag ggcgattggt gctcatatgg   420
gttcaattga ggtggcggaa cgagcttagt cttcaattga ggtgcgagcg acacaattgg   480
gtgtcacgtg gcctaattga cctcgggtcg tggagtcccc agttatacag caaccacgag   540
gtgcatgggt aggagacgtc accagacaat agggtttttt ttggactgga gagggttggg   600
caaaagcgct caacgggctg tttggggagc tgtggggag gaattggcga tatttgtgag    660
gttaacggct ccgatttgcg tgttttgtcg ctcctgcatc tccccatacc catatcttcc   720
ctccccacct ctttccacga taattttacg gatcagcaat aaggttcctt ctcctagttt   780
ccacgtccat atatatctat gctgcgtcgt ccttttcgtg acatcaccaa aacacataca   840
acc                                                                843

<210> SEQ ID NO 53
<211> LENGTH: 33
<212> TYPE: DNA
<213> ORGANISM: Artificial Sequence
<220> FEATURE:
<223> OTHER INFORMATION: Primer YL203

<400> SEQUENCE: 53
tttccatggt tgtatgtgtt ttggtgatgt cac                           33

<210> SEQ ID NO 54
<211> LENGTH: 33
<212> TYPE: DNA
<213> ORGANISM: Artificial Sequence
<220> FEATURE:
<223> OTHER INFORMATION: Primer YL204

<400> SEQUENCE: 54
tttgtcgacc gtttaagcgc aaccctattc agc                           33

<210> SEQ ID NO 55
<211> LENGTH: 102
<212> TYPE: DNA

<213> ORGANISM: Yarrowia lipolytica

<400> SEQUENCE: 55
gtgagtatcc acgacaagat cagtgtcgag acgacgcgtt ttgtgtaatg acacaatccg    60
aaagtcgcta gcaacacaca ctctctacac aaactaaccc ag    102

<210> SEQ ID NO 56
<211> LENGTH: 10
<212> TYPE: DNA
<213> ORGANISM: Yarrowia lipolytica
<220> FEATURE:
<221> NAME/KEY: misc_feature
<222> LOCATION: (8)..(8)
<223> OTHER INFORMATION: n is a, c, g, or t

<400> SEQUENCE: 56 mammatgnhs    10

<210> SEQ ID NO 57
<211> LENGTH: 21
<212> TYPE: DNA
<213> ORGANISM: Artificial Sequence
<220> FEATURE:
<223> OTHER INFORMATION: Primer YL-URA-16F

<400> SEQUENCE: 57
gctcgagcta acgtccacaa g    21

<210> SEQ ID NO 58
<211> LENGTH: 18
<212> TYPE: DNA
<213> ORGANISM: Artificial Sequence
<220> FEATURE:
<223> OTHER INFORMATION: Primer YL-URA-78R

<400> SEQUENCE: 58
cttggctgcc acgagctt    18

<210> SEQ ID NO 59
<211> LENGTH: 22
<212> TYPE: DNA
<213> ORGANISM: Artificial Sequence
<220> FEATURE:
<223> OTHER INFORMATION: Primer GUS-767F

<400> SEQUENCE: 59
ccaaaagcca gacagagtgt ga    22

<210> SEQ ID NO 60
<211> LENGTH: 22
<212> TYPE: DNA
<213> ORGANISM: Artificial Sequence
<220> FEATURE:
<223> OTHER INFORMATION: Primer GUS-891R

<400> SEQUENCE: 60
ttcatgacga ccaaagccag ta    22

<210> SEQ ID NO 61
<211> LENGTH: 1020
<212> TYPE: DNA
<213> ORGANISM: Artificial Sequence
<220> FEATURE:
<223> OTHER INFORMATION: GPM::FBAIN chimeric Yarrowia lipolytica
      promoter

<400> SEQUENCE: 61

```
gtcgaccatt aattctcacg tgacacagat tattaacgtc tcgtaccaac cacagattac      60
gacccattcg cagtcacagt tcactagggt ttggggttgca tccgttgaga gcggtttgtt     120
tttaaccttc tccatgtgct cactcaggtt ttgggttcag atcaaatcaa ggcgtgaacc     180
actttgtttg aggacaaatg tgacacaacc aaccagtgtc aggggcaagt ccgtgacaaa     240
ggggaagata caatgcaatt actgacagtt acagactgcc tcgatgccct aaccttgccc     300
caaaataaga caactgtcct cgtttaagcg caaccctatt cagcgtcacg tcataatagc     360
gtttggatag cactagtcta tgaggagcgt tttatgttgc ggtgagggcg attggtgctc     420
atatgggttc aattgaggtg gcggaacgag cttagtcttc aattgaggtg cgagcgacac     480
aattgggtgt cacgtggcct aattgacctc gggtcgtgga gtccccagtt atacagcaac     540
cacgaggtgc atgggtagga gacgtcacca gacaataggg ttttttttgg actggagagg     600
gttgggcaaa agcgctcaac gggctgtttg gggagctgtg ggggaggaat tggcgatatt     660
tgtgaggtta acggctccga tttgcgtgtt ttgtcgctcc tgcatctccc catacccata     720
tcttccctcc ccacctcttt ccacgataat tttacggatc agcaataagg ttccttctcc     780
tagtttccac gtccatatat atctatgctg cgtcgtcctt ttcgtgacat caccaaaaca     840
catacaacca tggctgttac tgacgtcctt aagcgaaagt ccggtgtcat cgtcggcgac     900
gatgtccgag ccgtgagtat ccacgacaag atcagtgtcg agacgacgcg ttttgtgtaa     960
tgacacaatc cgaaagtcgc tagcaacaca cactctctac acaaactaac ccagctctcc    1020
```

<210> SEQ ID NO 62
<211> LENGTH: 8953
<212> TYPE: DNA
<213> ORGANISM: Artificial Sequence
<220> FEATURE:
<223> OTHER INFORMATION: Plasmid pY5-30

<400> SEQUENCE: 62

```
ggtggagctc cagcttttgt tccctttagt gagggttaat ttcgagcttg gcgtaatcat      60
ggtcatagct gtttcctgtg tgaaattgtt atccgctcac aattccacac aacatacgag     120
ccggaagcat aaagtgtaaa gcctggggtg cctaatgagt gagctaactc acattaattg     180
cgttgcgctc actgcccgct ttccagtcgg gaaacctgtc gtgccagctg cattaatgaa     240
tcggccaacg cgcggggaga ggcggttttgc gtattgggcg ctcttccgct tcctcgctca     300
ctgactcgct gcgctcggtc gttcggctgc ggcgagcggt atcagctcac tcaaaggcgg     360
taatacggtt atccacagaa tcaggggata acgcaggaaa gaacatgtga gcaaaaggcc     420
agcaaaaggc caggaaccgt aaaaaggccg cgttgctggc gtttttccat aggctccgcc     480
cccctgacga gcatcacaaa aatcgacgct caagtcagag gtggcgaaac ccgacaggac     540
tataaagata ccaggcgttt ccccctggaa gctccctcgt gcgctctcct gttccgaccc     600
tgccgcttac cggatacctg tccgcctttc tcccttcggg aagcgtggcg ctttctcata     660
gctcacgctg taggtatctc agttcggtgt aggtcgttcg ctccaagctg ggctgtgtgc     720
acgaaccccc cgttcagccc gaccgctgcg ccttatccgg taactatcgt cttgagtcca     780
acccggtaag acacgactta tcgccactgg cagcagccac tggtaacagg attagcagag     840
cgaggtatgt aggcggtgct acagagttct tgaagtggtg gcctaactac ggctacacta     900
gaaggacagt atttggtatc tgcgctctgc tgaagccagt taccttcgga aaaagagttg     960
gtagctcttg atccggcaaa caaaccaccg ctggtagcgg tggtttttttt gtttgcaagc    1020
```

```
agcagattac gcgcagaaaa aaaggatctc aagaagatcc tttgatcttt tctacggggt    1080
ctgacgctca gtggaacgaa aactcacgtt aagggatttt ggtcatgaga ttatcaaaaa    1140
ggatcttcac ctagatcctt ttaaattaaa aatgaagttt aaatcaatc taaagtatat     1200 atgagtaaac ttggtctgac agttaccaat gcttaatcag tgaggcacct atctcagcga    1260
tctgtctatt tcgttcatcc atagttgcct gactccccgt cgtgtagata actacgatac    1320
gggagggctt accatctggc cccagtgctg caatgatacc gcgagaccca cgctcaccgg    1380
ctccagattt atcagcaata aaccagccag ccggaagggc cgagcgcaga gtggtcctg     1440 caactttatc cgcctccatc cagtctatta attgttgccg ggaagctaga gtaagtagtt    1500
cgccagttaa tagtttgcgc aacgttgttg ccattgctac aggcatcgtg gtgtcacgct    1560
cgtcgtttgg tatggcttca ttcagctccg gttcccaacg atcaaggcga gttacatgat    1620
cccccatgtt gtgcaaaaaa gcggttagct ccttcggtcc tccgatcgtt gtcagaagta    1680
agttggccgc agtgttatca ctcatggtta tggcagcact gcataattct cttactgtca    1740
tgccatccgt aagatgcttt tctgtgactg gtgagtactc aaccaagtca ttctgagaat    1800
agtgtatgcg gcgaccgagt tgctcttgcc cggcgtcaat acgggataat accgcgccac    1860
atagcagaac tttaaaagtg ctcatcattg gaaaacgttc ttcggggcga aaactctcaa    1920
ggatcttacc gctgttgaga tccagttcga tgtaacccac tcgtgcaccc aactgatctt    1980
cagcatcttt tactttcacc agcgtttctg ggtgagcaaa aacaggaagg caaaatgccg    2040
caaaaaaggg aataagggcg acacggaaat gttgaatact catactcttc cttttttcaat   2100 attattgaag catttatcag ggttattgtc tcatgagcgg atacatattt gaatgtattt     2160
agaaaaataa acaaataggg gttccgcgca catttcccccg aaaagtgcca cctgacgcgc    2220
cctgtagcgg cgcattaagc gcggcgggtg tggtggttac gcgcagcgtg accgctacac    2280
ttgccagcgc cctagcgccc gctcctttcg ctttcttccc ttcctttctc gccacgttcg    2340
ccggctttcc ccgtcaagct ctaaatcggg ggctcccttt agggttccga tttagtgctt    2400
tacggcacct cgaccccaaa aaacttgatt agggtgatgg ttcacgtagt gggccatcgc    2460
cctgatagac ggttttttcgc cctttgacgt tggagtccac gttctttaat agtggactct    2520
tgttccaaac tggaacaaca ctcaacccta tctcggtcta ttcttttgat ttataaggga    2580
ttttgccgat ttcggcctat tggttaaaaa atgagctgat ttaacaaaaa tttaacgcga    2640
attttaacaa aatattaacg cttacaattt ccattcgcca ttcaggctgc gcaactgttg    2700
ggaagggcga tcggtgcggg cctcttcgct attacgccag ctggcgaaag ggggatgtgc    2760
tgcaaggcga ttaagttggg taacgccagg gttttcccag tcacgacgtt gtaaaacgac    2820
ggccagtgaa ttgtaatacg actcactata gggcgaattg ggtaccgggc cccccctcga    2880
ggtcgatggt gtcgataagc ttgatatcga attcatgtca cacaaaccga tcttcgcctc    2940
aaggaaacct aattctacat ccgagagact gccgagatcc agtctacact gattaatttt    3000
cgggccaata atttaaaaaa atcgtgttat ataatattat atgtattata tatatacatc    3060
atgatgatac tgacagtcat gtcccattgc taaatagaca gactccatct gccgcctcca    3120
actgatgttc tcaatattta aggggtcatc tcgcattgtt taataataaa cagactccat    3180
ctaccgcctc caaatgatgt tctcaaaata tattgtatga acttattttt attacttagt    3240
attattagac aacttacttg ctttatgaaa aacacttcct atttaggaaa caatttataa    3300
tggcagttcg ttcatttaac aatttatgta gaataaatgt tataaatgcg tatgggaaat    3360
```

```
cttaaatatg gatagcataa aatgatatctg cattgcctaa ttcgaaatca acagcaacga    3420
aaaaaatccc ttgtacaaca taaatagtca tcgagaaata tcaactatca aagaacagct    3480
attcacacgt tactattgag attattattg gacgagaatc acacactcaa ctgtctttct    3540
ctcttctaga aatacaggta caagtatgta ctattctcat tgttcatact tctagtcatt    3600
tcatcccaca tattccttgg atttctctcc aatgaatgac attctatctt gcaaattcaa    3660
caattataat aagatatacc aaagtagcgg tatagtggca atcaaaaagc ttctctggtg    3720
tgcttctcgt atttatttt attctaatga tccattaaag gtatatattt atttcttgtt    3780
atataatcct tttgtttatt acatgggctg gatacataaa ggtattttga tttaatttt    3840 tgcttaaatt caatcccccc tcgttcagtg tcaactgtaa tggtaggaaa ttaccatact    3900
tttgaagaag caaaaaaat gaaagaaaaa aaaaatcgta tttccaggtt agacgttccg    3960
cagaatctag aatgcggtat gcggtacatt gttcttcgaa cgtaaaagtt gcgctccctg    4020
agatattgta cattttgct tttacaagta caagtacatc gtacaactat gtactactgt    4080
tgatgcatcc acaacagttt gttttgtttt ttttgtttt ttttttttct aatgattcat    4140
taccgctatg tatacctact tgtacttgta gtaagccggg ttattggcgt tcaattaatc    4200
atagacttat gaatctgcac ggtgtgcgct gcgagttact tttagcttat gcatgctact    4260
tgggtgtaat attgggatct gttcggaaat caacggatgc tcaaccgatt tcgacagtaa    4320
taatttgaat cgaatcggag cctaaaatga acccgagtat atctcataaa attctcggtg    4380
agaggtctgt gactgtcagt acaaggtgcc ttcattatgc cctcaacctt accatacctc    4440
actgaatgta gtgtacctct aaaaatgaaa tacagtgcca aaagccaagg cactgagctc    4500
gtctaacgga cttgatatac aaccaattaa aacaaatgaa aagaaataca gttctttgta    4560
tcatttgtaa caattaccct gtacaaacta aggtattgaa atcccacaat attcccaaag    4620
tccacccctt tccaaattgt catgcctaca actcatatac caagcactaa cctaccaaac    4680
accactaaaa ccccacaaaa tatatcttac cgaatataca gtaacaagct accaccacac    4740
tcgttgggtg cagtcgccag cttaaagata tctatccaca tcagccacaa ctcccttcct    4800
ttaataaacc gactacaccc ttggctattg aggttatgag tgaatatact gtagacaaga    4860
cactttcaag aagactgttt ccaaaacgta ccactgtcct ccactacaaa cacacccaat    4920
ctgcttcttc tagtcaaggt tgctacaccg gtaaattata aatcatcatt tcattagcag    4980
ggcagggccc tttttataga gtcttataca ctagcggacc ctgccggtag accaacccgc    5040
aggcgcgtca gtttgctcct tccatcaatg cgtcgtagaa acgacttact ccttcttgag    5100
cagctccttg accttgttgg caacaagtct ccgacctcgg aggtggagga agagcctccg    5160
atatcggcgg tagtgatacc agcctcgacg gactccttga cggcagcctc aacagcgtca    5220
ccggcgggct tcatgttaag agagaacttg agcatcatgg cggcagacag aatggtggca    5280
atggggttga ccttctgctt gccgagatcg ggggcagatc cgtgacaggg ctcgtacaga    5340
ccgaacgcct cgttggtgtc gggcagagaa gccagagagg cggagggcag cagacccaga    5400
gaaccgggga tgacggaggc ctcgtcggag atgatatcgc caaacatgtt ggtggtgatg    5460
atgataccat tcatcttgga gggctgcttg atgaggatca tggcggccga gtcgatcagc    5520
tggtggttga gctcgagctg ggggaattcg tccttgagga ctcgagtgac agtctttcgc    5580
caaagtcgag aggaggccag cacgttggcc ttgtcaagag accacacggg aagaggggg    5640 ttgtgctgaa gggccaggaa ggcggccatt cgggcaattc gctcaacctc aggaacggag    5700
taggtctcgg tgtcggaagc gacgccagat ccgtcatcct cctttcgctc tccaaagtag    5760
```

```
atacctccga cgagctctcg gacaatgatg aagtcggtgc cctcaacgtt tcggatgggg     5820
gagagatcgg cgagcttggg cgacagcagc tggcagggtc gcaggttggc gtacaggttc     5880
aggtcctttc gcagcttgag gagaccctgc tcgggtcgca cgtcggttcg tccgtcggga     5940
gtggtccata cggtgttggc agcgcctccg acagcaccga gcataataga gtcagccttt     6000
cggcagatgt cgagagtagc gtcggtgatg ggctcgccct ccttctcaat ggcagctcct     6060
ccaatgagtc ggtcctcaaa cacaaactcg gtgccggagg cctcagcaac agacttgagc     6120
accttgacgg cctcggcaat cacctcgggg ccacagaagt cgccgccgag aagaacaatc     6180
ttcttggagt cagtcttggt cttcttagtt tcgggttcca ttgtggatgt gtgtggttgt     6240
atgtgtgatg tggtgtgtgg agtgaaaatc tgtggctggc aaacgctctt gtatatatac     6300
gcacttttgc ccgtgctatg tggaagacta aacctccgaa gattgtgact caggtagtgc     6360
ggtatcggct agggacccaa accttgtcga tgccgatagc gctatcgaac gtaccccagc     6420
cggccgggag tatgtcggag gggacatacg agatcgtcaa gggtttgtgg ccaactggta     6480
aataaatgat gtcgactcag gcgacgacgg aattcctgca gcccatctgc agaattcagg     6540
agagaccggg ttggcggcgt atttgtgtcc caaaaaacag ccccaattgc cccaattgac     6600
cccaaattga cccagtagcg ggcccaaccc cggcgagagc cccettcacc ccacatatca     6660 aacctccccc ggttcccaca cttgccgtta agggcgtagg gtactgcagt ctggaatcta     6720
cgcttgttca gactttgtac tagtttcttt gtctggccat ccgggtaacc catgccggac     6780
gcaaaataga ctactgaaaa tttttttgct ttgtggttgg gactttagcc aagggtataa     6840
aagaccaccg tccccgaatt accttttcctc ttcttttctc tctctccttg tcaactcaca     6900
cccgaaatcg ttaagcattt ccttctgagt ataagaatca ttcaccatgg atggtacgtc     6960
ctgtagaaac cccaacccgt gaaatcaaaa aactcgacgg cctgtgggca ttcagtctgg     7020
atcgcgaaaa ctgtggaatt gatcagcgtt ggtgggaaag cgcgttacaa gaaagccggg     7080
caattgctgt gccaggcagt tttaacgatc agttcgccga tgcagatatt cgtaattatg     7140
cgggcaacgt ctggtatcag cgcgaagtct ttataccgaa aggttgggca ggccagcgta     7200
tcgtgctgcg tttcgatgcg gtcactcatt acggcaaagt gtgggtcaat aatcaggaag     7260
tgatggagca tcaggcggc tatacgccat ttgaagccga tgtcacgccg tatgttattg     7320
ccgggaaaag tgtacgtatc accgtttgtg tgaacaacga actgaactgg cagactatcc     7380
cgccgggaat ggtgattacc gacgaaaacg gcaagaaaaa gcagtcttac ttccatgatt     7440
tctttaacta tgccgggatc catcgcagcg taatgctcta caccacgccg aacacctggg     7500
tggacgatat caccgtggtg acgcatgtcg cgcaagactg taaccacgcg tctgttgact     7560
ggcaggtggt ggccaatggt gatgtcagcg ttgaactgcg tgatgcggat caacaggtgg     7620
ttgcaactgg acaaggcact agcgggactt gcaagtggt gaatccgcac ctctggcaac     7680
cgggtgaagg ttatctctat gaactgtgcg tcacagccaa agccagaca gagtgtgata     7740 tctacccgct tcgcgtcggc atccggtcag tggcagtgaa gggcgaacag ttcctgatta     7800
accacaaacc gttctacttt actggctttg gtcgtcatga agatgcggac ttacgtggca     7860
aaggattcga taacgtgctg atggtgcacg accacgcatt aatggactgg attgggccaa     7920
actcctaccg tacctcgcat taccttacg ctgaagagat gctcgactgg gcagatgaac     7980
atggcatcgt ggtgattgat gaaactgctg ctgtcggctt taacctctct ttaggcattg     8040
gtttcgaagc gggcaacaag ccgaaagaac tgtacagcga agaggcagtc aacggggaaa     8100
```

-continued

```
ctcagcaagc gcacttacag gcgattaaag agctgatagc gcgtgacaaa aaccacccaa    8160
gcgtggtgat gtggagtatt gccaacgaac cggatacccg tccgcaagtg cacgggaata    8220
tttcgccact ggcggaagca acgcgtaaac tcgacccgac gcgtccgatc acctgcgtca    8280
atgtaatgtt ctgcgacgct cacaccgata ccatcagcga tctctttgat gtgctgtgcc    8340
tgaaccgtta ttacgatgg tatgtccaaa gcggcgattt ggaaacggca gagaaggtac     8400 tggaaaaga acttctggcc tggcaggaga aactgcatca gccgattatc atcaccgaat     8460
acggcgtgga tacgttagcc gggctgcact caatgtacac cgacatgtgg agtgaagagt    8520
atcagtgtgc atggctggat atgtatcacc gcgtctttga tcgcgtcagc gccgtcgtcg    8580
gtgaacaggt atggaatttc gccgattttg cgacctcgca aggcatattg cgcgttggcg    8640
gtaacaagaa agggatcttc actcgcgacc gcaaaccgaa gtcggcggct ttctgctgc     8700 aaaaacgctg gactggcatg aacttcggtg aaaaaccgca gcaggaggc aaacaatgat     8760 taattaacta gagcggccgc caccgcgcc cgagattccg gcctcttcgg ccgccaagcg    8820
acccgggtgg acgtctagag gtacctagca attaacagat agtttgccgg tgataattct    8880 cttaaccctcc cacactcctt tgacataacg atttatgtaa cgaaactgaa atttgaccag    8940
atattgtgtc cgc                                                        8953

<210> SEQ ID NO 63
<211> LENGTH: 12649
<212> TYPE: DNA
<213> ORGANISM: Artificial Sequence
<220> FEATURE:
<223> OTHER INFORMATION: Plasmid pKUNF12T6E
<220> FEATURE:
<221> NAME/KEY: misc_feature
<222> LOCATION: (2507)..(2507)
<223> OTHER INFORMATION: n is a, c, g, or t
<220> FEATURE:
<221> NAME/KEY: misc_feature
<222> LOCATION: (2512)..(2515)
<223> OTHER INFORMATION: n is a, c, g, or t

<400> SEQUENCE: 63
taaccctcac taaagggaac aaaagctgga gctccaccgc ggacacaata tctggtcaaa      60
tttcagtttc gttacataaa tcgttatgtc aaaggagtgt gggaggttaa gagaattatc     120
accggcaaac tatctgttaa ttgctaggta cctctagacg tccacccggg tcgcttggcg    180
gccgaagagg ccggaatctc gggccgcggt ggcggccgct tagttggtct tggacttctt    240
gggcttcttc agtaggact ggacaaagaa gttgccgaac agagcgagca gggtgatcat     300
gtacacgccg agcagctgga ccagagcctg agggtagtcg caggggaaga ggtagtcgta    360
cagggactgc accagcatag ccatgaactg ggtcatctgc agagtggtga tgtagggctt    420
gatgggcttg acgaagccga agccctgaga ggaaaagaag tagtaggcgt acatgacggt    480
gtggacgaag gagttgagga tgacggagaa gtaggcgtcg ccaccaggag cgtacttggc    540
aatagcccac cagatggcga agatggtggc atggtggtac acgtgcagga aggagacctg    600
gttgaacttc ttgcacagga tcatgatagc ggtgtccagg aactcgtagg ccttggagac    660
gtagaacacg tagacgattc gggacatgcc ctgagcgtgg gactcgttgc ccttctccat    720
gtcgttgccg aagaccttgt agccaccag gatagcctgt cggatggtct cgacgcacat    780
gtagagggac agtccgaaga ggaacaggtt gtggagcagc ttgatggtct tcagctcgaa    840 ggcttctcc atctgcttca tgatgggaat gccgaagagc agcatggcca gtagccgac     900 ctcgaaggcg agcatggtgg agacgtccat catgggcaga ccgtcggtca gagcgtaggg    960
```

```
cttagctccg tccatccact ggtcgacacc ggtctcgact cgtccgacca cgtcgtccca    1020
gacagaggag ttggccatgg tgaatgattc ttatactcag aaggaaatgc ttaacgattt    1080
cgggtgtgag ttgacaagga gagagagaaa agaagaggaa aggtaattcg gggacggtgg    1140
tcttttatac ccttggctaa agtcccaacc acaaagcaaa aaaattttca gtagtctatt    1200
ttgcgtccgg catgggttac ccggatggcc agacaaagaa actagtacaa agtctgaaca    1260
agcgtagatt ccagactgca gtaccctacg cccttaacgg caagtgtggg aaccggggga    1320
ggtttgatat gtggggtgaa gggggctctc gccggggttg ggcccgctac tgggtcaatt    1380
tggggtcaat tggggcaatt ggggctgttt tttgggacac aaatacgccg ccaacccggt    1440
ctctcctgaa ttctgcatcg atcgaggaag aggacaagcg gctgcttctt aagtttgtga    1500
catcagtatc caaggcacca ttgcaaggat tcaaggcttt gaacccgtca tttgccattc    1560
gtaacgctgg tagacaggtt gatcggttcc ctacggcctc cacctgtgtc aatcttctca    1620
agctgcctga ctatcaggac attgatcaac ttcggaagaa acttttgtat gccattcgat    1680
cacatgctgg tttcgatttg tcttagagga acgcatatac agtaatcata gagaataaac    1740
gatattcatt tattaaagta gatagttgag gtagaagttg taaagagtga taaatagcgg    1800
ccgcgcctac ttaagcaacg ggcttgataa cagcggggg ggtgcccacg ttgttgcggt    1860
tgcggaagaa cagaacaccc ttaccagcac cctcggcacc agcgctgggc tcaacccact    1920
ggcacatacg cgcactgcgg tacatggcgc ggatgaagcc acgaggacca tcctggacat    1980
cagcccggta gtgcttgccc atgatgggct taatggcctc ggtggcctcg tccgcgttgt    2040
agaaggggat gctgctgacg tagtggtgga ggacatgagt ctcgatgatg ccgtggagaa    2100
ggtggcggcc gatgaagccc atctcacggt caatggtagc agcggcacca cggacgaagt    2160
tccactcgtc gttggtgtag tggggaaggg tagggtcggt gtgctggagg aaggtgatgg    2220
caacgagcca gtggttaacc cagaggtagg gaacaaagta ccagatggcc atgttgtaga    2280
aaccgaactt ctgaacgagg aagtacagag cagtggccat cagaccgata ccaatatcgc    2340
tgaggacgat gagcttagcg tcactgttct cgtacagagg gctgcgggga tcgaagtggt    2400
taacaccacc gccgaggccg ttatgcttgc ccttgccgcg accctcacgc tggcgctcgt    2460
ggtagttgtg gccggtaaca ttggtgatga ggtagttggg ccagccacg annnnctcag    2520 taagatgagc gagctcgtgg gtcatctttc cgagacgagt agcctgctgc tcgcgggttc    2580
ggggaacgaa gaccatgtca cgctccatgt tgccagtggc cttgtggtgc tttcggtggg    2640
agatttgcca gctgaagtag gggacaagga gggaagagtg aagaacccag ccagtaatgt    2700
cgttgatgat gcgagaatcg gagaaagcac cgtgaccgca ctcatgggca ataacccaga    2760
gaccagtacc gaaaagaccc tgaagaacgg tgtacacggc ccacagacca gcgcgggcgg    2820
gggtggaggg gatatattcg ggggtcacaa agttgtacca gatgctgaaa gtggtagtca    2880
ggaggacaat gtcgcggagg atataaccgt atcccttgag agcggagcgc ttgaagcagt    2940
gcttagggat ggcattgtag atgtccttga tggtaaagtc gggaacctcg aactggttgc    3000
cgtaggtgtc gagcatgaca ccatactcgg acttgggctt ggcgatatca acctcggaca    3060
tggacgagag cgatgtggaa gaggccgagt ggcggggaga gtctgaagga gagacggcgg    3120
cagactcaga atccgtcaca gtagttgagg tgacggtgcg tctaagcgca gggttctgct    3180
tgggcagagc cgaagtggac gccatggaga gctgggttag tttgtgtaga gagtgtgtgt    3240
tgctagcgac tttcggattg tgtcattaca caaaacgcgt cgtctcgaca ctgatcttgt    3300
```

```
cgtggatact cacggctcgg acatcgtcgc cgacgatgac accggacttt cgcttaagga   3360
cgtcagtaac aggcattgtg tgatgtgtag tttagatttc gaatctgtgg ggaaagaaag   3420 gaaaaagag actggcaacc gattgggaga gccactgttt atatataccc tagacaagcc    3480
ccccgcttgt aagatgttgg tcaatgtaaa ccagtattaa ggttggcaag tgcaggagaa   3540
gcaaggtgtg ggtaccgagc aatggaaatg tgcggaaggc aaaaaaatga ggccacggcc   3600
tattgtcggg gctatatcca gggggcgatt gaagtacact aacatgacat gtgtccacag   3660
accctcaatc tggcctgatg agccaaatcc atacgcgctt cgcagctct aaaggctata    3720 acaagtcaca ccaccctgct cgacctcagc gccctcactt tttgttaaga caaactgtac   3780
acgctgttcc agcgttttct gcctgcacct ggtgggacat ttggtgcaac ctaaagtgct   3840
cggaacctct gtggtgtcca gatcagcgca gcagttccga ggtagttttg aggcccttag   3900
atgatgcaat ggtgtcagtc gctggatcac gagtcttaat ggcagtattc gttcttatt    3960 gtgccattga gccccgttat cctcgtatct tctacccccc atcccatccc tttgttggtg   4020
caaccctacc catttattgt tgggtgcagc ccaaccgacg tggagagctt ggcttggcca   4080
tataaaaagg ccccccccta gtggcaatgg cagaaagtca gctgtgagtt gttgaatttg   4140
tcatctaggc ggcctggccg tcttctccgg ggcaattgtt cctctatagt actgcgtaca   4200
ctgtttaaac agtgtacgca gatctgcgac gacggaattc ctgcagccca tctgcagaat   4260
tcaggagaga ccgggttggc ggcgtatttg tgtcccaaaa acagcccca attgccccaa     4320 ttgaccccaa attgacccag tagcgggccc aaccccggcg agagccccct tcaccccaca   4380
tatcaaacct ccccggttc ccacacttgc cgttaagggc gtagggtact gcagtctgga    4440
atctacgctt gttcagactt tgtactagtt tctttgtctg gccatccggg taacccatgc   4500
cggacgcaaa atagactact gaaaattttt ttgctttgtg gttgggactt tagccaaggg   4560
tataaaagac caccgtcccc gaattacctt cctcttcttt ttctctctct ccttgtcaac   4620
tcacacccga aatcgttaag catttccttc tgagtataag aatcattcac catggctgcc   4680
gctccctctg tgcgaacctt tacccgagcc gaggttctga acgctgaggc tctgaacgag   4740
ggcaagaagg acgctgaggc tcccttcctg atgatcatcg acaacaaggt gtacgacgtc   4800
cgagagttcg tccctgacca tcctggaggc tccgtgattc tcacccacgt tggcaaggac   4860
ggcaccgacg tctttgacac cttctcatccc gaggctgctt gggagactct cgccaacttc   4920
tacgttggag acattgacga gtccgaccga gacatcaaga acgatgactt tgccgctgag   4980
gtccgaaagc tgcgaaccct gttccagtct ctcggctact acgactcctc taaggcctac   5040
tacgccttca aggtctcctt caacctctgc atctggggac tgtccaccgt cattgtggcc   5100
aagtggggtc agacctccac cctcgccaac gtgctctctg ctgccctgct cggcctgttc   5160 tgcagcagt gcggatggct ggctcacgac tttctgcacc accaggtctt ccaggaccga   5220
ttctggggtg atctcttcgg agccttcctg ggaggtgtct gccagggctt ctcctcttcc   5280
tggtggaagg acaagcacaa cactcaccat gccgctccca acgtgcatgg cgaggatcct   5340
gacattgaca cccaccctct cctgacctgg tccgagcacg ctctggagat gttctccgac   5400
gtccccgatg aggagctgac ccgaatgtgg tctcgattca tggtcctgaa ccagacctgg   5460
ttctacttcc ccattctctc cttcgctcga ctgtcttggt gcctccagtc cattctcttt   5520
gtgctgccca acggtcaggc tcacaagccc tccggagctc gagtgcccat ctccctggtc   5580
gagcagctgt ccctcgccat gcactggacc tggtacctcg ctaccatgtt cctgttcatc   5640
aaggatcctg tcaacatgct cgtgtacttc ctggtgtctc aggctgtgtg cggaaacctg   5700
```

```
ctcgccatcg tgttctccct caaccacaac ggtatgcctg tgatctccaa ggaggaggct    5760
gtcgacatgg atttctttac caagcagatc atcactggtc gagatgtcca tcctggactg    5820
ttcgccaact ggttcaccgg tggcctgaac taccagatcg agcatcacct gttcccttcc    5880
atgcctcgac acaacttctc caagatccag cctgccgtcg agaccctgtg caagaagtac    5940
aacgtccgat accacaccac tggtatgatc gagggaactg ccgaggtctt ctcccgactg    6000
aacgaggtct ccaaggccac ctccaagatg ggcaaggctc agtaagcggc cgcatgagaa    6060
gataaatata taaatacatt gagatattaa atgcgctaga ttagagagcc tcatactgct    6120
cggagagaag ccaagacgag tactcaaagg ggattacacc atccatatcc acagacacaa    6180
gctggggaaa ggttctatat acactttccg gaataccgta gtttccgatg ttatcaatgg    6240
gggcagccag gatttcaggc acttcggtgt ctcggggtga aatggcgttc ttggcctcca    6300
tcaagtcgta ccatgtcttc atttgcctgt caaagtaaaa cagaagcaga tgaagaatga    6360
acttgaagtg aaggaattta aattgccccg gagaagacgg ccaggccgcc tagatgacaa    6420
attcaacaac tcacagctga ctttctgcca ttgccactag ggggggggcct ttttatatgg    6480 ccaagccaag ctctccacgt cggttgggct gcacccaaca ataaatgggt agggttgcac    6540
caacaaaggg atgggatggg gggtagaaga tacgaggata acgggctca atggcacaaa    6600 taagaacgaa tactgccatt aagactcgtg atccagcgac tgacaccatt gcatcatcta    6660
agggcctcaa aactacctcg gaactgctgc gctgatctgg acaccacaga ggttccgagc    6720
actttaggtt gcaccaaatg tcccaccagg tgcaggcaga aaacgctgga acagcgtgta    6780
cagtttgtct taacaaaaag tgagggcgct gaggtcgagc agggtggtgt gacttgttat    6840
agcctttaga gctgcgaaag cgcgtatgga tttggctcat caggccagat tgagggtctg    6900
tggacacatg tcatgttagt gtacttcaat cgccccctgg atatagcccc gacaataggc    6960
cgtggcctca ttttttttgcc ttccgcacat ttccattgct cggtacccac accttgcttc    7020
tcctgcactt gccaacctta atactggttt acattgacca acatcttaca agcgggggc    7080 ttgtctaggg tatatataaa cagtggctct cccaatcggt tgccagtctc ttttttcctt    7140 tcttttcccca cagattcgaa atctaaacta cacatcacac aatgcctgtt actgacgtcc    7200
ttaagcgaaa gtccggtgtc atcgtcggcg acgatgtccg agccgtgagt atccacgaca    7260
agatcagtgt cgagacgacg cgttttgtgt aatgacacaa tccgaaagtc gctagcaaca    7320
cacactctct acacaaacta acccagctct ccatggagtc cattgctccc ttcctgccct    7380
ccaagatgcc tcaggacctg ttcatggacc tcgccagcgc tatcggtgtc cgagctgctc    7440
cctacgtcga tcccctggag gctgccctgg ttgcccaggc cgagaagtac attcccacca    7500
ttgtccatca cactcgaggc ttcctggttg ccgtggagtc tcccctggct cgagagctgc    7560
ctctgatgaa ccccttccac gtgctcctga tcgtgctcgc ctacctggtc accgtgtttg    7620
tgggtatgca gatcatgaag aactttgaac gattcgaggt caagaccttc tccctcctgc    7680
acaacttctg tctggtctcc atctccgcct acatgtgcgg tggcatcctg tacgaggctt    7740
atcaggccaa ctatggactg tttgagaacg ctgccgatca caccttcaag ggtctcccta    7800
tggctaagat gatctggctc ttctactcct ccaagatcat ggagtttgtc gacaccatga    7860
tcatggtcct caagaagaac aaccgacaga tttcctttct gcacgtgtac caccactctt    7920
ccatcttcac catctggtgg ctggtcacct tcgttgctcc caacggtgaa gcctacttct    7980
ctgctgccct gaactccttc atccacgtca tcatgtacgg ctactacttt ctgtctgccc    8040
```

-continued

```
tgggcttcaa gcaggtgtcg ttcatcaagt tctacatcac tcgatcccag atgacccagt    8100
tctgcatgat gtctgtccag tcttcctggg acatgtacgc catgaaggtc cttggccgac    8160
ctggataccc cttcttcatc accgctctgc tctggttcta catgtggacc atgctcggtc    8220
tcttctacaa cttttaccga agaacgcca agctcgccaa gcaggccaag gctgacgctg     8280
ccaaggagaa ggccagaaag ctccagtaag cggccgcaag tgtggatggg gaagtgagtg    8340
cccggttctg tgtgcacaat tggcaatcca agatggatgg attcaacaca gggatatagc    8400
gagctacgtg gtggtgcgag gatatagcaa cggatattta tgtttgacac ttgagaatgt    8460
acgatacaag cactgtccaa gtacaatact aaacatactg tacatactca tactcgtacc    8520
cgggcaacgg tttcacttga gtgcagtggc tagtgctctt actcgtacag tgtgcaatac    8580
tgcgtatcat agtctttgat gtatatcgta ttcattcatg ttagttgcgt acgaagtcgt    8640
caatgatgtc gatatgggtt tgatcatgc acacataagg tccgaccta tcggcaagct      8700
caatgagctc cttggtggtg gtaacatcca gagaagcaca caggttggtt ttcttggctg    8760
ccacgagctt gagcactcga gcggcaaagg cggacttgtg gacgttagct cgagcttcgt    8820
aggagggcat tttggtggtg aagaggagac tgaaataaat ttagtctgca gaactttta    8880
tcggaaccttt atctggggca gtgaagtata tgttatggta atagttacga gttagttgaa   8940
cttatagata gactggacta tacgctatc ggtccaaatt agaaagaacg tcaatggctc     9000
tctgggcgtc gcctttgccg acaaaaatgt gatcatgatg aaagccagca atgacgttgc    9060
agctgatatt gttgtcggcc aaccgcgccg aaaacgcagc tgtcagaccc acagcctcca    9120
acgaagaatg tatcgtcaaa gtgatccaag cacactcata gttggagtcg tactccaaag    9180
gcggcaatga cgagtcagac agatactcgt cgacctttc cttgggaacc accaccgtca     9240
gcccttctga ctcacgtatt gtagccaccg acacaggcaa cagtccgtgg atagcagaat    9300
atgtcttgtc ggtccatttc tcaccaactt taggcgtcaa gtgaatgttg cagaagaagt    9360
atgtgccttc attgagaatc ggtgttgctg atttcaataa agtcttgaga tcagtttggc    9420
gcgccagctg cattaatgaa tcggccaacg cgcggggaga ggcggtttgc gtattgggcg    9480
ctcttccgct tcctcgctca ctgactcgct gcgctcggtc gttcggctgc ggcgagcggt    9540
atcagctcac tcaaaggcgg taatacggtt atccacagaa tcaggggata acgcaggaaa    9600
gaacatgtga gcaaaaggcc agcaaaaggc caggaaccgt aaaaaggccg cgttgctggc    9660
gtttttccat aggctccgcc cccctgacga gcatcacaaa aatcgacgct caagtcagag    9720
gtggcgaaac ccgacaggac tataaagata ccaggcgttt ccccctggaa gctccctcgt    9780
gcgctctcct gttccgaccc tgccgcttac cggatacctg tccgcctttc tcccttcggg    9840
aagcgtggcg ctttctcata gctcacgctg taggtatctc agttcggtgt aggtcgttcg    9900
ctccaagctg ggctgtgtgc acgaaccccc cgttcagccc gaccgctgcg ccttatccgg    9960
taactatcgt cttgagtcca acccggtaag acacgactta tcgccactgg cagcagccac    10020
tggtaacagg attagcagag cgaggtatgt aggcggtgct acagagttct tgaagtggtg    10080
gcctaactac ggctacacta agaacagt atttggtatc tgcgctctgc tgaagccagt      10140
taccttcgga aaagagttg gtagctcttg atccggcaaa caaaccaccg ctggtagcgg     10200
tggttttttt gtttgcaagc agcagattac gcgcagaaaa aaggatctc aagaagatcc     10260
tttgatcttt tctacggggt ctgacgctca gtggaacgaa aactcacgtt aagggatttt    10320
ggtcatgaga ttatcaaaaa ggatcttcac ctagatcctt ttaaattaaa aatgaagttt    10380
taaatcaatc taaagtatat atgagtaaac ttggtctgac agttaccaat gcttaatcag    10440
```

-continued

```
tgaggcacct atctcagcga tctgtctatt tcgttcatcc atagttgcct gactcccgt    10500 cgtgtagata actacgatac gggagggctt accatctggc cccagtgctg caatgatacc    10560
gcgagaccca cgctcaccgg ctccagattt atcagcaata aaccagccag ccggaagggc    10620
cgagcgcaga agtggtcctg caactttatc cgcctccatc cagtctatta attgttgccg    10680
ggaagctaga gtaagtagtt cgccagttaa tagtttgcgc aacgttgttg ccattgctac    10740
aggcatcgtg gtgtcacgct cgtcgtttgg tatggcttca ttcagctccg gttcccaacg    10800
atcaaggcga gttacatgat cccccatgtt gtgcaaaaaa gcggttagct ccttcggtcc    10860
tccgatcgtt gtcagaagta agttggccgc agtgttatca ctcatggtta tggcagcact    10920
gcataattct cttactgtca tgccatccgt aagatgcttt tctgtgactg gtgagtactc    10980
aaccaagtca ttctgagaat agtgtatgcg gcgaccgagt tgctcttgcc cggcgtcaat    11040
acgggataat accgcgccac atagcagaac tttaaaagtg ctcatcattg gaaaacgttc    11100
ttcggggcga aaactctcaa ggatcttacc gctgttgaga tccagttcga tgtaacccac    11160
tcgtgcaccc aactgatctt cagcatcttt tactttcacc agcgtttctg ggtgagcaaa    11220
aacaggaagg caaaatgccg caaaaaaggg aataagggcg acacggaaat gttgaatact    11280
catactcttc ctttttcaat attattgaag catttatcag ggttattgtc tcatgagcgg    11340
atacatattt gaatgtattt agaaaaataa acaaataggg gttccgcgca catttccccg    11400
aaaagtgcca cctgatgcgg tgtgaaatac cgcacagatg cgtaaggaga aaataccgca    11460
tcaggaaatt gtaagcgtta atattttgtt aaaattcgcg ttaaattttt gttaaatcag    11520 ctcattttt aaccaatagg ccgaaatcgg caaaatccct tataaatcaa agaatagac    11580 cgagataggg ttgagtgttg ttccagtttg gaacaagagt ccactattaa agaacgtgga    11640
ctccaacgtc aaagggcgaa aaaccgtcta tcagggcgat ggcccactac gtgaaccatc    11700
accctaatca agttttttgg ggtcgaggtg ccgtaaagca ctaaatcgga acccctaaagg    11760 gagccccccga tttagagctt gacggggaaa gccggcgaac gtggcgagaa aggaagggaa    11820
gaaagcgaaa ggagcgggcg ctaggggcgct ggcaagtgta gcggtcacgc tgcgcgtaac    11880
caccaccccc gccgcgctta atgcgccgct acagggcgcg tccattcgcc attcaggctg    11940
cgcaactgtt gggaagggcg atcggtgcgg gcctcttcgc tattacgcca gctggcgaaa    12000
gggggatgtg ctgcaaggcg attaagttgg gtaacgccag ggttttccca gtcacgacgt    12060
tgtaaaacga cggccagtga attgtaatac gactcactat agggcgaatt gggcccgacg    12120
tcgcatgcag tggtggtatt gtgactgggg atgtagttga gataagtcca tacacaagtc    12180
agctttcttc gagcctcata taagtataag tagttcaacg tattagcact gtacccagca    12240
tctccgtatc gagaaacaca acaacatgcc ccattggaca gatcatgcgg atacacaggt    12300
tgtgcagtat catacatact cgatcagaca ggtcgtctga ccatcataca agctgaacaa    12360
gcgctccata cttgcacgct ctctatatac acagttaaat tacatatcca tagtctaacc    12420
tctaacagtt aatcttctgg taagcctccc agccagcctt ctggtatcgc ttggcctcct    12480
caataggatc tcggttctgg ccgtacagac ctcggccgac aattatgata tccgttccgg    12540
tagacatgac atcctcaaca gttcggtact gctgtccgag agcgtctccc ttgtcgtcaa    12600
gacccacccc gggggtcaga ataagccagt cctcagagtc gcccttaat    12649
```

```
<210> SEQ ID NO 64
<211> LENGTH: 957
<212> TYPE: DNA
```

<213> ORGANISM: Mortierella alpina

<400> SEQUENCE: 64

```
atggagtcca ttgctccctt cctgccctcc aagatgcctc aggacctgtt catggacctc    60
gccagcgcta tcggtgtccg agctgctccc tacgtcgatc ccctggaggc tgccctggtt   120
gcccaggccg agaagtacat tcccaccatt gtccatcaca ctcgaggctt cctggttgcc   180
gtggagtctc ccctggctcg agagctgcct ctgatgaacc ccttccacgt gctcctgatc   240
gtgctcgcct acctggtcac cgtgtttgtg ggtatgcaga tcatgaagaa ctttgaacga   300
ttcgaggtca agaccttctc cctcctgcac aacttctgtc tggtctccat ctccgcctac   360
atgtgcggtg gcatcctgta cgaggcttat caggccaact atggactgtt tgagaacgct   420
gccgatcaca ccttcaaggg tctccctatg gctaagatga tctggctctt ctacttctcc   480
aagatcatgg agtttgtcga caccatgatc atggtcctca gaagaacaa ccgacagatt   540
tcctttctgc acgtgtacca ccactcttcc atcttcacca tctggtggct ggtcaccttc   600
gttgctccca acggtgaagc ctacttctct gctgccctga actccttcat ccacgtcatc   660
atgtacggct actactttct gtctgccctg ggcttcaagc aggtgtcgtt catcaagttc   720
tacatcactc gatcccagat gacccagttc tgcatgatgt ctgtccagtc ttcctgggac   780
atgtacgcca tgaaggtcct tggccgacct ggataccct tcttcatcac cgctctgctc   840
tggttctaca tgtggaccat gctcggtctc ttctacaact tttaccgaaa gaacgccaag   900
ctcgccaagc aggccaaggc tgacgctgcc aaggagaagg ccagaaagct ccagtaa      957
```

<210> SEQ ID NO 65
<211> LENGTH: 318
<212> TYPE: PRT
<213> ORGANISM: Mortierella alpina (GenBank Accession No. AX464731)

<400> SEQUENCE: 65

```
Met Glu Ser Ile Ala Pro Phe Leu Pro Ser Lys Met Pro Gln Asp Leu
 1               5                  10                  15

Phe Met Asp Leu Ala Thr Ala Ile Gly Val Arg Ala Ala Pro Tyr Val
            20                  25                  30

Asp Pro Leu Glu Ala Ala Leu Val Ala Gln Ala Glu Lys Tyr Ile Pro
        35                  40                  45

Thr Ile Val His His Thr Arg Gly Phe Leu Val Ala Val Glu Ser Pro
    50                  55                  60

Leu Ala Arg Glu Leu Pro Leu Met Asn Pro Phe His Val Leu Leu Ile
65                  70                  75                  80

Val Leu Ala Tyr Leu Val Thr Val Phe Val Gly Met Gln Ile Met Lys
                85                  90                  95

Asn Phe Glu Arg Phe Glu Val Lys Thr Phe Ser Leu Leu His Asn Phe
            100                 105                 110

Cys Leu Val Ser Ile Ser Ala Tyr Met Cys Gly Gly Ile Leu Tyr Glu
        115                 120                 125

Ala Tyr Gln Ala Asn Tyr Gly Leu Phe Glu Asn Ala Ala Asp His Thr
    130                 135                 140

Phe Lys Gly Leu Pro Met Ala Lys Met Ile Trp Leu Phe Tyr Phe Ser
145                 150                 155                 160

Lys Ile Met Glu Phe Val Asp Thr Met Ile Met Val Leu Lys Lys Asn
                165                 170                 175

Asn Arg Gln Ile Ser Phe Leu His Val Tyr His His Ser Ser Ile Phe
            180                 185                 190
```

```
Thr Ile Trp Trp Leu Val Thr Phe Val Ala Pro Asn Gly Glu Ala Tyr
            195                 200                 205

Phe Ser Ala Ala Leu Asn Ser Phe Ile His Val Ile Met Tyr Gly Tyr
        210                 215                 220

Tyr Phe Leu Ser Ala Leu Gly Phe Lys Gln Val Ser Phe Ile Lys Phe
225                 230                 235                 240

Tyr Ile Thr Arg Ser Gln Met Thr Gln Phe Cys Met Met Ser Val Gln
                245                 250                 255

Ser Ser Trp Asp Met Tyr Ala Met Lys Val Leu Gly Arg Pro Gly Tyr
            260                 265                 270

Pro Phe Phe Ile Thr Ala Leu Leu Trp Phe Tyr Met Trp Thr Met Leu
        275                 280                 285

Gly Leu Phe Tyr Asn Phe Tyr Arg Lys Asn Ala Lys Leu Ala Lys Gln
        290                 295                 300

Ala Lys Ala Asp Ala Ala Lys Glu Lys Ala Arg Lys Leu Gln
305                 310                 315
```

<210> SEQ ID NO 66
<211> LENGTH: 1374
<212> TYPE: DNA
<213> ORGANISM: Mortierella alpina

<400> SEQUENCE: 66

```
atggctgccg ctccctctgt gcgaaccttt acccgagccg aggttctgaa cgctgaggct      60
ctgaacgagg gcaagaagga cgctgaggct cccttcctga tgatcatcga caacaaggtg     120
tacgacgtcc gagagttcgt ccctgaccat cctggaggct ccgtgattct cacccacgtt     180
ggcaaggacg caccgacgt cttt gacacc tttcatcccg aggctgcttg ggagactctc     240
gccaacttct acgttggaga cattgacgag tccgaccgag acatcaagaa cgatgacttt     300
gccgctgagg tccgaaagct gcgaaccctg ttccagtctc tcggctacta cgactcctct     360
aaggcctact acgccttcaa ggtctccttc aacctctgca tctggggact gtccaccgtc     420
attgtggcca gtgggggtca gacctccacc ctcgccaacg tgctctctgc tgccctgctc     480
ggcctgttct ggcagcagtg cggatggctg gctcacgact tctgcacca ccaggtcttc     540
caggaccgat tctggggtga tctcttcgga gccttcctgg aggtgtctg ccagggcttc     600
tcctcttcct ggtggaagga caagcacaac actcaccatg ccgctcccaa cgtgcatggc     660
gaggatcctg acattgacac ccaccctctc ctgacctggt ccgagcacgc tctggagatg     720
ttctccgacg tccccgatga ggagctgacc cgaatgtggt ctcgattcat ggtcctgaac     780
cagacctggt tctacttccc cattctctcc ttcgctcgac tgtcttggtg cctccagtcc     840
attctctttg tgctgcccaa cggtcaggct cacaagccct ccggagctcg agtgcccatc     900
tccctggtcg agcagctgtc cctcgccatg cactggacct ggtacctcgc taccatgttc     960
ctgttcatca aggatcctgt caacatgctc gtgtacttcc tggtgtctca ggctgtgtgc    1020
ggaaacctgc tcgccatcgt gttctccctc aaccacaacg gtatgcctgt gatctccaag    1080
gaggaggctg tcgacatgga tttctttacc aagcagatca tcactggtcg agatgtccat    1140
cctggactgt tcgccaactg gttcaccggt ggcctgaact accagatcga gcatcacctg    1200
ttcccttcca tgcctcgaca caacttctcc aagatccagc tgccgtcga gaccctgtgc    1260
aagaagtaca cgtccgata ccacaccact ggtatgatcg agggaactgc cgaggtcttc    1320
tcccgactga acgaggtctc caaggccacc tccaagatgg gcaaggctca gtaa          1374
```

```
<210> SEQ ID NO 67
<211> LENGTH: 457
<212> TYPE: PRT
<213> ORGANISM: Mortierella alpina (GenBank Accession No. AF465281)

<400> SEQUENCE: 67
```

| | | | | | | | | | | | | | | |
|---|---|---|---|---|---|---|---|---|---|---|---|---|---|---|
| Met | Ala | Ala | Ala | Pro | Ser | Val | Arg | Thr | Phe | Thr | Arg | Ala | Glu | Val | Leu |
| 1 | | | | 5 | | | | | 10 | | | | | 15 | |
| Asn | Ala | Glu | Ala | Leu | Asn | Glu | Gly | Lys | Lys | Asp | Ala | Glu | Ala | Pro | Phe |
| | | | 20 | | | | | 25 | | | | | 30 | | |
| Leu | Met | Ile | Ile | Asp | Asn | Lys | Val | Tyr | Asp | Val | Arg | Glu | Phe | Val | Pro |
| | | 35 | | | | | 40 | | | | | 45 | | | |
| Asp | His | Pro | Gly | Gly | Ser | Val | Ile | Leu | Thr | His | Val | Gly | Lys | Asp | Gly |
| | 50 | | | | | 55 | | | | | 60 | | | | |
| Thr | Asp | Val | Phe | Asp | Thr | Phe | His | Pro | Glu | Ala | Ala | Trp | Glu | Thr | Leu |
| 65 | | | | | 70 | | | | | 75 | | | | | 80 |
| Ala | Asn | Phe | Tyr | Val | Gly | Asp | Ile | Asp | Glu | Ser | Asp | Arg | Asp | Ile | Lys |
| | | | | 85 | | | | | 90 | | | | | 95 | |
| Asn | Asp | Asp | Phe | Ala | Ala | Glu | Val | Arg | Lys | Leu | Arg | Thr | Leu | Phe | Gln |
| | | | 100 | | | | | 105 | | | | | 110 | | |
| Ser | Leu | Gly | Tyr | Tyr | Asp | Ser | Ser | Lys | Ala | Tyr | Tyr | Ala | Phe | Lys | Val |
| | | 115 | | | | | 120 | | | | | 125 | | | |
| Ser | Phe | Asn | Leu | Cys | Ile | Trp | Gly | Leu | Ser | Thr | Val | Ile | Val | Ala | Lys |
| | 130 | | | | | 135 | | | | | 140 | | | | |
| Trp | Gly | Gln | Thr | Ser | Thr | Leu | Ala | Asn | Val | Leu | Ser | Ala | Ala | Leu | Leu |
| 145 | | | | | 150 | | | | | 155 | | | | | 160 |
| Gly | Leu | Phe | Trp | Gln | Gln | Cys | Gly | Trp | Leu | Ala | His | Asp | Phe | Leu | His |
| | | | | 165 | | | | | 170 | | | | | 175 | |
| His | Gln | Val | Phe | Gln | Asp | Arg | Phe | Trp | Gly | Asp | Leu | Phe | Gly | Ala | Phe |
| | | | 180 | | | | | 185 | | | | | 190 | | |
| Leu | Gly | Gly | Val | Cys | Gln | Gly | Phe | Ser | Ser | Ser | Trp | Trp | Lys | Asp | Lys |
| | | 195 | | | | | 200 | | | | | 205 | | | |
| His | Asn | Thr | His | His | Ala | Ala | Pro | Asn | Val | His | Gly | Glu | Asp | Pro | Asp |
| | 210 | | | | | 215 | | | | | 220 | | | | |
| Ile | Asp | Thr | His | Pro | Leu | Leu | Thr | Trp | Ser | Glu | His | Ala | Leu | Glu | Met |
| 225 | | | | | 230 | | | | | 235 | | | | | 240 |
| Phe | Ser | Asp | Val | Pro | Asp | Glu | Glu | Leu | Thr | Arg | Met | Trp | Ser | Arg | Phe |
| | | | | 245 | | | | | 250 | | | | | 255 | |
| Met | Val | Leu | Asn | Gln | Thr | Trp | Phe | Tyr | Phe | Pro | Ile | Leu | Ser | Phe | Ala |
| | | | 260 | | | | | 265 | | | | | 270 | | |
| Arg | Leu | Ser | Trp | Cys | Leu | Gln | Ser | Ile | Leu | Phe | Val | Leu | Pro | Asn | Gly |
| | | 275 | | | | | 280 | | | | | 285 | | | |
| Gln | Ala | His | Lys | Pro | Ser | Gly | Ala | Arg | Val | Pro | Ile | Ser | Leu | Val | Glu |
| | 290 | | | | | 295 | | | | | 300 | | | | |
| Gln | Leu | Ser | Leu | Ala | Met | His | Trp | Thr | Trp | Tyr | Leu | Ala | Thr | Met | Phe |
| 305 | | | | | 310 | | | | | 315 | | | | | 320 |
| Leu | Phe | Ile | Lys | Asp | Pro | Val | Asn | Met | Leu | Val | Tyr | Phe | Leu | Val | Ser |
| | | | | 325 | | | | | 330 | | | | | 335 | |
| Gln | Ala | Val | Cys | Gly | Asn | Leu | Leu | Ala | Ile | Val | Phe | Ser | Leu | Asn | His |
| | | | 340 | | | | | 345 | | | | | 350 | | |
| Asn | Gly | Met | Pro | Val | Ile | Ser | Lys | Glu | Glu | Ala | Val | Asp | Met | Asp | Phe |
| | | 355 | | | | | 360 | | | | | 365 | | | |
| Phe | Thr | Lys | Gln | Ile | Ile | Thr | Gly | Arg | Asp | Val | His | Pro | Gly | Leu | Phe |
| | 370 | | | | | 375 | | | | | 380 | | | | |

Ala Asn Trp Phe Thr Gly Gly Leu Asn Tyr Gln Ile Glu His His Leu
385                 390                 395                 400

Phe Pro Ser Met Pro Arg His Asn Phe Ser Lys Ile Gln Pro Ala Val
                405                 410                 415

Glu Thr Leu Cys Lys Lys Tyr Asn Val Arg Tyr His Thr Thr Gly Met
            420                 425                 430

Ile Glu Gly Thr Ala Glu Val Phe Ser Arg Leu Asn Glu Val Ser Lys
        435                 440                 445

Ala Thr Ser Lys Met Gly Lys Ala Gln
    450                 455

<210> SEQ ID NO 68
<211> LENGTH: 1434
<212> TYPE: DNA
<213> ORGANISM: Fusarium monoliforme

<400> SEQUENCE: 68

```
atggcgtcca cttcggctct gcccaagcag aaccctgcgc ttagacgcac cgtcacctca      60
actactgtga cggattctga gtctgccgcc gtctctcctt cagactctcc ccgccactcg     120
gcctcttcca catcgctctc gtccatgtcc gaggttgata tcgccaagcc caagtccgag     180
tatggtgtca tgctcgacac ctacggcaac cagttcgagg ttcccgactt taccatcaag     240
gacatctaca atgccatccc taagcactgc ttcaagcgct ccgctctcaa gggatacggt     300
tatatcctcc gcgacattgt cctcctgact accactttca gcatctgcta caactttgtg     360
accccgaat atatcccctc caccccgcc cgcgctggtc tgtgggccgt gtacaccgtt     420
cttcagggtc ttttcggtac tggtctctgg gttattgccc atgagtgcgg tcacggtgct     480
ttctccgatt ctcgcatcat caacgacatt actggctggg ttcttcactc ttccctcctt     540
gtcccctact tcagctggca aatctcccac cgaaagcacc acaaggccac tgcaacatg     600
gagcgtgaca tggtcttcgt tccccgaacc cgcgagcagc aggctactcg tctcggaaag     660
atgacccacg agctcgctca tcttactgag gagaccccg ctttcactct tctcatgctc     720
gtccttcagc agctcgttgg ctggcccaac tacctcatca ccaatgttac cggccacaac     780
taccacgagc gccagcgtga gggtcgcggc aagggcaagc ataacggcct cggcggtggt     840
gttaaccact cgatccccg cagccctctg tacgagaaca gtgacgctaa gctcatcgtc     900
ctcagcgata ttggtatcgg tctgatggcc actgctctgt acttcctcgt tcagaagttc     960
ggtttctaca acatggccat ctggtacttt gttcccctacc tctgggttaa ccactggctc    1020
gttgccatca ccttcctcca gcacaccgac cctacccttc cccactacac caacgacgag    1080
tggaacttcg tccgtggtgc cgctgctacc attgaccgtg agatgggctt catcggccgc    1140
caccttctcc acggcatcat cgagactcat gtcctccacc actacgtcag cagcatcccc    1200
ttctacaacg cggacgaggc caccgaggcc attaagccca tcatgggcaa gcactaccgg    1260
gctgatgtcc aggatggtcc tcgtggcttc atccgcgcca tgtaccgcag tgcgcgtatg    1320
tgccagtggg ttgagcccag cgctggtgcc gagggtgctg gtaagggtgt tctgttcttc    1380
cgcaaccgca caacgtggg cacccccccc gctgttatca agcccgttgc ttaa          1434
```

<210> SEQ ID NO 69
<211> LENGTH: 477
<212> TYPE: PRT
<213> ORGANISM: Fusarium monoliforme

<400> SEQUENCE: 69

```
Met Ala Ser Thr Ser Ala Leu Pro Lys Gln Asn Pro Ala Leu Arg Arg
1               5                   10                  15

Thr Val Thr Ser Thr Thr Val Thr Asp Ser Glu Ser Ala Ala Val Ser
            20                  25                  30

Pro Ser Asp Ser Pro Arg His Ser Ala Ser Thr Ser Leu Ser Ser
        35                  40                  45

Met Ser Glu Val Asp Ile Ala Lys Pro Lys Ser Glu Tyr Gly Val Met
50                  55                  60

Leu Asp Thr Tyr Gly Asn Gln Phe Glu Val Pro Asp Phe Thr Ile Lys
65                  70                  75                  80

Asp Ile Tyr Asn Ala Ile Pro Lys His Cys Phe Lys Arg Ser Ala Leu
                85                  90                  95

Lys Gly Tyr Gly Tyr Ile Leu Arg Asp Ile Val Leu Leu Thr Thr Thr
                100                 105                 110

Phe Ser Ile Trp Tyr Asn Phe Val Thr Pro Glu Tyr Ile Pro Ser Thr
                115                 120                 125

Pro Ala Arg Ala Gly Leu Trp Ala Val Tyr Thr Val Leu Gln Gly Leu
130                 135                 140

Phe Gly Thr Gly Leu Trp Val Ile Ala His Glu Cys Gly His Gly Ala
145                 150                 155                 160

Phe Ser Asp Ser Arg Ile Ile Asn Asp Ile Thr Gly Trp Val Leu His
                165                 170                 175

Ser Ser Leu Leu Val Pro Tyr Phe Ser Trp Gln Ile Ser His Arg Lys
            180                 185                 190

His His Lys Ala Thr Gly Asn Met Glu Arg Asp Met Val Phe Val Pro
        195                 200                 205

Arg Thr Arg Glu Gln Gln Ala Thr Arg Leu Gly Lys Met Thr His Glu
210                 215                 220

Leu Ala His Leu Thr Glu Glu Thr Pro Ala Phe Thr Leu Leu Met Leu
225                 230                 235                 240

Val Leu Gln Gln Leu Val Gly Trp Pro Asn Tyr Leu Ile Thr Asn Val
                245                 250                 255

Thr Gly His Asn Tyr His Glu Arg Gln Arg Glu Gly Arg Gly Lys Gly
            260                 265                 270

Lys His Asn Gly Leu Gly Gly Val Asn His Phe Asp Pro Arg Ser
        275                 280                 285

Pro Leu Tyr Glu Asn Ser Asp Ala Lys Leu Ile Val Leu Ser Asp Ile
    290                 295                 300

Gly Ile Gly Leu Met Ala Thr Ala Leu Tyr Phe Leu Val Gln Lys Phe
305                 310                 315                 320

Gly Phe Tyr Asn Met Ala Ile Trp Tyr Phe Val Pro Tyr Leu Trp Val
                325                 330                 335

Asn His Trp Leu Val Ala Ile Thr Phe Leu Gln His Thr Asp Pro Thr
            340                 345                 350

Leu Pro His Tyr Thr Asn Asp Glu Trp Asn Phe Val Arg Gly Ala Ala
        355                 360                 365

Ala Thr Ile Asp Arg Glu Met Gly Phe Ile Gly Arg His Leu Leu His
    370                 375                 380

Gly Ile Ile Glu Thr His Val Leu His His Tyr Val Ser Ser Ile Pro
385                 390                 395                 400

Phe Tyr Asn Ala Asp Glu Ala Thr Glu Ala Ile Lys Pro Ile Met Gly
                405                 410                 415
```

```
Lys His Tyr Arg Ala Asp Val Gln Asp Gly Pro Arg Gly Phe Ile Arg
                420                 425                 430

Ala Met Tyr Arg Ser Ala Arg Met Cys Gln Trp Val Glu Pro Ser Ala
            435                 440                 445

Gly Ala Glu Gly Ala Gly Lys Gly Val Leu Phe Phe Arg Asn Arg Asn
        450                 455                 460

Asn Val Gly Thr Pro Pro Ala Val Ile Lys Pro Val Ala
465                 470                 475

<210> SEQ ID NO 70
<211> LENGTH: 819
<212> TYPE: DNA
<213> ORGANISM: Thraustochytrium aureum

<400> SEQUENCE: 70
atggccaact cctctgtctg ggacgacgtg gtcggacgag tcgagaccgg tgtcgaccag    60
tggatggacg gagctaagcc ctacgctctg accgacggtc tgcccatgat ggacgtctcc   120
accatgctcg ccttcgaggt cggctacatg gccatgctgc tcttcggcat tcccatcatg   180
aagcagatgg agaagccctt cgagctgaag accatcaagc tgctccacaa cctgttcctc   240
ttcggactgt ccctctacat gtgcgtcgag accatccgac aggctatcct gggtggctac   300
aaggtcttcg gcaacgacat ggagaagggc aacgagtccc acgctcaggg catgtcccga   360
atcgtctacg tgttctacgt ctccaaggcc tacgagttcc tggacaccgc tatcatgatc   420
ctgtgcaaga gttcaaccag gtctccttc ctgcacgtgt accaccatgc caccatcttc   480
gccatctggt gggctattgc caagtacgct cctggtggcg acgcctactt ctccgtcatc   540
ctcaactcct tcgtccacac cgtcatgtac gcctactact tcttttcctc tcagggcttc   600
ggcttcgtca agcccatcaa gccctacatc accactctgc agatgaccca gttcatggct   660
atgctggtgc agtccctgta cgactacctc ttccctgcg actaccctca ggctctggtc   720
cagctgctcg gcgtgtacat gatcaccctg ctcgctctgt tcggcaactt ctttgtccag   780
tcctacctga agaagcccaa gaagtccaag accaactaa                          819

<210> SEQ ID NO 71
<211> LENGTH: 272
<212> TYPE: PRT
<213> ORGANISM: Thraustochytrium aureum

<400> SEQUENCE: 71

Met Ala Asn Ser Ser Val Trp Asp Asp Val Val Gly Arg Val Glu Thr
1               5                   10                  15

Gly Val Asp Gln Trp Met Asp Gly Ala Lys Pro Tyr Ala Leu Thr Asp
            20                  25                  30

Gly Leu Pro Met Met Asp Val Ser Thr Met Leu Ala Phe Glu Val Gly
        35                  40                  45

Tyr Met Ala Met Leu Leu Phe Gly Ile Pro Ile Met Lys Gln Met Glu
    50                  55                  60

Lys Pro Phe Glu Leu Lys Thr Ile Lys Leu Leu His Asn Leu Phe Leu
65                  70                  75                  80

Phe Gly Leu Ser Leu Tyr Met Cys Val Glu Thr Ile Arg Gln Ala Ile
                85                  90                  95

Leu Gly Gly Tyr Lys Val Phe Gly Asn Asp Met Glu Lys Gly Asn Glu
            100                 105                 110

Ser His Ala Gln Gly Met Ser Arg Ile Val Tyr Val Phe Tyr Val Ser
        115                 120                 125
```

Lys Ala Tyr Glu Phe Leu Asp Thr Ala Ile Met Ile Leu Cys Lys Lys
    130                 135                 140

Phe Asn Gln Val Ser Phe Leu His Val Tyr His His Ala Thr Ile Phe
145                 150                 155                 160

Ala Ile Trp Trp Ala Ile Ala Lys Tyr Ala Pro Gly Gly Asp Ala Tyr
                165                 170                 175

Phe Ser Val Ile Leu Asn Ser Phe Val His Thr Val Met Tyr Ala Tyr
                180                 185                 190

Tyr Phe Phe Ser Ser Gln Gly Phe Gly Phe Val Lys Pro Ile Lys Pro
            195                 200                 205

Tyr Ile Thr Thr Leu Gln Met Thr Gln Phe Met Ala Met Leu Val Gln
    210                 215                 220

Ser Leu Tyr Asp Tyr Leu Phe Pro Cys Asp Tyr Pro Gln Ala Leu Val
225                 230                 235                 240

Gln Leu Leu Gly Val Tyr Met Ile Thr Leu Leu Ala Leu Phe Gly Asn
                245                 250                 255

Phe Phe Val Gln Ser Tyr Leu Lys Lys Pro Lys Lys Ser Lys Thr Asn
            260                 265                 270

<210> SEQ ID NO 72
<211> LENGTH: 924
<212> TYPE: DNA
<213> ORGANISM: Yarrowia lipolytica
<220> FEATURE:
<221> NAME/KEY: misc_feature
<223> OTHER INFORMATION: Promoter FBAINm

<400> SEQUENCE: 72

| | |
|---|---|
| aaattgcccc ggagaagacg gccaggccgc ctagatgaca aattcaacaa ctcacagctg | 60 |
| actttctgcc attgccacta ggggggggcc tttttatatg gccaagccaa gctctccacg | 120 |
| tcggttgggc tgcacccaac aataaatggg tagggttgca ccaacaaagg gatgggatgg | 180 |
| ggggtagaag atacgaggat aacgggggctc aatggcacaa ataagaacga atactgccat | 240 |
| taagactcgt gatccagcga ctgacaccat tgcatcatct aagggcctca aaactacctc | 300 |
| ggaactgctg cgctgatctg gacaccacag aggttccgag cactttaggt tgcaccaaat | 360 |
| gtcccaccag gtgcaggcag aaaacgctgg aacagcgtgt acagtttgtc ttaacaaaaa | 420 |
| gtgagggcgc tgaggtcgag cagggtggtg tgacttgtta tagcctttag agctgcgaaa | 480 |
| gcgcgtatgg atttggctca tcaggccaga ttgagggtct gtggacacat gtcatgttag | 540 |
| tgtacttcaa tcgcccctg gatatagccc cgacaatagg ccgtggcctc attttttgc | 600 |
| cttccgcaca tttccattgc tcggtaccca caccttgctt ctcctgcact tgccaacctt | 660 |
| aatactggtt tacattgacc aacatcttac aagcgggggg cttgtctagg gtatatataa | 720 |
| acagtggctc tcccaatcgg ttgccagtct cttttttcct ttctttcccc acagattcga | 780 |
| aatctaaact acacatcaca gaattccgag ccgtgagtat ccacgacaag atcagtgtcg | 840 |
| agacgacgcg ttttgtgtaa tgacacaatc cgaaagtcgc tagcaacaca cactctctac | 900 |
| acaaactaac ccagctctgg tacc | 924 |

What is claimed is:

1. A method for the expression of a coding region of interest in a transformed yeast cell comprising:
   (a) providing a transformed yeast cell having a chimeric gene comprising:
      (i) a regulatory sequence of the *Yarrowia* fba1 gene; and,
      (ii) a coding region of interest expressible in the yeast cell;
      wherein the regulatory sequence is operably linked to the coding region of interest; and
   (b) growing the transformed yeast cell of step (a) under conditions whereby the chimeric gene of step (a) is expressed.

2. A method according to claim 1 wherein the regulatory sequence of the *Yarrowia* fba1 gene is selected from the group consisting of: a FBA promoter region; a FBAIN promoter region; a FBAINm promoter region; and a chimeric promoter comprising the fba1 intron.

3. A method according to claim 1 wherein the regulatory sequence of the *Yarrowia* fba1 gene is isolated from *Yarrowia lipolytica*.

4. A method according to claim 1 wherein the transformed yeast cell is an oleaginous yeast.

5. A method of claim 4, wherein the oleaginous yeast is a member of a genus selected from the group consisting of *Yarrowia, Candida, Rhodotorula, Rhodosporidium, Cryptococcus, Trichosporon* and *Lipomyces*.

6. A method according to claim 1 wherein the coding region of interest encodes a polypeptide selected from the group consisting of: desaturases, elongases, acyltransferases, aminopeptidases, amylases, carbohydrases, carboxypeptidases, catalyases, cellulases, chitinases, cutinases, cyclodextrin glycosyltransferases, deoxyribonucleases, esterases, α-galactosidases, β-galactosidases, glucoamylases, α-glucosidases, β-glucanases, β-glucosidases, invertases, laccases, lipases, mannosidases, mutanases, oxidases, pectinolytic enzymes, peroxidases, phospholipases, phytases, polyphenoloxidases, proteolytic enzymes, ribonucleases, trausglutaminases and xylanases.

7. A plasmid comprising a regulatory sequence of a *Yarrowia* fab1 gene selected from the group consisting of a FBA promoter region, FBAIN promoter region and an FBAINm promoter region.

8. A plasmid comprising fba1 intron of a *Yarrowia* fab1 gene.

* * * * *

UNITED STATES PATENT AND TRADEMARK OFFICE
CERTIFICATE OF CORRECTION

| | | |
|---|---|---|
| PATENT NO. | : 7,202,356 B2 | Page 1 of 1 |
| APPLICATION NO. | : 10/987548 | |
| DATED | : April 10, 2007 | |
| INVENTOR(S) | : Dana M. Walters Pollak and Quinn Qun Zhu | |

It is certified that error appears in the above-identified patent and that said Letters Patent is hereby corrected as shown below:

Column 29, line 21, change "γ-Linoleic" to --γ-Linolenic--
Column 29, line 23, change "Dihomo-γ-Linoleic" to --Dihomo-γ-Linolenic--

Signed and Sealed this

Eleventh Day of December, 2007

JON W. DUDAS
*Director of the United States Patent and Trademark Office*